(12) United States Patent
Tajima et al.

(10) Patent No.: US 7,220,864 B2
(45) Date of Patent: May 22, 2007

(54) DIHYDRONAPHTHALENE DERIVATIVE COMPOUNDS AND AGENT COMPRISING THE DERIVATIVE AS ACTIVE INGREDIENT

(75) Inventors: Hisao Tajima, Mishima-gun (JP); Yoshisuke Nakayama, Mishima-gun (JP); Daikichi Fukushima, Mishima-gun (JP)

(73) Assignee: Ono Pharmaceutical Co., Ltd., Osaka (JP)

( * ) Notice: Subject to any disclaimer, the term of this patent is extended or adjusted under 35 U.S.C. 154(b) by 502 days.

(21) Appl. No.: 10/451,679

(22) PCT Filed: Dec. 21, 2001

(86) PCT No.: PCT/JP01/11255

§ 371 (c)(1),
(2), (4) Date: Feb. 9, 2004

(87) PCT Pub. No.: WO02/051820

PCT Pub. Date: Jul. 4, 2002

(65) Prior Publication Data
US 2004/0138213 A1    Jul. 15, 2004

(30) Foreign Application Priority Data
Dec. 25, 2000    (JP) .............................. 2000-392723

(51) Int. Cl.
  *C07D 263/32*    (2006.01)
(52) U.S. Cl. ..................................................... 548/236
(58) Field of Classification Search ................ 548/236
See application file for complete search history.

(56) References Cited

U.S. PATENT DOCUMENTS 5,599,826 A * 2/1997 Mertens et al. ............ 514/364

FOREIGN PATENT DOCUMENTS

WO    WO 97/31907 A1    9/1997
WO    WO 99/11255 A1    3/1999

OTHER PUBLICATIONS

International Search Report dated Mar. 12, 2002.
Garret J. Etgen et al., "The Dual Peroxisome Proliferator—Activated Receptor—@/Agonist LY465608 Ameliorates Insulin Resistance and Diabetic Hyperglycemia While Improving Cardiovascular Risk Factors in Preclinical Modesl", Diabetes (2002) vol. 51, pp. 1083-1087.
Koji Murakami et al., "Effect of PPAR-α Activation on Abnormal Lipid Metabolism in Liver of Zucker Fatty Rats", Diabetes (1998) vol. 47, pp. 1841-1847.
Carols Bernal-Mizrachi et al., "Respiratory Uncoupling Lowers Blood Pressure Through a Leptin-Dependent Mechanism in Genetically Obese Mice", Arterioscler Thromb Vasc. Biol. (2002) vol. 22, pp. 961-968.
Anne R. Miller et al., "Novel peroxisome proliferators-activated receptor ligands for Type 2 diabetes and the metabolic syndrome", Expert Oin. Investig. Drugs (2003), vol. 12, pp. 1489-1500.
F.P. Mancini et al., "Fenofibrate prevents and reduces body weight gain and adiposity in diet-induced obese rats", FEBS Letters (2001), vol. 491, pp. 154-158.
Deborah A. Winegar et al., "Effects of fenofibrate on lipid parameters in obese rhesus monkeys", J. Lipid. Res. (2001), vol. 42, pp. 1543-1551.

* cited by examiner

*Primary Examiner*—Kamal A. Saeed
*Assistant Examiner*—Shawquia Young
(74) *Attorney, Agent, or Firm*—Sughrue Mion, PLLC

(57) ABSTRACT

The compound 3-(5-(2-(2-(4-methylphenyl)-5-methyloxazol-4-yl)ethoxy)-3,4-dihydronaphthalene-1-yl)propanoic acid or a nontoxic salt thereof. Because this compound has activity of regulating peroxisome proliferators activated receptor regulator, it is useful as a hyperglycemic agent, a hypolipidemic agent, a preventative and/or treatment agent for diseases associated with metabolic disorders etc.

2 Claims, No Drawings

DIHYDRONAPHTHALENE DERIVATIVE COMPOUNDS AND AGENT COMPRISING THE DERIVATIVE AS ACTIVE INGREDIENT

TECHNICAL FIELD

The present invention relates to dihydronaphthalene derivative compounds.

More specifically, the present invention relates to (1) dihydronaphthalene derivatives compounds represented by formula

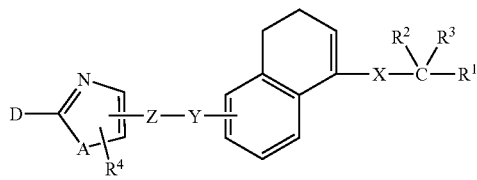

(wherein all symbols have the same meanings as described below), or nontoxic salts thereof, (2) a process for preparing thereof, and (3) an agent comprising thereof as an active ingredient.

BACKGROUND ART

Recently in the study of transcription factors concerned with marker genes expression in adipocytes differentiation, peroxisome proliferator activated receptor (abbreviated as PPAR hereinafter), which is one of intranuclear receptors, has been focused. cDNAs of PPAR were cloned from various kinds of animals, and plural isoform genes were found, particularly in mammals three types of isoforms (α, δ, γ) are known (see J. Steroid Biochem. Molec. Biol., 51, 157 (1994); Gene Expression., 4, 281 (1995); Biochem Biophys. Res. Commun., 224, 431 (1996); Mol. Endocrinology., 6, 1634 (1992)). PPAR γ isoform is predominantly expressed in adipose tissues, immune cells, adrenal gland, spleen, small intestine. PPAR α isoform is mainly expressed in adipose tissue, liver, retina, and PPAR δ isoform is widely expressed without specificity for tissue (see Endocrinology., 137, 354 (1996)).

On the other hand, the following thiazolidine derivatives are known as agents for the treatment of non-insulin dependent diabetes mellitus (NIDDM) and are hypoglycemic agents which are used for the improvement of hyperglycemia in the patients suffering from diabetes. They are also effective for the improvement of hyperinsulinemia, glucose tolerance and decrease of serum lipid and therefore they are thought to be considerably hopeful as agents for the treatment of insulin resistance.

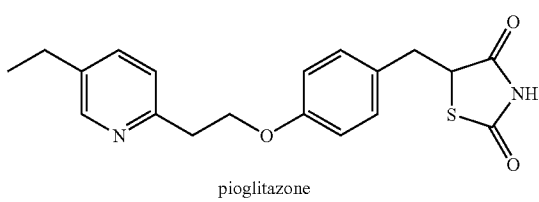

pioglitazone

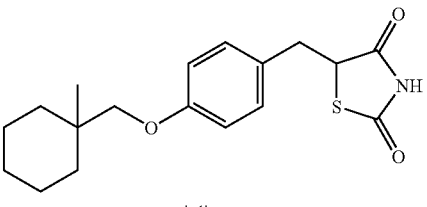

ciglitazone

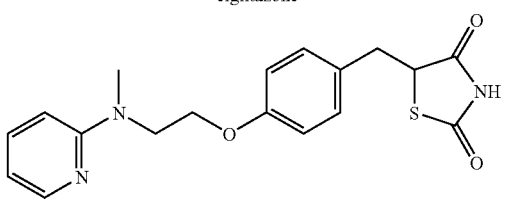

BRL49653

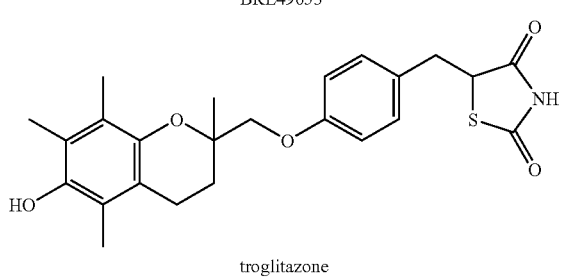

troglitazone

One of the target proteins in the cells of these thiazolidine derivatives is exactly PPAR γ and it is resolved that they enhance the transcription activity of PPAR γ (see Endocrinology., 137, 4189 (1996); Cell., 83, 803 (1995); Cell., 83, 813 (1995); J. Biol. Chem., 270, 12953 (1995)). Therefore, a PPAR γ activator (agonist) which enhances its transcription activity is thought to be hopeful as a hypoglycemic agent and/or a hypolipidemic agent. Furthermore, since a PPAR γ agonist is known to promote the expression of PPAR γ protein itself (Genes & Development., 10, 974 (1996)), an agent which increases the expression of PPAR γ protein itself as well as PPAR γ activating agent is also thought to be clinically useful.

PPAR γ is related to adipocytes differentiation (see J. Biol. Chem., 272, 5637 (1997) and Cell., 83, 803 (1995)). It is known that thiazolidine derivatives which activate this receptor promote adipocytes differentiation. Recently it was reported that thiazolidine derivatives increase fat mass and cause man to gain weight and to become obese (see Lancet., 349, 952 (1997)). Therefore, it is also thought that antagonists which inhibit PPAR γ activity and agents that decrease the expression of PPAR γ protein itself are also clinically applicable. On the other hand, a compound that phosphorylates PPAR γ protein and decreases its activity is reported (Science., 274, 2100 (1996)). This implies that an agent which does not bind on PPAR γ protein as a ligand, but inhibits its activity is also clinically applicable.

From these, PPAR γ activators (agonists) and PPAR γ regulators for its expression that can increase the expression of the protein itself are expected to be useful as hypoglycemic agents, hypolipidemic agents, and agents for prevention and/or treatment of diseases associated with metabolic disorders such as diabetes, obesity, syndrome X, hypercholesterolemia and hyperlipoproteinemia etc., hyperlipidemia, atherosclerosis, hypertension, circulatory diseases and overeating etc.

On the other hand, antagonists that inhibit the transcription activity of PPAR γ or PPAR γ regulators that inhibit the expression of the protein itself are expected to be useful as hypoglycemic agents and agents for prevention and/or treatment of diseases associated with metabolic disorders such as diabetes, obesity and syndrome X etc., hyperlipidemia, atherosclerosis, hypertension and overeating etc.

The following fibrate compound (e.g. chlofibrate) is known as a hypolipidemic agent.

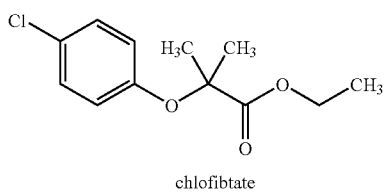

chlofibtate

And, it is also resolved that one of the target proteins in the cells of fibrate compounds is PPAR α (see Nature., 347, 645 (1990); J. Steroid Biochem. Molec. Biol., 51, 157 (1994); Biochemistry., 32, 5598 (1993)). From these facts, PPAR α regulators which can be activated by fibrate compounds are thought to have a hypolipidemic effect, and so they are expected to be useful as agents for prevention and/or treatment of hyperlipidemia etc.

Besides, it has been recently reported that PPAR α possesses anti-obese activity in the specification of WO 9736579. In addition, it was reported that the elevation of high density lipoprotein (HDL) cholesterol level and the reduction of low density lipoprotein (LDL) cholesterol, very low density lipoprotein (VLDL) cholesterol and triglyceride levels were induced by activation of PPAR α (J. Lipid Res., 39, 17 (1998)). It was also reported that composition of fatty acids in blood, hypertension and insulin resistance were improved by administration of bezafibrate which is one of fibrate compounds (Diabetes., 46, 348 (1997)).

Therefore, agonists that activate PPAR α and PPAR α regulators that promote expression of PPAR α protein itself are useful as hypolipidemic agents and agents for treatment of hyperlipidemia, and are expected to have HDL cholesterol level-elevating effect, LDL cholesterol and/or VLDL cholesterol levels-lowering effect, inhibition on the progress of atherosclerosis and anti-obese effect. Therefore, they are thought to be hopeful agents for the treatment and/or prevention of diabetes as hypoglycemic agents, for the improvement of hypertension, for the relief from risk factor of syndrome X and for the prevention of occurrence of ischemic coronary diseases.

On the other hand, few reports are found on ligands that activate PPAR δ significantly or on biological activities associated with PPAR δ. PPAR δ is sometimes called PPAR δ, or it is also called NUC1 in human. Until now, as for activity of PPAR δ, it is disclosed in the specification of WO 9601430 that hNUC1B (PPAR subtype whose structure is different from that of human NUC1 in one amino acid) inhibited the transcription activities of human PPAR α and thyroid hormone receptor. Recently in the specification of WO 9728149, it was reported that the compounds, which possessed high affinity to PPAR δ protein and which could activate PPAR δ significantly (i.e. agonists) were found out and that they had HDL (high density lipoprotein) cholesterol level-elevating activity. Therefore, agonists that can activate PPAR δ are expected to have HDL cholesterol level-elevating effect, and so they are expected to be useful for the inhibition on the progress of atherosclerosis and treatment thereof, as hypolipidemic agents and hypoglycemic agents, for the treatment of hyperlipidemia, as hypoglycemic agents, for the treatment of diabetes, for the relief from risk factor of syndrome X, and for the prevention of occurrence of ischemic coronary diseases.

For example, the specification of WO9828254 discloses that a compound represented by formula (A)

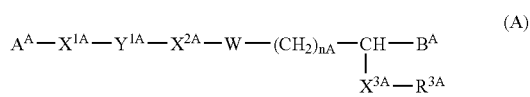

(wherein, $A^A$ is optionally substituted aryl or heterocyclic ring, $X^{1A}$ is bond, O atom, etc., $y^{1A}$ is optionally substituted C1–8 alkylene, $X^{2A}$ is bond, O atom, etc., W is optionally substituted naphthalene, etc., $B^A$ is carboxyl, etc., $X^{3A}$ is O atom, etc., $R^{3A}$ is optionally substituted C1–8 alkyl, etc., nA is integer of 1–4.)

or a salt thereof has a hypoglycemic activity and a hypolipidemic activity (necessary parts were extracted from the description of groups).

The specification of WO9911255 disclose that a compound of represented by formula (B)

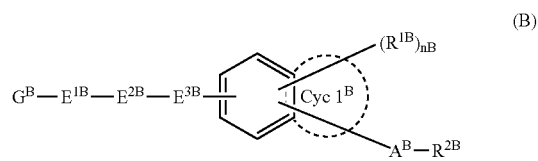

(wherein, $R^{1B}$ is C1–8 alkyl, etc., $R^{2B}$ is —COOR$^{3B}$ (in which $R^{3B}$ is hydrogen, or C1–4 alkyl.), $A^B$ is C1–8 alkylene, etc., $G^B$ is carbocyclic ring, or hetero ring (the above carbocyclic ring and hetero ring is optionally substituted by C1–8 alkyl, etc.), $E^{1B}$ is C1–8 alkylene, etc., $E^{2B}$ is —O—, etc., $E^3B$ is bond, etc., Cyc$^{1B}$ is saturated, partially saturated or unsaturated carbocyclic ring, etc.) or a salt thereof has a modulating activity of peroxisome proliferator activated receptor (necessary parts were extracted from the description of groups).

Also, in Example 3(35) in the above specification, the compound of formula (B-1) is disclosed.

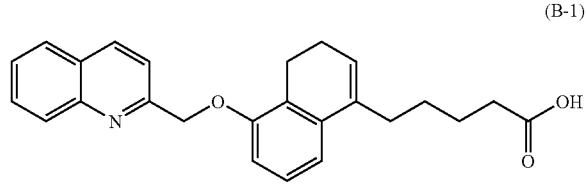

DISCLOSURE OF THE INVENTION

In order to find a compound having a PPAR modulating activity, the present inventors have conducted intensive studies and found, as a result, that the objects can be accomplished by the compound represented by formula (I), and thus the present invention has been accomplished.

The present invention relates to (1) A dihydronaphthalene derivative compound represented by formula (I)

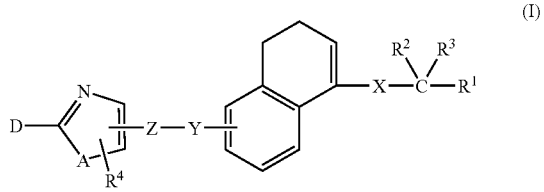

(wherein X represents (1) bond, or (2)C1–4 alkylene,

Y represents (1) —O—, or (2) —S—,

Z represents C1–4 alkylene,

A represents (1) —O—, or (2) —S—, $R^1$ represents (1) COOR$^5$, (2) CONH$_2$, (3) CONHOH, (4) CH$_2$OH, (5) CHO, (6) 1H-tetrazol-5-yl, or (7) 3,5-dioxoisooxazolin-4-yl, $R^5$ represents (1) hydrogen, or (2)C1–8 alkyl, $R^2$ and $R^3$ each independently represents (1) hydrogen, (2) C1–8 alkyl, (3)

C1–8 alkoxy, or (4) C1–8 alkoxy substituted by a phenyl, $R^4$ represents (1) hydrogen, or (2) C1–8 alkyl, D represents $D^1$, $D^2$, or $D^3$, $D^1$ represents

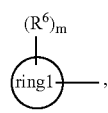

ring1 represents partially or fully optionally saturated C3–10 mono- or bi-carbocyclic aryl, D2 represents

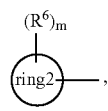

ring2 represents partially or fully optionally saturated 3–10 membered mono- or bi-heterocyclic aryl containing 1–4 hetero atom(s) selected from oxygen, nitrogen or sulfur atom, $D^3$ represents C1–8 alkyl, $R^6$ represents (1) hydrogen, (2) C1–8 alkyl, (3) nitro, (4) NR$^7$R$^8$, (5) halogen, (6) C1–8 alkoxy, (7) C1–8 alkylthio, (8) CF$_3$, (9) CF$_3$O, (10) partially or fully optionally saturated C3–10 mono- or bi-carbocyclic aryl, or (11) partially or fully optionally saturated 3–10 membered mono- or bi-heterocyclic aryl containing 1–4 hetero atom(s) selected from oxygen, nitrogen or sulfur atom, $R^7$ and $R^8$ each independently represents (1) hydrogen atom, or (2) C1-alkyl, m represents 1–3.)

or a nontoxic salt thereof, (2) a process for preparing thereof, and (3) an agent comprising thereof as an active ingredient.

DETAILED DESCRIPTION OF THE INVENTION

In the specification, the C1–8 alkyl group includes methyl, ethyl, propyl, butyl, pentyl, hexyl, heptyl, and octyl groups, and isomers thereof.

In the specification, the C1–4 alkylene group includes methylene, ethylene, trimethylene, and tetramethylene groups, and isomers thereof.

In the specification, the C1–5 alkylene group includes methylene, ethylene, trimethylene, tetramethylene, and pentamethylene groups, and isomers thereof.

In the specification, the C1–2 alkylene group includes methylene, and ethylene groups, and isomers thereof.

In the specification, the C1–3 alkylene group includes methylene, ethylene, and trimethylene groups, and isomers thereof.

In the specification, the C2–3 alkylene group includes ethylene, and trimethylene groups, and isomers thereof.

In the specification, the C1–8 alkoxy group includes methoxy, ethoxy, propoxy, butoxy, pentyloxy, hexyloxy, heptyloxy, and octyloxy groups, and isomers thereof.

In the specification, the halogen atom means a chlorine, bromine, fluorine or iodine atom.

In the specification, 1H-tetrazol-5-yl group means

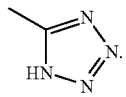

In the specification, 3,5-dioxoisooxazolidin-4-yl group means

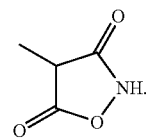

In the specification, partially or fully optionally saturated C3–10 mono- or bi-carbocyclic aryl represented by ring1 and $R^6$, means, for example, cyclopropane, cyclobutane, cyclopentane, cyclohexane, cycloheptane, cyclooctane, cyclononane, cyclodecane, cyclopropene, cyclobutene, cyclopentene, cyclohexene, cycloheptene, cyclooctene, cyclopentadiene, cyclohexadiene, cycloheptadiene, cyclooctadiene, benzene, pentalene, azulene, perhydroazulene, perhydropentalene, indene, perhydroindene, indan, naphthalene, tetrahydronaphthalene, perhydronaphthalene, etc.

In the specification, among partially or fully optionally saturated 3–10 membered mono- or bi-heterocyclic aryl containing 1–4 hetero atom(s) selected from oxygen, nitrogen or sulfur atom, 3–10 membered mono- or bi-heterocyclic aryl containing 1–4 hetero atom(s) selected from oxygen, nitrogen or sulfur atom means, for example, pyrrole, imidazole, triazole, tetrazole, pyrazole, pyridine, pyrazine, pyrimidine, pyridazine, azepine, diazepine, furan, pyran, oxepine, thiophene, thiine, thiepin, oxazole, isoxazole, thiazole, isothiazole, furazan, oxadiazole, oxazine, oxadiazine, oxazepine, oxadiazepine, thiadiazole, thiazine, thiadiazine, thiazepine, thiadiazepine, indole, isoindole, indolizine, benzofuran, isobenzofuran, benzothiophene, isobenzothiophene, dithianaphthalene, indazole, quinoline, isoquinoline, quinolizine, purine, phthalazine, pteridine, naphthyridine, quinoxaline, quinazoline, cinnoline, benzoxazole, benzothiazole, benzimidazole, chromene, benzofurazan, benzothiadiazole, benzotriazole, etc.

Also, partially or fully saturated 3–10 membered mono- or bi-heterocyclic aryl containing 1–4 hetero atom(s) selected from oxygen, nitrogen or sulfur atom, means, aziridine, azetidine, pyrroline, pyrrolidine, imidazoline, imidazolidine, triazoline, triazolidine, tetraazoline, tetraazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, oxirane, oxetane, dihydrofuran, tetrahydrofuran, dihydropyran, tetrahydropyran, dihydrooxepine, tetrahydrooxepine, perhydrooxepine, thiirane, thietane, dihydrothiophene, tetrahydrothiophene, dihydrothiin (dihydrothiopyran), tetrahydrothiin (tetrahydrothiopyran), dihydrothiepin, tetrahydrothiepin, perhydrothiepin, dihydrooxazole, tetrahydrooxazole (oxazolidine), dihydroisoxazole, tetrahydroisoxazole (isooxazolidine), dihydrothiazole, tetrahydrothiazole (thiazolidine), dihydroisothiazole, tetrahydroisothiazole (isothiazolidine), dihydrofurazan, tetrahydrofurazan, dihydrooxadiazole, tetrahydrooxadiazole (oxadiazolidine), dihydrooxazine, tetrahydrooxazine, dihydrooxadiazine, tetrahydrooxadiazine, dihydrooxazepine, tetrahydrooxazepine, perhydrooxazepine, dihydrooxadiazepine, tetrahydrooxadiazepine, perhydrooxadiazepine, dihydrothiadiazole, tetrahydrothiadiazole (thiadiazolidine), dihydrothiazine, tetrahydrothiazine, dihydrothiadiazine, tetrahydrothiadiazine, dihydrothiazepine, tetrahydrothiadiazepine, perhydrothiazepine, dihydrothiadiazepine, tetrahydrothiadiazepine, perhydrothiadiazepine, morpholine, thiomorpholine, oxathiane, indoline, isoindoline, dihydrobenzofuran, perhydrobenzofuran, dihydroisobenzofuran, perhydroisobenzofuran, dihydrobenzothiophene, perhydrobenzothiophene, dihydroisobenzothiophene, perhydroisobenzothiophene, dihydroindazole, perhydroindazole, dihydroquinoline, tetrahydroquinoline, perhydroquinoline, dihydroisoquinoline, tetrahydroisoquinoline, perhydroisoquinoline, dihydrophthalazine, tetrahydrophthalazine, perhydrophthalazine, dihydronaphthyridine, tetrahydronaphthyridine, perhydronaphthyridine, dihydroquinoxaline, tetrahydroquinoxaline, perhydroquinoxaline, dihydroquinazoline, tetrahydroquinazoline, perhydroquinazoline, dihydrocinnoline, tetrahydrocinnoline, perhydrocinnoline, benzoxathiane, dihydrobenzoxazine, dihydrobenzothiazine, pyrazinomorpholine, dihydrobenzoxazole, perhydrobenzoxazole, dihydrobenzothiazole, perhydrobenzothiazole, dihydrobenzimidazole, perhydrobenzimidazole, dioxolane, dioxane, dithiolane, dithiane, dioxaindan, benzodioxane, chromane, benzodithiolane, benzodithiane, etc.

In the present invention, PPAR regulator includes all the regulators of PPAR α, γ, δ, α+γ, α+δ, γ+δ and α+γ+δ. Preferable regulatory fashion is, PPAR α regulator, PPAR γ regulator, PPAR δ regulator, PPAR α+γ regulator, PPAR α+δ regulator, more preferably PPAR α+γ regulator. PPAR regulator also includes PPAR agonist and PPAR antagonist, preferably PPAR agonist, more preferably PPAR α agonist, PPAR γ agonist, PPAR δ agonist, PPAR α+γ agonist or PPAR α+δ agonist, particularly preferably PPAR α+γ agonist.

Unless otherwise specified, all isomers are included in the present invention. For example, alkyl, alkoxy and alkylene group includes straight or branched ones. In addition, isomers on double bond, ring, fused ring (E—, Z—, cis-, trans-isomer), isomers generated from asymmetric carbon atom(s) (R—, S—, α-, β-isomer, enantiomer, diastereomer), optically active isomers (D-, L-, d-, I-isomer), polar compounds generated by chromatographic separation (more polar compound, less polar compound), equilibrium compounds, mixtures thereof at voluntary ratios and racemic mixtures are also included in the present invention.

According to the present invention, unless otherwise indicated and as is apparent for those skilled in the art, symbol 

indicates that it is bound to the opposite side of the sheet (namely α-configuration), symbol 

indicates that it is bound to the front side of the sheet (namely β-configuration), symbol 

indicates that it is α-, β- or a mixture thereof, and symbol 

indicates that it is a mixture of α-configuration and β-configuration.

The compound of the present invention can be converted into a nontoxic salt by known methods.

A nontoxic salt is preferably pharmaceutically acceptable and water-soluble.

A nontoxic salt means, for example, salts of alkali metals (e.g., potassium, sodium, lithium, etc.), salts of alkaline earth metals (e.g., calcium, magnesium, etc.), ammonium salts (e.g., tetramethylammonium, tetrabutylammmonium, etc.), salts of organic amines (e.g., triethylamine, methylamine, dimethylamine, cyclopentylamine, benzylamine, phenethylamine, piperidine, monoethanolamine, diethanolamine, tris(hydroxymethyl)methylamine, lysine, arginine, N-methyl-D-glucamine, etc.), acid-addition salts (e.g., inorganic acid salts (e.g., hydrochloride, hydrobromate, hydroiodate, sulfate, phosphate, and nitrate, etc.), organic acid salts (e.g., acetate, trifluoroacetate, lactate, tartrate, oxalate, fumarate, maleate, benzoate, citrate, methane sulfonate, ethane sulfonate, benzene sulfonate, toluene sulfonate, isethionate, glucuronate, gluconate, etc.), etc.

Furthermore, a solvate of compound of the present invention represented by formula (I), and the above alkai (earth) metals, ammmonium, organic amines and acid-addition salts thereof, is included in the present invention.

The solvate is preferably nontoxic and water-soluble. Appropriate solvates means, for example, solvates such as water, an alcohol solvent (e.g., ethanol, etc.), etc.

In the present invention, X is preferably bond or C1–4 alkylene group, and more preferably C1–4 alkylene group. The C1–4 alkylene is preferably methylene (—CH$_2$—), ethylene (—(CH$_2$)$_2$—) or trimethylene (—(CH$_2$)$_3$—), and more preferably methylene (—CH$_2$—).

In the present invention, Y is preferably —O— group or —S— group, and more preferably —O— group.

In the present invention, Z is preferably methylene (—CH$_2$)— or ethylene (—(CH$_2$)$_2$—), and more preferably ethylene (—(CH$_2$)$_2$—).

In the present invention, $R^1$ is preferably COOR$^5$ group, CH$_2$OH group, 1H-tetrazol-5-yl group, and more preferably COOR$^5$ group.

In the present invention, $R^2$ and $R^3$ are preferably hydrogen atom, C1–8 alkyl or C1–8 alkoxy, and more preferably hydrogen atom.

In the present invention, $R^4$ is preferably C1–8 alkyl group, and more preferably methyl group.

In the present invention, D is preferably $D^1$ or $D^2$, and more preferably $D^1$.

In the present invention, A is preferably —O— group or —S— group, and more preferably —O— group.

In the present invention, ring1 is preferably partially or fully optionally saturated C3–7 mono-carbocyclic aryl, and more preferably C3–7 mono-carbocyclic aryl, and furthermore preferably benzene.

In the present invention, ring2 is preferably partially or fully optionally saturated 3–10 membered mono- or bi-heterocyclic aryl containing 1–2 hetero atom(s) selected from oxygen, nitrogen or sulfur atom, and more preferably partially or fully optionally saturated 3–7 membered mono-heterocyclic aryl containing 1–2 hetero atom(s) selected from oxygen, nitrogen or sulfur atom, and furthermore preferably pyridine, tetrahydropyridine, piperidine, piperazine, thiomorpholine, morpholine, pyrazole, pyrazine, 1,3-dioxaindan.

Among the compounds represented by formula (I), preferred compounds are compounds represented by formula (I-A)

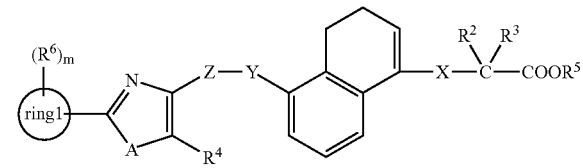

(I-A)

(wherein all symbols have the same meanings as described above.), compounds represented by formula (I-B)

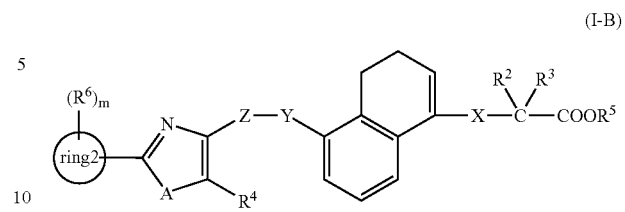

(I-B)

(wherein all symbols have the same meanings as described above.), and compounds represented by formula (I-C)

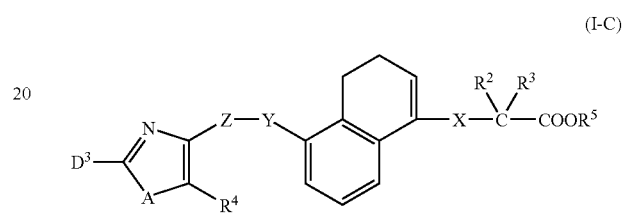

(I-C)

(wherein all symbols have the same meanings as described above.).

Concrete compounds of the present invention include compounds shown in Tables 1 to 13, compounds described in Examples, and nontoxic salts thereof.

In each Table, Me represents methyl group, Et represents ethyl group, Pr represents propyl group, i-Pr represents isopropyl group, t-Bu represents tertiarybutyl group, and other symbols have the same meanings as described above.

TABLE 1

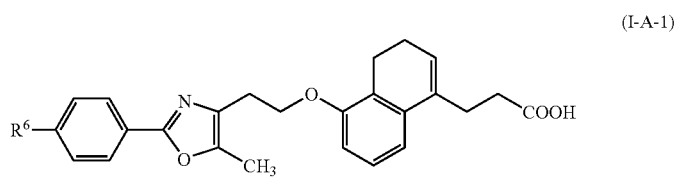

(I-A-1)

| No | $R^6$ |
|---|---|
| 1 | H |
| 2 | Me |
| 3 | Pr |
| 4 | i-Pr |
| 5 | t-Bu |
| 6 | Cl |
| 7 | ![phenyl] |
| 8 | ![dimethylpyrazole] |

TABLE 1-continued
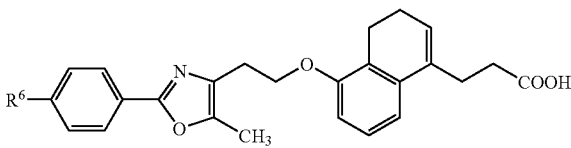
(I-A-1)
| No | R⁶ |
|----|----|
| 9 | 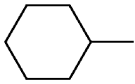 |
| 10 | 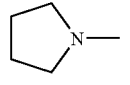 |
| 11 | 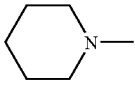 |
| 12 | OCF₃ |
| 13 | CF₃ |
| 14 | NO₂ |
| 15 | NMe₂ |
| 16 | OMe |
| 17 | SMe |
| 18 | 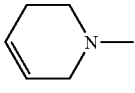 |
| 19 | 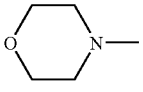 |
| 20 | 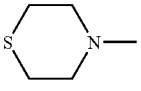 |
| 21 | 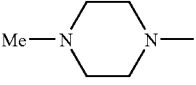 |
| 22 | Me—N⟨ ⟩N— |
TABLE 2
(I-A-2)
| No | R⁶ |
|----|----|
| 1 | H |
| 2 | Me |
| 3 | Pr |
| 4 | i-Pr |
| 5 | t-Bu |
| 6 | Cl |

TABLE 2-continued
(I-A-2)
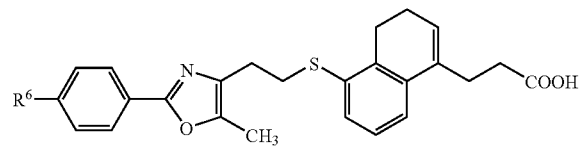
| No | R⁶ |
|----|-----|
| 7 | 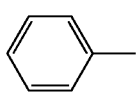 |
| 8 | 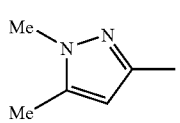 |
| 9 | 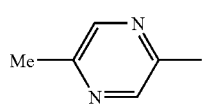 |
| 10 | 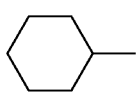 |
| 11 | 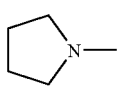 |
| 12 | OCF₃ |
| 13 | CF₃ |
| 14 | NO₂ |
| 15 | NMe₂ |
| 16 | OMe |
| 17 | SMe |
| 18 | 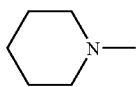 |
| 19 | 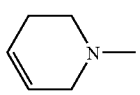 |
| 20 | 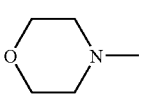 |
| 21 | 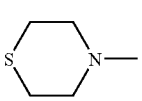 |
| 22 | 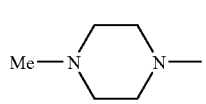 |

TABLE 3
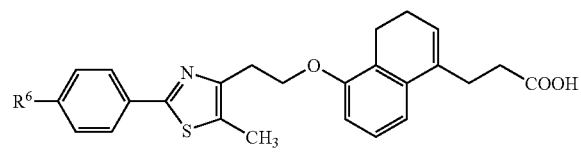
(I-A-3)
| No | R⁶ |
|----|-----|
| 1 | H |
| 2 | Me |
| 3 | Pr |
| 4 | i-Pr |
| 5 | t-Bu |
| 6 | Cl |
| 7 | (phenyl) |
| 8 | (1,5-dimethylpyrazol-3-yl) |
| 9 | (2,5-dimethylpyrazin-3-yl) |
| 10 | (cyclohexyl) |
| 11 | (pyrrolidin-1-yl) |
| 12 | OCF$_3$ |
| 13 | CF$_3$ |
| 14 | NO$_2$ |
| 15 | NMe$_2$ |
| 16 | OMe |
| 17 | SMe |
| 18 | (piperidin-1-yl) |
| 19 | (1,2,3,6-tetrahydropyridin-1-yl) |
| 20 | (morpholin-4-yl) |
| 21 | (thiomorpholin-4-yl) |
| 22 | (4-methylpiperazin-1-yl) |

TABLE 4
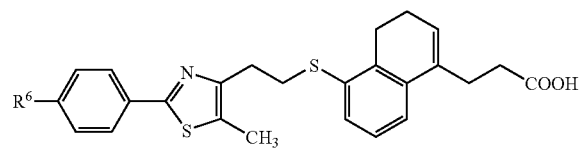
(I-A-4)
| No | R⁶ |
|----|-----|
| 1 | H |
| 2 | Me |
| 3 | Pr |
| 4 | i-Pr |
| 5 | t-Bu |
| 6 | Cl |
| 7 | (phenyl) |
| 8 | (1,5-dimethylpyrazol-3-yl) |
| 9 | (2,5-dimethylpyrazin-yl) |
| 10 | (cyclohexyl) |
| 11 | (pyrrolidin-1-yl) |
| 12 | OCF$_3$ |
| 13 | CF$_3$ |
| 14 | NO$_2$ |
| 15 | NMe$_2$ |
| 16 | OMe |
| 17 | SMe |
| 18 | (piperidin-1-yl) |
| 19 | (1,2,3,6-tetrahydropyridin-1-yl) |
| 20 | (morpholin-4-yl) |
| 21 | (thiomorpholin-4-yl) |
| 22 | (4-methylpiperazin-1-yl) |

TABLE 5
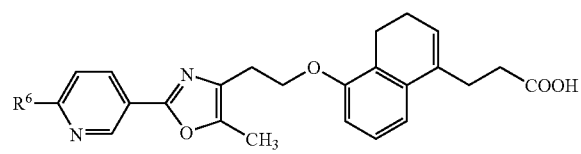
(I-B-1)
| No | R⁶ |
|---|---|
| 1 | H |
| 2 | Me |
| 3 | Pr |
| 4 | i-Pr |
| 5 | t-Bu |
| 6 | Cl |
| 7 | (phenyl) |
| 8 | (1,5-dimethylpyrazol-3-yl) |
| 9 | (2,5-dimethylpyrazin-3-yl) |
| 10 | (cyclohexyl) |
| 11 | (pyrrolidin-1-yl) |
| 12 | OCF₃ |
| 13 | CF₃ |
| 14 | NO₂ |
| 15 | NMe₂ |
| 16 | OMe |
| 17 | SMe |
| 18 | (piperidin-1-yl) |
| 19 | (1,2,3,6-tetrahydropyridin-1-yl) |
| 20 | (morpholin-4-yl) |
| 21 | (thiomorpholin-4-yl) |
| 22 | (4-methylpiperazin-1-yl) |

TABLE 6
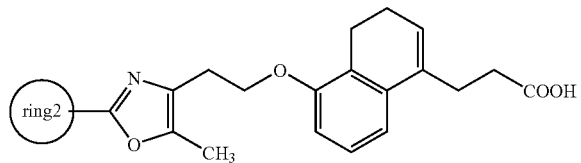
(I-B-2)
| No | ring2 |
|----|-------|
| 1  | cyclopropyl |
| 2  | cyclohexyl |
| 3  | pyrrolidin-1-yl |
| 4  | piperidin-1-yl |
| 5  | 1,2,3,6-tetrahydropyridin-1-yl |
| 6  | morpholin-4-yl |
| 7  | thiomorpholin-4-yl |
| 8  | 4-methylpiperazin-1-yl |
| 9  | 1,5-dimethyl-1H-pyrazol-3-yl |
| 10 | 5-methylpyrazin-2-yl |
| 11 | 1,3-benzodioxol-5-yl |
| 12 | 2,2-difluoro-1,3-benzodioxol-5-yl |

TABLE 7
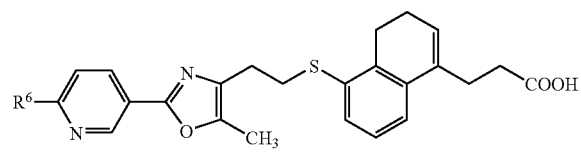
(I-B-3)
| No | R⁶ |
|----|-----|
| 1 | H |
| 2 | Me |
| 3 | Pr |
| 4 | i-Pr |
| 5 | t-Bu |
| 6 | Cl |
| 7 | ![phenyl] |
| 8 | ![1,3-dimethylpyrazol-4-yl] |
| 9 | ![2,5-dimethylpyrazin-3-yl] |
| 10 | ![cyclohexyl] |
| 11 | ![pyrrolidin-1-yl] |
| 12 | OCF₃ |
| 13 | CF₃ |
| 14 | NO₂ |
| 15 | NMe₂ |
| 16 | OMe |
| 17 | SMe |
| 18 | ![piperidin-1-yl] |
| 19 | ![tetrahydropyridin-1-yl] |
| 20 | ![morpholin-4-yl] |
| 21 | ![thiomorpholin-4-yl] |
| 22 | ![4-methylpiperazin-1-yl] |

TABLE 8
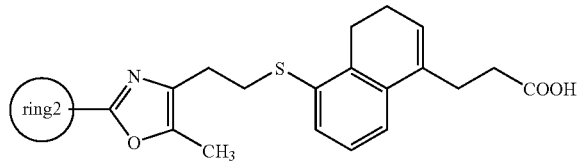
(I-B-4)
| No | ring2 |
|---|---|
| 1 | cyclopropyl |
| 2 | cyclohexyl |
| 3 | pyrrolidin-1-yl |
| 4 | piperidin-1-yl |
| 5 | 1,2,3,6-tetrahydropyridin-1-yl |
| 6 | morpholin-4-yl |
| 7 | thiomorpholin-4-yl |
| 8 | 4-methylpiperazin-1-yl |
| 9 | 1,5-dimethylpyrazol-3-yl |
| 10 | 2,5-dimethylpyrazin-yl |
| 11 | benzo[1,3]dioxol-5-yl |
| 12 | 2,2-difluorobenzo[1,3]dioxol-5-yl |

TABLE 9
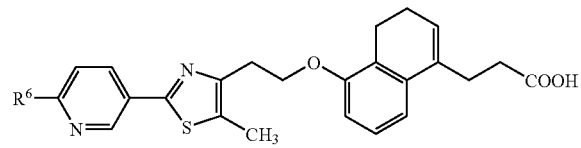
(I-B-5)
| No | R⁶ |
|---|---|
| 1 | H |
| 2 | Me |
| 3 | Pr |
| 4 | i-Pr |
| 5 | t-Bu |
| 6 | Cl |
| 7 | (phenyl) |
| 8 | (1,5-dimethylpyrazol-3-yl) |
| 9 | (2,5-dimethylpyrazin-3-yl) |
| 10 | (cyclohexyl) |
| 11 | (pyrrolidin-1-yl) |
| 12 | OCF₃ |
| 13 | CF₃ |
| 14 | NO₂ |
| 15 | NMe₂ |
| 16 | OMe |
| 17 | SMe |
| 18 | (piperidin-1-yl) |
| 19 | (1,2,3,6-tetrahydropyridin-1-yl) |
| 20 | (morpholin-4-yl) |
| 21 | (thiomorpholin-4-yl) |
| 22 | (4-methylpiperazin-1-yl) |

TABLE 10
(I-B-6)
| No | ring2 |
|---|---|
| 1 | cyclopropyl |
| 2 | cyclohexyl |
| 3 | pyrrolidin-1-yl |
| 4 | piperidin-1-yl |
| 5 | 1,2,3,6-tetrahydropyridin-1-yl |
| 6 | morpholin-4-yl |
| 7 | thiomorpholin-4-yl |
| 8 | 4-methylpiperazin-1-yl |
| 9 | 1,5-dimethyl-1H-pyrazol-3-yl |
| 10 | 5-methylpyrazin-2-yl |
| 11 | 1,3-benzodioxol-5-yl |
| 12 | 2,2-difluoro-1,3-benzodioxol-5-yl |

TABLE 11

(I-B-7)

[Structure: R⁶-pyridyl-thiazole(5-methyl)-CH₂CH₂-S-tetrahydronaphthalenyl-CH₂CH₂-COOH]

| No | R⁶ |
|----|------|
| 1 | H |
| 2 | Me |
| 3 | Pr |
| 4 | i-Pr |
| 5 | t-Bu |
| 6 | Cl |
| 7 | phenyl |
| 8 | 1,3-dimethylpyrazol-5-yl (Me, Me) |
| 9 | methylpyrazinyl (Me) |
| 10 | cyclohexyl |
| 11 | N-methylpyrrolidinyl |
| 12 | OCF₃ |
| 13 | CF₃ |
| 14 | NO₂ |
| 15 | NMe₂ |
| 16 | OMe |
| 17 | SMe |
| 18 | N-piperidinyl |
| 19 | N-tetrahydropyridinyl |
| 20 | morpholinyl |
| 21 | thiomorpholinyl |
| 22 | N-methylpiperazinyl |

TABLE 12

(I-B-8)

[Structure: ring2-thiazole(5-methyl)-CH₂CH₂-S-tetrahydronaphthalenyl-CH₂CH₂-COOH]

| No | ring2 |
|----|-------|
| 1 | cyclopropyl |
| 2 | cyclohexyl |
| 3 | pyrrolidinyl |
| 4 | piperidinyl |
| 5 | tetrahydropyridinyl |
| 6 | morpholinyl |
| 7 | thiomorpholinyl |
| 8 | N-methylpiperazinyl |
| 9 | 1,3-dimethylpyrazol-5-yl (Me, Me) |
| 10 | methylpyrazinyl (Me) |
| 11 | benzo[1,3]dioxol-5-yl |
| 12 | 2,2-difluorobenzo[1,3]dioxol-5-yl |

TABLE 13

(I-C-1)

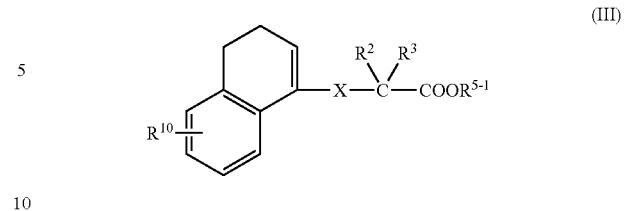

| No. | D$^1$ | A | |
|---|---|---|---|
| 1 | Me | —O— | —O— |
| 2 | Et | —O— | —O— |
| 3 | Pr | —O— | —O— |
| 4 | i-Pr | —O— | —O— |
| 5 | t-Bu | —O— | —O— |
| 6 | Me | —O— | —S— |
| 7 | Et | —O— | —S— |
| 8 | Pr | —O— | —S— |
| 9 | i-Pr | —O— | —S— |
| 10 | t-Bu | —O— | —S— |
| 11 | Me | —S— | —O— |
| 12 | Et | —S— | —O— |
| 13 | Pr | —S— | —O— |
| 14 | i-Pr | —S— | —O— |
| 15 | t-Bu | —S— | —O— |
| 16 | Me | —S— | —S— |
| 17 | Et | —S— | —S— |
| 18 | Pr | —S— | —S— |
| 19 | i-Pr | —S— | —S— |
| 20 | t-Bu | —S— | —S— |

(1) Among the compounds of the present invention represented by formula (I), a compound in which R$^1$ represents a COOR$^5$ group, and R$^5$ represents C1–8 alkyl group, i.e., a compound represented by formula (IA)

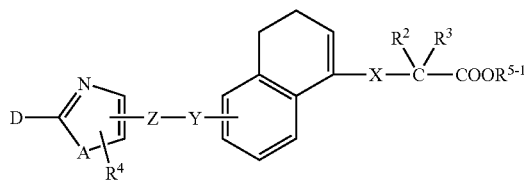

(IA)

(wherein R$^{5-1}$ represents C1–8 alkyl group, and other symbols have the same meanings as described above.) can be prepared by the following methods.

The compound represented by formula (IA) can be prepared by reacting a compound represented by formula (II)

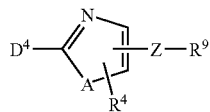

(II)

(wherein R$^9$ is represents a leaving group (e.g., a halogen atom, a mesyloxy group or a tosyloxy group, etc.), D$^4$ have the same meanings as D, with the proviso that the amino group included in the group represented by D$^4$ is protected if necessary. Other symbols have the same meanings as described above.) with a compound represented by formula (III)

(III)

(wherein R$^{10}$ represents OH group or SH group, and other symbols have the same meanings as described above.), if necessary followed by subjecting to a deprotection reaction of protecting group.

This reaction is known. For example, it is carried out at 0 to 80° C. in an organic solvent (e.g., tetrahydrofuran (THF), diethyl ether, methylene chloride, chloroform, carbon tetrachloride, pentane, hexane, benzene, toluene, dimethylformamide (DMF), dimethylsulfoxide (DMSO), hexamethylphosphoramide (HMPA), etc.) in the presence of a base (e.g., sodium hydride, potassium carbonate, triethylamine, pyridine, sodium iodide, cesium carbonate, etc.).

The deprotection reaction of these protecting groups can be carried out by the following methods.

The deprotection reaction of these protecting groups of a amino group is known, and examples include (1) a deprotection reaction under acidic conditions, (2) a deprotection reaction by hydrogenolysis, and the like.

These methods are specifically described below.

(1) The deprotection reaction under acidic conditions is carried out, for example, in an organic solvent (e.g., methylene chloride, chloroform, dioxane, ethyl acetate, anisole, methanol, ethanol, isopropylalcohol, etc.) or absence of organic solvent or an aqueous solution thereof, using an organic acid (e.g., acetic acid, trifluoroacetic acid, methanesulfonic acid, etc.), an inorganic acid (e.g., hydrochloric acid, sulfuric acid, etc.) or a mixture thereof (e.g., hydrogen bromide/acetic acid, etc.) at 0 to 100° C.

(2) The deprotection reaction by hydrogenolysis is carried out, for example, in a solvent, (e.g., an ether system (e.g., tetrahydrofuran, dioxane, dimethoxyethane, diethyl ether, etc.), an alcohol system (e.g., methanol, ethanol), a benzene system (e.g., benzene, toluene, etc.), a ketone system (e.g., acetone, methyl ethyl ketone, etc.), a nitrile system (e.g., acetonitrile, etc.), an amide system (e.g., dimethylformamide, etc.), water, ethyl acetate, acetic acid or a mixed solvent of two or more of them, etc.), in the presence of a catalyst (e.g., palladium-carbon, palladium black, palladium hydroxide, platinum oxide, Raney nickel, etc.) under ordinary or forced pressure in an atmosphere of hydrogen or in the presence of ammonium formate at 0 to 200° C.

Examples of the protecting group of an amino group include a benzyloxycarbonyl group, a t-butoxycarbonyl group, a trifluoroacetyl group, and a 9-fluorenylmethoxycarbonyl group.

The protecting groups of an amino group is not particularly limited to the above, and other groups can also be used, so long as they can be easily and selectively released. For example, those which are described by T. W. Greene in Protective Groups in Organic Synthesis, 3rd edition, Wiley, N.Y., 1999, can be used.

Although it can be easily understood by those skilled in the art, an objective compound of the present invention can be easily prepared by properly using these deprotection reactions.

Furthermore, among the compounds represented by formula (IA), a compound in which Y represents —O— group, i.e., a compound represented by formula (IA-1)

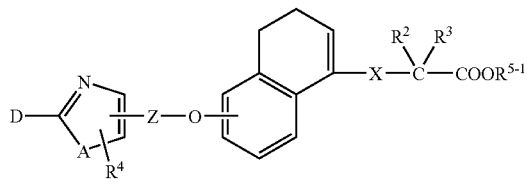
(IA-1)

(wherein all symbols have the same meanings as described above.) can be prepared by reacting a compound represented by formula (IV)

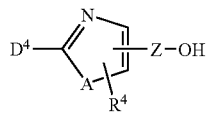
(IV)

(wherein all symbols have the same meanings as described above.) with a compound represented by formula (III-1)

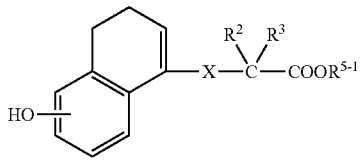
(III-1)

(wherein all symbols have the same meanings as described above.), if necessary followed by subjecting to a deprotection reaction of protecting group.

This reaction is known. For example, it is carried out by reacting with a corresponding alcohol compound in an organic solvent (e.g., dichloromethane, diethyl ether, tetrahydrofuran, acetonitrile, benzene, toluene, etc.) in the presence of an azo compound (e.g., diethyl azodicarboxylate, diisopropyl azodicarboxylate, 1,1'-(azodicarbonyl)dipiperidine, 1,1'-azobis(N,N-dimethylformamide), etc.) and a phosphine compound (e.g., triphenylphosphine, tributylphosphine, trimethylphosphine, etc.).

The deprotection reaction of a protecting group can be carried out by the methods described above.

(2) Among the compounds represented by formula (I), a compound in which $R^1$ represents COOH group, i.e., a compound represented by formula (IB)

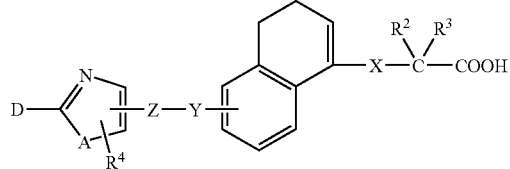
(IB)

(wherein all symbols have the same meanings as described above.) can be prepared by the following methods.

The compound represented by formula (IB) can be prepared by subjecting the above compound represented by formula (A) to a hydrolysis reaction.

The said hydrolysis reaction is known. It is carried out, for example, (1) in an organic solvent admissible with water (e.g., THF, dioxane, ethanol, methanol etc.) or mixture solvent thereof, using an aqueous solution of alkali (e.g., potassium hydroxide, sodium hydroxide, lithium hydroxide, potassium carbonate, sodium carbonate etc.), or (2) in alkanol (e.g., methanol, ethanol etc.), using the above alkali under an anhydrous condition. These reactions may be carried out at 0~100° C. normally.

Also, among the compounds represented by formula (IB), a compound in which $R^2$ represents hydrogen atom, and $R^3$ is C1–8 alkoxy group, i.e., a compound represented by formula (IB-1)

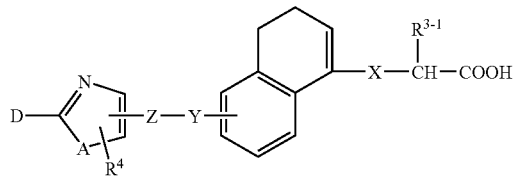
(IB-1)

(wherein $R^{3-1}$ represents C1–8 alkoxy group, and other symbols have the same meanings as described above.) can be prepared by subjecting a compound of formula (V)

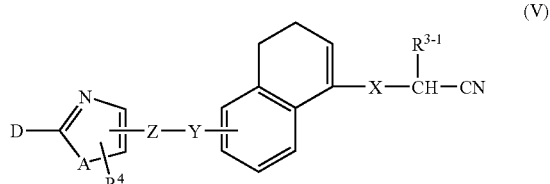
(V)

(wherein all symbols have the same meanings as described above.) to a hydrolysis reaction, if necessary followed by subjecting to a deprotection reaction of protecting group.

This hydrolysis reaction is known. It is carried out, for example, in an organic solvent admissible with water (e.g., (hydrous)methanol, dioxane, tetrahydrofuran, etc.) or mixture solvent thereof, in the presence of an aqueous solution of alkali (e.g., sodium hydroxide, potassium hydroxide, lithium hydroxide, etc.) at room temperature to reflux temperature.

The deprotection reaction of a protecting group can be carried out by the methods described above.

(3) Among the compounds represented by formula (I), a compound in which $R^1$ represents $CH_2OH$ group, i.e., a compound represented by formula (IC)

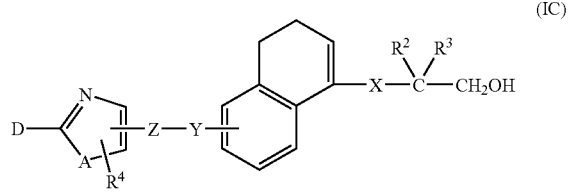

(IC)

(wherein all symbols have the same meanings as described above.) can be prepared by the following methods.

The compound represented by formula (IC) can be prepared by reduction of a compound represented by formula (VI)

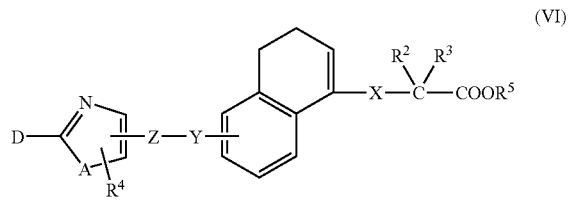

(VI)

(wherein all symbols have the same meanings as described above.), if necessary followed by subjecting to a deprotection reaction of protecting group.

This reduction is known. For example, It is carried out in an organic solvent (e.g., diethyl ether, tetrahydrofuran, toluene, methylene chloride, etc.) using a reductive agent (e.g., lithium aluminum hydride, diisobutylaluminum hydride, lithium borohydride, etc.) at −78 to 80° C.

The deprotection reaction of a protecting group can be carried out by the methods described above.

(4) Among the compounds represented by formula (I), a compound in which $R^1$ represents CHO group, i.e., a compound represented by formula (ID)

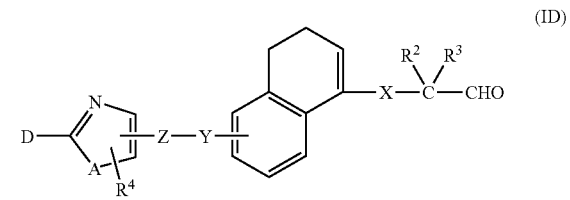

(ID)

(wherein all symbols have the same meanings as described above.) can be prepared by the following methods.

The compound represented by formula (ID) can be prepared by reduction of a compound represented by formula (VII)

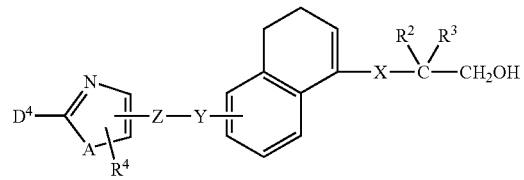

(VII)

(wherein all symbols have the same meanings as described above.), if necessary followed by subjecting to a deprotection reaction of protecting group.

This oxidation is known. For example, it includes the method
(1) by Swern oxidation,
(2) using Dess-Martin Reagent,
(3) using TEMPO Reagent.

These methods are explained as follows.

(1) Swern oxidation may be carried out, for example, by reacting oxalyl chloride with dimethylsulfoxide in an organic solvent (e.g., chloroform, methylene chloride, etc.) at −78° C., and by reacting an obtained intermediate with an alcohol compound, and then by reacting an obtained compound with a tertiary amine (e.g., triethylamine, etc.) at −78 to 20° C.

(2) The method using Dess-Martin Reagent may be carried out, for example, in an inert organic solvent (e.g. chloroform, dichloromethane, etc.), using Dess-Martin Reagent (1,1,1-triacetoxy-1,1-dihydro-1,2-benziodoxol -3-(1H)-one) at 0 to 40° C.

(3) The method using TEMPO Reagent may be carried out, for example, in an inert organic solvent (e.g., chloroform, methylene chloride, etc.) in the presence of TEMPO Reagent (2,2,6,6-tetramethyl-1-piperidinyloxy, free radical) at 20 to 60° C.

The reaction described in (1), (2) and (3) may be carried out under an inert gas (e.g. argon, nitrogen, etc.) to avoid water in order to obtain a preferable result.

As a method of oxidation, other methods, which can be oxidized alcohol to ketone easily and selectively, are also preferred, for example, Jone's oxidation, a method using pyridinium chlorochromate (PCC), a method using sulfur trioxide pyridine complex or methods described in Comprehensive Organic Transformations [Richard C. Larock, VCH Publishers, Inc., (1989) page 604–614].

The deprotection reaction of a protecting group can be carried out by the methods described above.

(5) Among the compounds represented by formula (I), a compound in which $R^1$ represents CONHOH group, i.e., a compound represented by formula (IE)

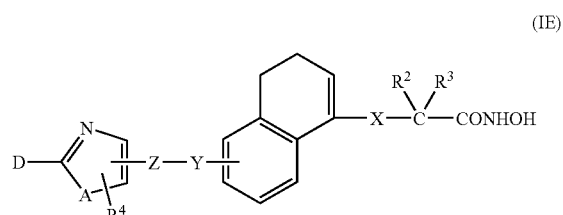

(IE)

(wherein all symbols have the same meanings as described above.) can be prepared by the following methods.

The compound represented by formula (IE) can be prepared by subjecting a compound represented by formula (VII)

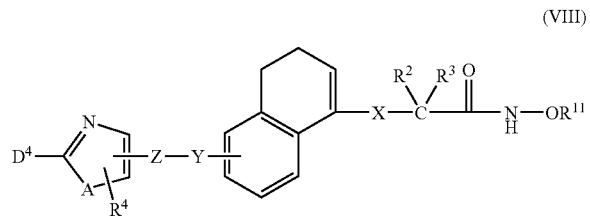

(VIII)

(wherein $R^{11}$ represents C1–8 alkyl substituted with phenyl group or C1–8 alkoxy group, and other symbols have the same meanings as described above.) to a deprotection reaction of $R^{11}$ group, if necessary followed by subjecting to a deprotection reaction of protecting group.

The deprotection reaction of $R^{11}$ group (under acidic condition or by hydrogenolysis) is known. It can be carried out by the following methods.

The deprotection reaction under acidic conditions is known. For example, it is carried out, in an organic solvent (e.g., methylene chloride, chloroform, dioxane, ethyl acetate, anisole, etc.) using an organic acid (e.g., acetic acid, trifluoroacetic acid, methanesulfonic acid, iodotrimethylsilane, etc.), an inorganic acid (e.g., hydrochloric acid, sulfuric acid, etc.) or a mixture thereof (e.g., hydrogen bromide acetic acid, etc.) at 0 to 100° C.

The deprotection reaction by hydrogenolysis is known. For example, it is carried out in a solvent, (e.g., an ether system (e.g., tetrahydrofuran, dioxane, dimethoxyethane, diethyl ether, etc.), an alcohol system (e.g., methanol, ethanol), a benzene system (e.g., benzene, toluene, etc.), a ketone system (e.g., acetone, methyl ethyl ketone, etc.), a nitrile system (e.g., acetonitrile, etc.), an amide system (e.g., dimethylformamide, etc.), water, ethyl acetate, acetic acid or a mixed solvent of two or more of them, etc.), in the presence of a hydrogenated catalyst (e.g., palladium-carbon, palladium black, palladium, palladium hydroxide, platinum oxide, nickel, Raney nickel, etc.), in the presence of an inorganic acid (e.g., hydrochloric acid, sulfuric acid, hypochlorous acid, boric acid, tetrafluoroboric acid, etc.) or an organic acid (e.g., acetic acid, p-toluenesulfonic acid, oxalic acid, tirfluoroacetic acid, formic acid, etc.) or absence thereof at 0 to 200° C. In the case that an acid is used, a salt of the acid may be used.

The deprotection reaction of a protecting group in $D^4$ group can be carried out by the methods described above.

(6) Among the compounds represented by formula (I), a compound in which $R^1$ represents 1H-tetrazol-5-yl group, i.e., a compound represented by formula (IF)

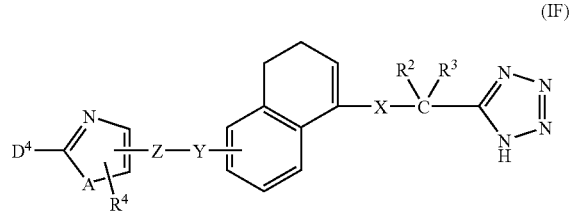

(IF)

(wherein all symbols have the same meanings as described above.) can be prepared by the following methods.

The compound represented by formula (IF) can be prepared by reacting a compound represented by formula (IX)

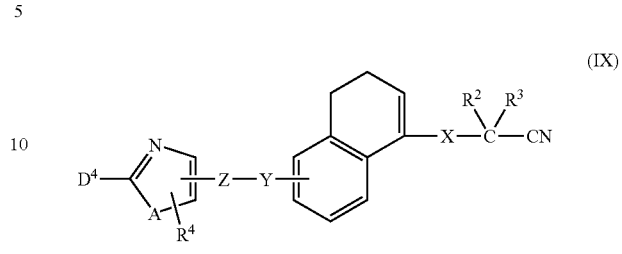

(IX)

(wherein all symbols have the same meanings as described above.) with an azido reagent, if necessary followed by subjecting to a deprotection reaction of protecting group.

This reaction is known. For example, it is carried out at 50° C. to reflux temperature in an organic solvent (e.g., toluene, benzene, etc.) using an azido reagent (e.g., azidotrimethylthin, trimethylsilyl azide, sodium azide, etc.).

The deprotection reaction of a protecting group can be carried out by the methods described above.

(7) Among the compounds represented by formula (I), a compound in which $R^1$ represents 3,5-dioxoisooxazolin-4-yl group, i.e., a compound represented by formula (IG)

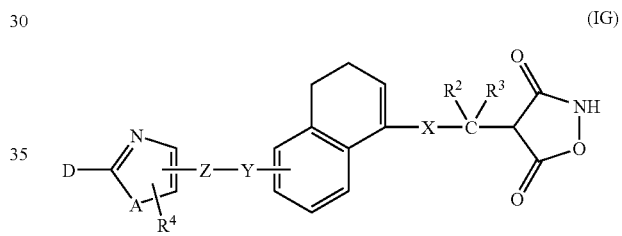

(IG)

(wherein all symbols have the same meanings as described above.) can be prepared by the following methods.

The compound represented by formula (IG) can be prepared by reacting a compound represented by formula (X)

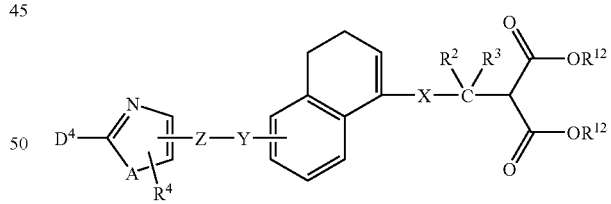

(X)

(wherein $R^{12}$ represents C1–8 alkyl group, and other symbols have the same meanings as described above.) with hydroxylamine, if necessary followed by subjecting to a deprotection reaction of protecting group.

This reaction is known. For example, it is carried out by reacting with hydroxylamine at 0 to 50° C. in an organic solvent (e.g., methanol, ethanol, etc.) in the presence of a base (e.g., sodium methylate, sodium ethylate, etc.).

The deprotection reaction of a protecting group can be carried out by the methods described above.

(8) Among the compounds represented by formula (I), a compound in which $R^1$ represents $CONH_2$ group, i.e., a compound represented by formula (IH)

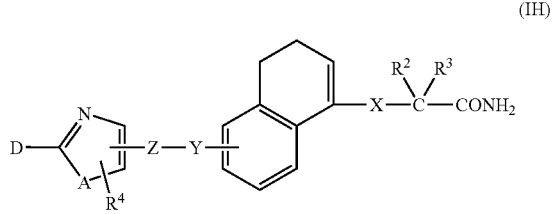

(IH)

(wherein all symbols have the same meanings as described above.) can be prepared by the following methods.

The compound represented by formula (IH) can be prepared by amidation a compound represented by formula (XI)

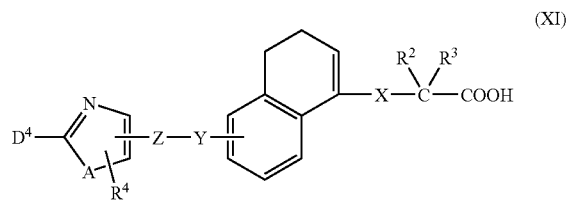

(XI)

(wherein all symbols have the same meanings as described above.) with an ammonia, if necessary followed by subjecting to a deprotection reaction of protecting group.

The amidation is known.

The amidation is known. It includes the method (1) via an acyl halide, (2) via a mixed acid anhydride, (3) using a condensing agent, etc.

These methods are explained as follows.

(1) The method via an acyl halide may be carried out, for example, by reacting carboxylic acid with an acyl halide (e.g., oxalyl chloride, thionyl chloride, etc.) in an organic solvent (e.g., chloroform, methylene chloride, diethyl ether, tetrahydrofuran, etc.) or without a solvent at −20° C. to reflux temperature. And then the obtained acyl halide derivative may be reacted with amine in an inert organic solvent (e.g., chloroform, methylene chloride, diethyl ether, tetrahydrofuran, etc.), in the presence of a tertiary amine (e.g., pyridine, triethyl amine, dimethyl aniline, dimethylaminopyridine, etc.) at 0 to 40° C.

As an alternative, it may be carried out by reacting with an acyl halide at 0 to 40° C. in an organic solvent (e.g., dioxane, tetrahydrofuran, etc.) using an alkaline aqueous solution (e.g., sodium bicarbonate, sodium hydroxide, etc.) at 0 to 40° C.

(2) The method via a mixed acid anhydride may be carried out, for example, by reacting carboxylic acid with an acyl halide (e.g., pivaloyl chloride, tosyl chloride, mesyl chloride, etc.) or an acid derivative (e.g., ethyl chloroformate, isobutyl chloroformate, etc.) in an organic solvent (e.g., chloroform, methylene chloride, diethyl ether, tetrahydrofuran, etc.) or without a solvent, in the presence of a tertiary amine (e.g., pyridine, triethylamine, dimethylaniline, dimethylaminopyridine, etc.), at 0 to 40° C. And then the obtained mixed acid anhydride derivative may be reacted with amine in an organic solvent (e.g., chloroform, methylene chloride, diethyl ether, tetrahydrofuran, etc.), at 0 to 40° C.

(3) The method using a condensing agent may be carried out, for example, by reacting carboxylic acid with amine in an organic solvent (e.g., chloroform, methylene chloride, dimethylformamide, diethyl ether, tetrahydrofuran, etc.), or a mixed solvent thereof, or without a solvent, in the presence or absence of a tertiary amine (e.g., pyridine, triethylamine, diisopropylethylamine, dimethylaniline, dimethylaminopyridine, etc.), using a condensing agent (e.g., 1, 3-dicyclohexyl carbodiimide (DCC), 1-ethyl-3-[3-(dimethylamino) propyl] carbodiimide (EDC), 1,1'-carbodiimidazole (CDI), 2-chloro-1-methylpyridinium iodide, methyl 3-methyl-2-fluoropyridinium tosylate, methanesulfonyloxybenzotriazole, 1-propanephosphonic acid cyclic anhydride (PPA), etc.), in the presence or absence of 1-hydroxybenzotiazole (HOBt), at 0 to 40° C.

The reaction described in (1), (2) and (3) may be carried out under an inert gas (e.g. argon, nitrogen) to avoid water in order to obtain a preferable result.

The deprotection reaction of a protecting group can be carried out by the methods described above.

The compounds represented by formulae (II) and (IV) are known compounds or can be prepared easily by known methods or methods described in Examples.

For example, among the compounds of formula (IV), 2-(5-methyl-2-phenyloxazol-4-yl)ethanol can be prepared by the methods described in J. Med. Chem., 35, 1853–1864 (1992).

For example, among the compounds of formula (IV), 2-(5-methyl-2-(morpholin-4-yl)oxazol-4-yl)ethanol can be prepared by the methods described in J. Med. Chem., 41, 5037–5054(1998).

The compounds represented by formulae (II), (III), (III-1), (IV), (V), (VIII), (IX) and (X) are known compounds or can be prepared easily by known methods or methods described in Examples.

For example, the compounds represented by formulae (II), (III), (III-1), (IV), (V), (VIII), (IX) and (X) can be prepared by the methods shown by the following Reaction Schemes 1 to 10.

In the reaction schemes, $R^{13}$ represents a protecting group of hydroxy group (e.g., methoxyethyl group, 2-tetrahydropyranyl group, t-butyidimethylsilyl group, acetyl group, benzyl group, 4-methoxybenzyl group, pivaloyl group, etc.), $R^{14}$ represents halogen atom, $X^1$ represents C1–5 alkylene group, $X^2$ represents C1–4 alkylene group, Me represents methyl group, i-Pr represents isopropyl group, $(CH_2O)_n$ represents paraformaldehyde, n-BuLi represents normalbutyllithium, Ph represents phenyl group, $R^{2-1}$ represents C1–8 alkyl group, $R^{3-2}$ represents C1–8 alkyl group, LDA represents lithium diisopropylamide, $R^{2-2}$ represents C1–8 alkoxy substituted with a phenyl group, p-TsOH represents paratoluenesulfonic acid, TMSCN represents trimethylsilyl cyanide, Et represents ethyl group, $Z^1$ represents bond or C1–3 alkylene group, $Z^2$ represents C1–2 alkylene group, $R^{4-1}$ represents C1–8 alkylene group, $Z^3$ represents C2–3 alkylene group, and other symbols have the same meanings as described above.

Reaction Scheme 1
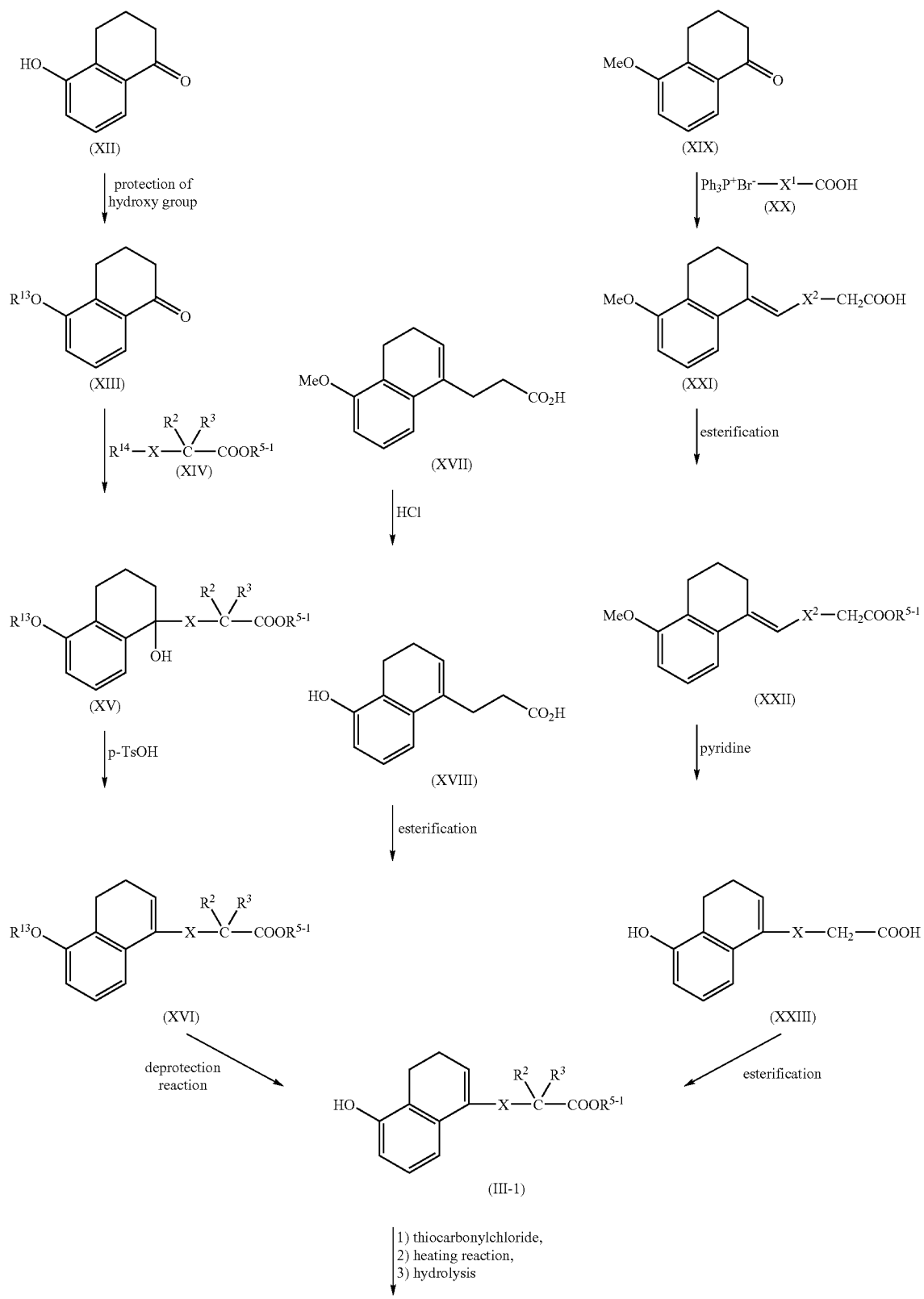

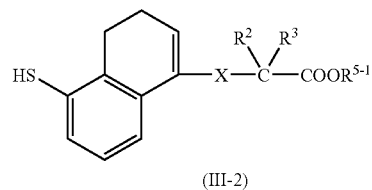
(III-2)
Reaction Scheme 2
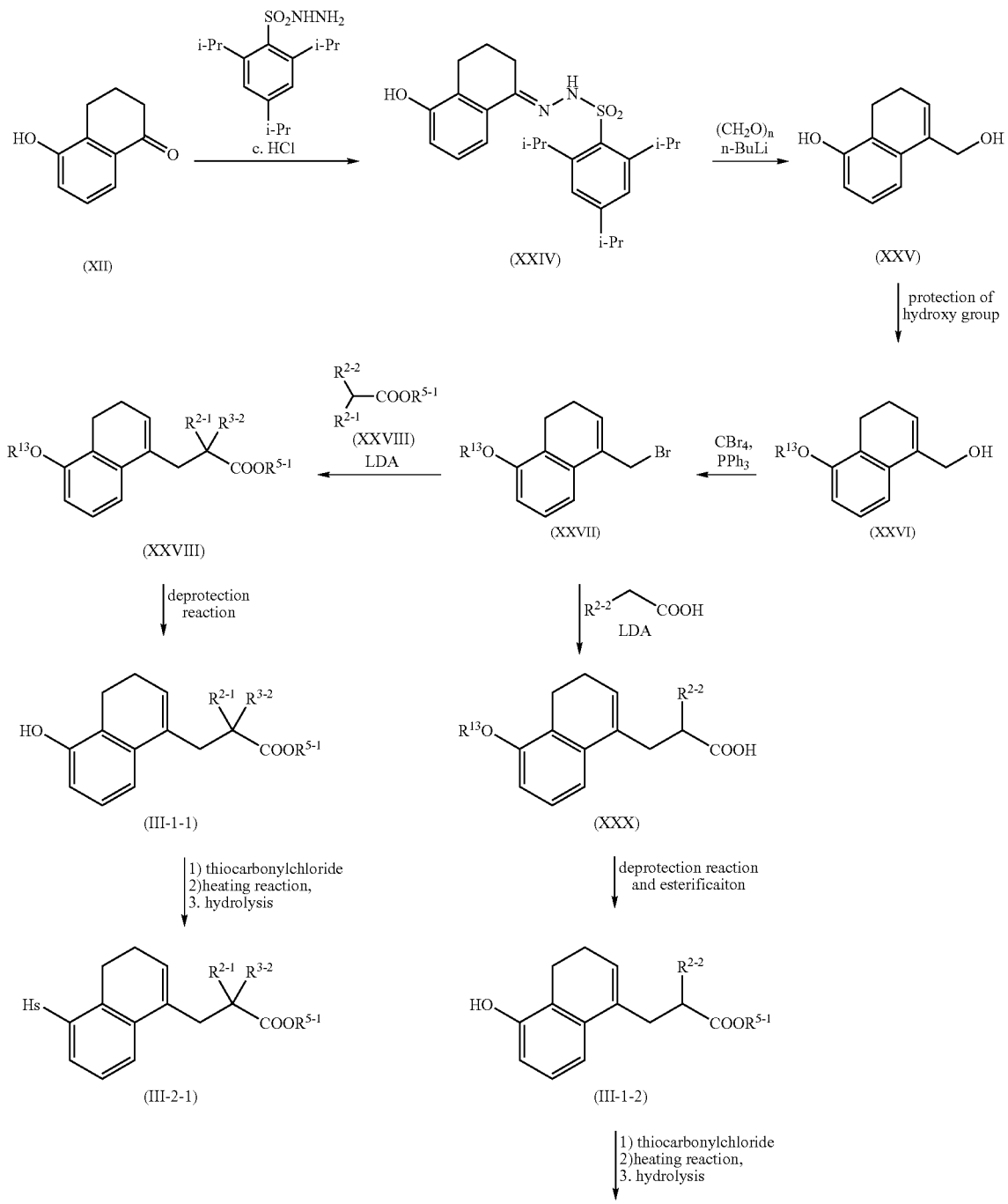

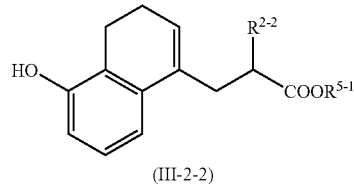
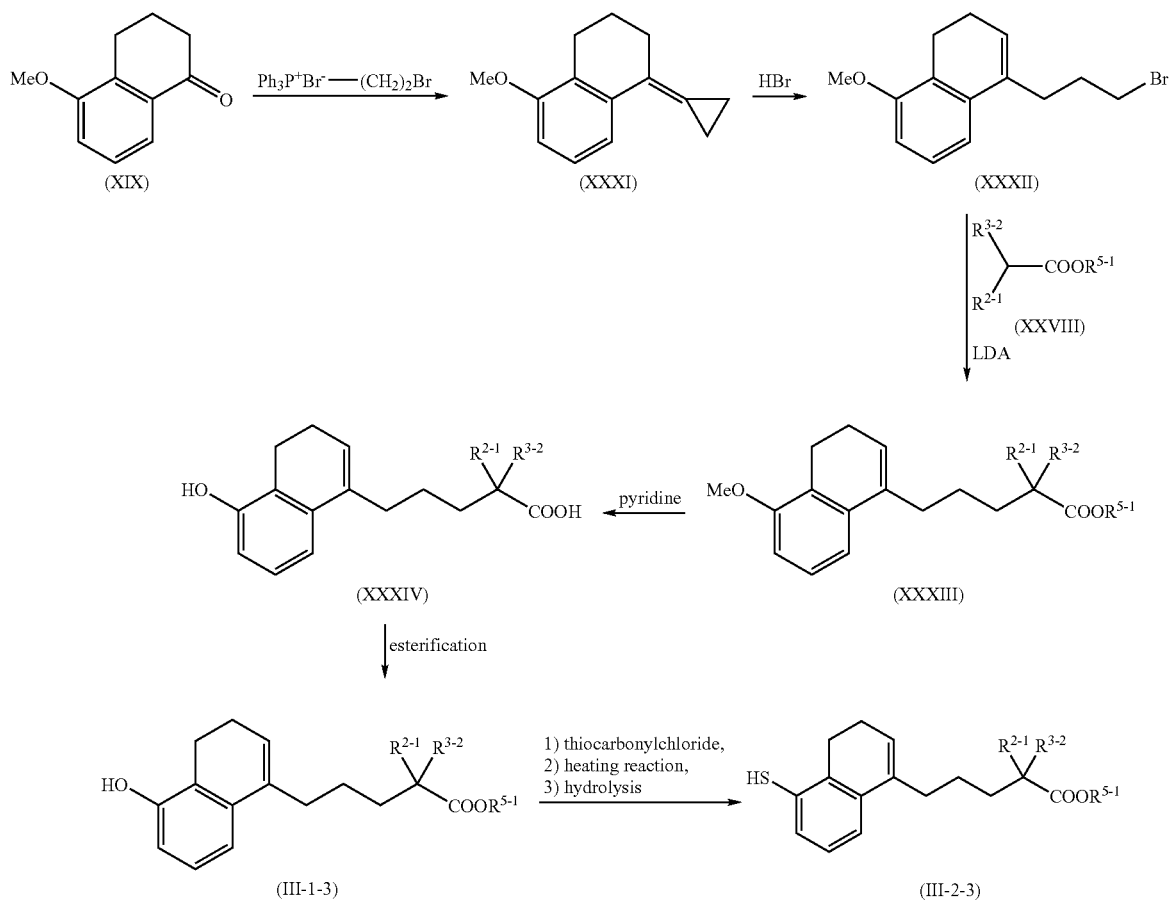
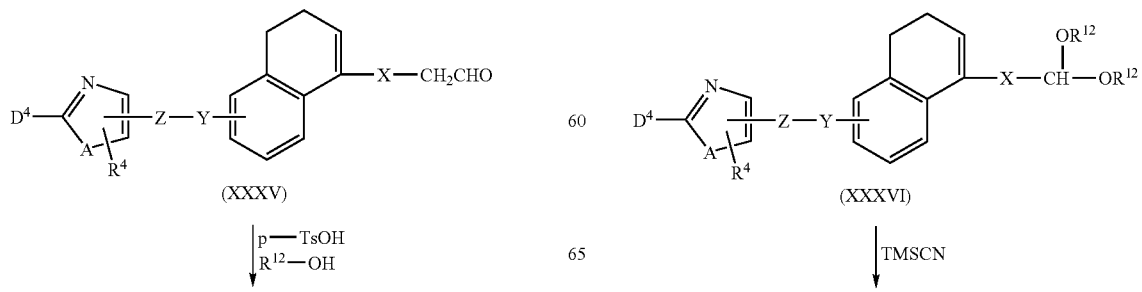

-continued
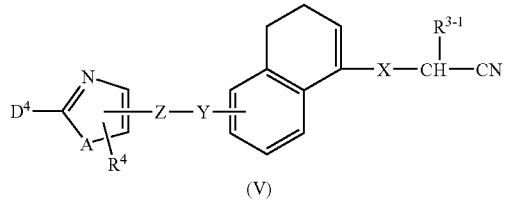
(V)
Reaction Scheme 5
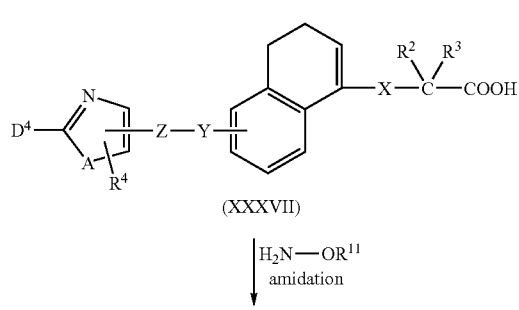
(XXXVII)
↓ H₂N—OR¹¹
amidation
-continued
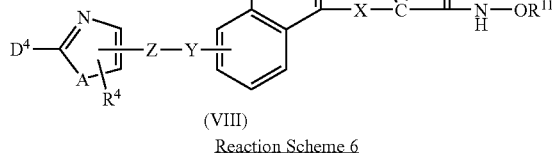
(VIII)
Reaction Scheme 6
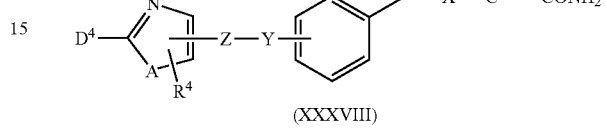
(XXXVIII)
↓ trifluoroacetic acid
pyridine
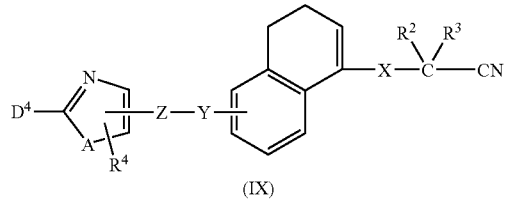
(IX)
Reaction Scheme 7
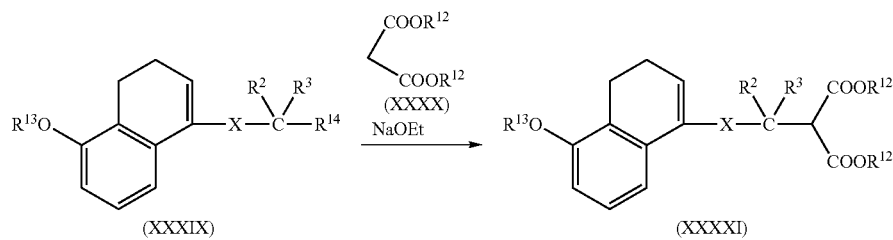
(XXXIX) → (XXXXI)
↓ deprotection reaction
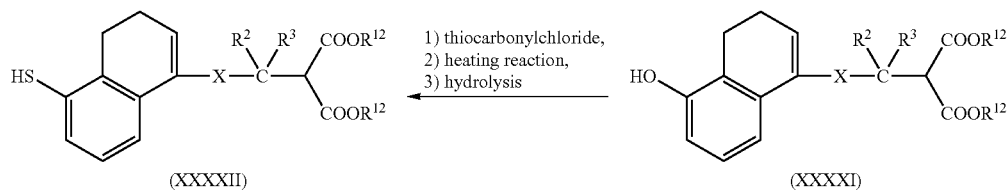
(XXXXII) ← 1) thiocarbonylchloride, 2) heating reaction, 3) hydrolysis — (XXXXI)
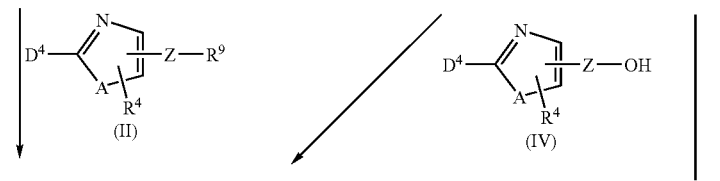
(II)    (IV)

-continued
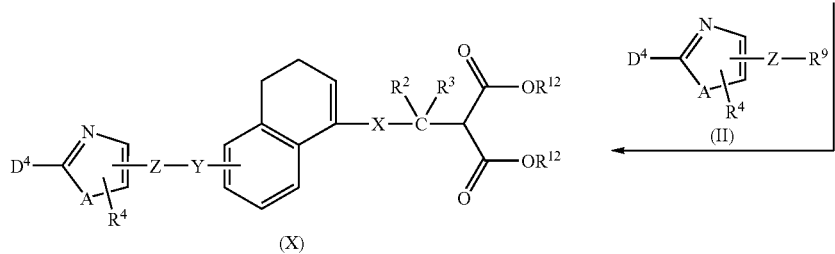
Reaction Scheme 8
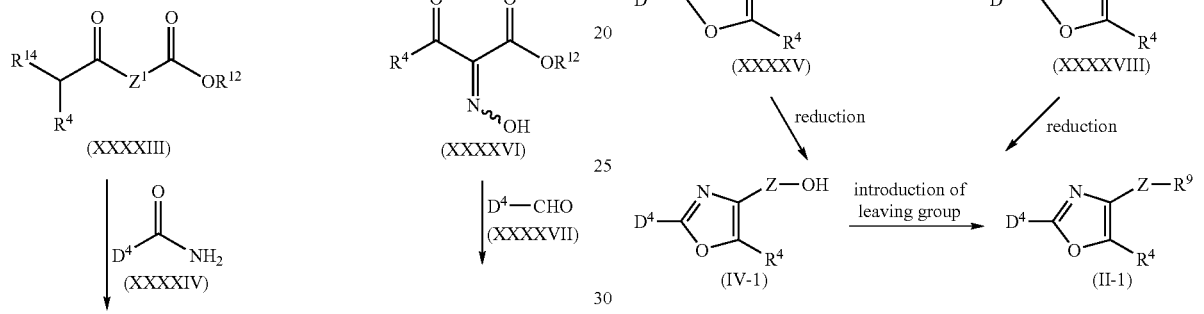
Reaction Scheme 9
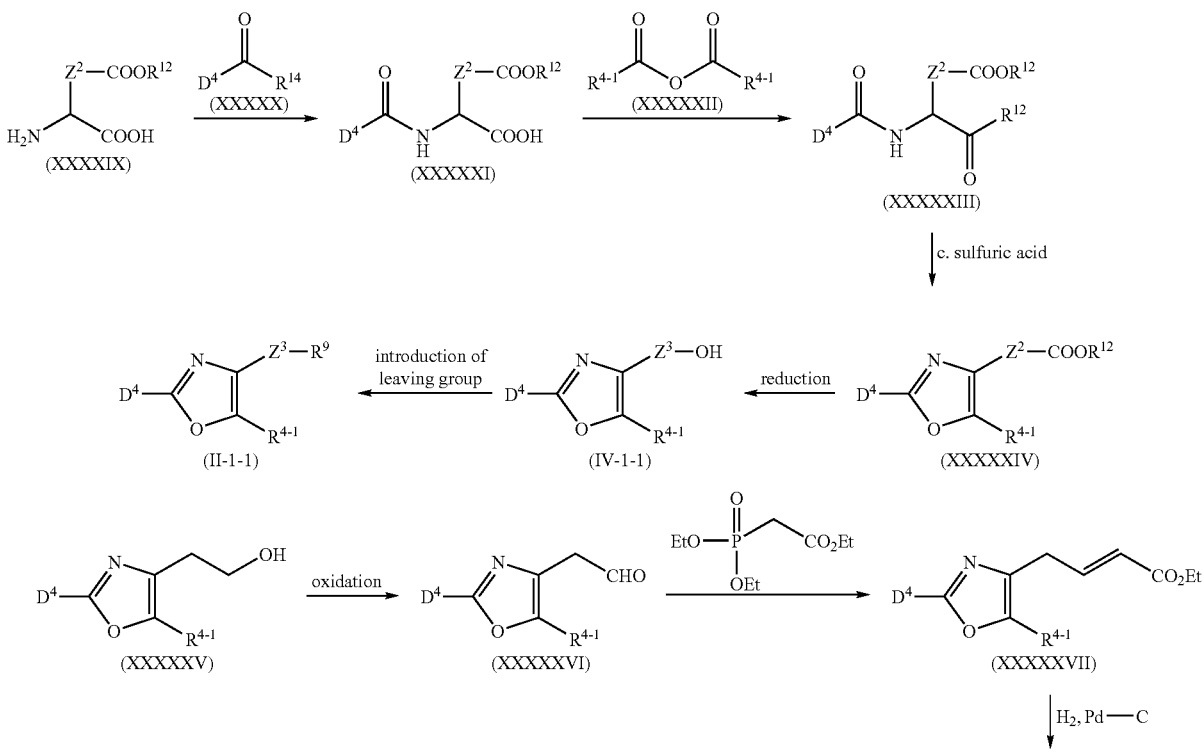

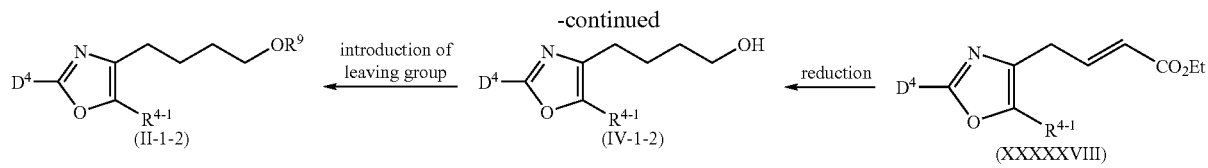

Reaction Scheme 10

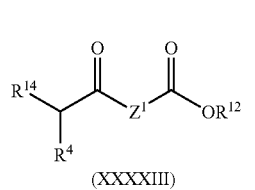
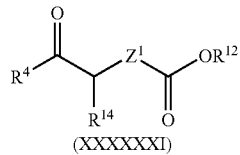

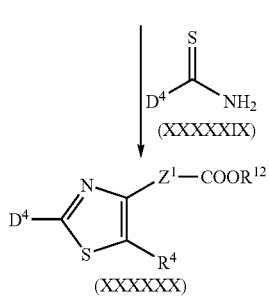
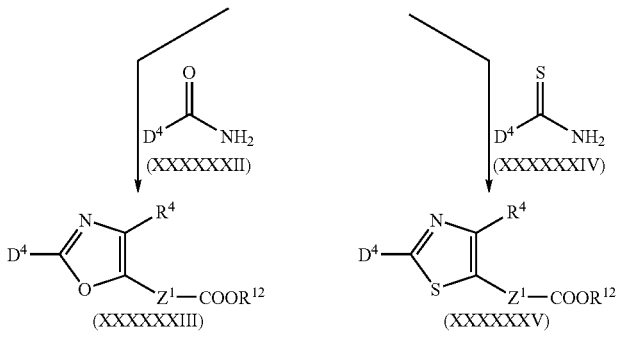

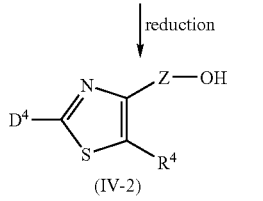
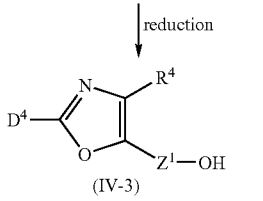
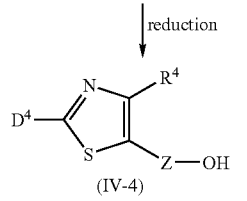

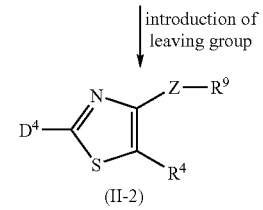
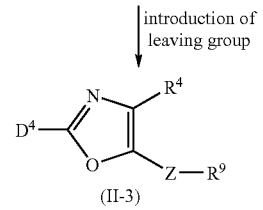
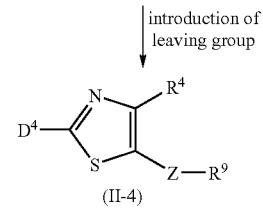

In Reaction Schemes, the compounds to be used as the starting materials represented by formulae (XII), (XIV), (XVII), (XIX), (XX), (XXVIII), (XXXV), (XXXVII), (XXXVIII), (XXXIX), (XXXX), (XXXIII), (XXXXIV), (XXXXVI), (XXXVII), (XXXXIX), (XXXXX), (XXXXXII), (XXXXXIX), (XXXXXXI), (XXXXXXII) and (XXXXXXIV) are known compounds or can be prepared easily by known methods.

In each reaction described herein, the reaction product can be purified by general purification techniques such as distillation under ordinary pressure or a reduced pressure, high performance liquid chromatography, thin layer chromatography or column chromatography using silica gel or magnesium silicate, washing and recrystallization. Purification may be carried out in each reaction or after completion of several reactions.

[Pharmacological Activity]

It was confirmed that compounds of the present invention of formula (I) has PPAR regulating activities by the following experiments.

Measurement of PPAR α Agonistic and PPAR γ Agonistic Activities (1) Preparation of Materials in Luciferase Assay Using Human PPAR α or γ

The whole operations were carried out by the basic methods in gene engineering techniques and the conventional methods in yeast One-hybrid or Two-hybrid system.

As a luciferase gene expression vector under the control of thymidine kinase (TK) promotor, luciferase structural gene was excised from PicaGene Basic Vector 2 (trade name, Toyo Ink Inc., catalogue No. 309-04821), to prepare luciferase gene expression vector pTK-Luc. under the control of TK promotor (−105/+51) as a minimum essential promotor activity from pTKβ having TK promotor (Chrontech Inc., catalogue No. 6179-1). In the upper stream of TK promotor, four times repeated UAS sequence was inserted, which is the response element of Gal4 protein, a basic transcription factor in yeast, to construct 4 X UAS-TK-Luc. as reporter gene. The following is the enhancer sequence used (Sequence No.1).

Sequence No. 1: Enhancer sequence repeating Gal4 response element four-times tande mly.

5'-T(CGACGGAGTACTGTCCTCCG)x4 AGCT-3'

A vector was prepared as described hereafter which expresses chimeric receptor protein wherein in carboxy terminus of yeast Gal4 protein DNA binding domain was fused to ligand binding domain of human PPAR α or γ. That is to say, PicaGene Basic Vector 2 (trade name, Toyo Ink Inc., catalogue No. 309-04821) was used as a basic expression vector, the structural gene was exchanged for that of chimeric receptor protein, while promotor and enhancer domains were kept as they were.

DNA encoding a fused protein composed of Gal4 DNA binding domain, the 1st to 147th amino acid sequence linked to the ligand binding domain of human PPAR α or γ in frame was inserted to the downstream of promotor/enhancer in PicaGene Basic Vector 2 (trade name, Toyo Ink Inc., catalogue No. 309-04821). Here the DNA was aligned as follows; in the amino terminus of human PPAR α or γ ligand binding domain, nuclear translocation signal originated from SV-40 T-antigen, Ala Pro Lys Lys Lys Arg Lys Val Gly (sequence No. 2) was added to make fusion protein localizing intranuclearly. On the other hand, in the carboxy terminus of them, influenza hemagglutinin epitope, Tyr Pro Tyr Asp Val Pro Asp Tyr Ala (sequence No. 3) and stop codon for translation was added in this order, to detect an expressed fused protein tagged epitope sequence.

According to the comparison of human PPAR structures described in the literatures by R. Mukherjee at al. (See J. Steroid Biochem. Molec. Biol., 51, 157 (1994)), M. E. Green et al., (See Gene Expression., 4, 281 (1995)), A. Elbrecht et al. (See Biochem Biophys. Res. Commun., 224, 431 (1996)) or A. Schmidt et al. (See Mol. Endocrinology., 6, 1634 (1992)), the portion of structural gene used as ligand binding domain of human PPAR α or γ was DNA encoding the following peptide:

human PPAR α ligand binding domain: $Ser^{167}$-$Tyr^{468}$ human PPAR γ ligand binding domain: $Ser^{176}$-$Tyr^{478}$ (each human PPAR γ1 ligand binding domain and human PPAR γ2 ligand binding domain is $Ser^{204}$-$Tyr^{506}$ which is identical sequence each other).

In order to measure basal level of transcription, an expression vector containing DNA binding domain of Gal4 protein lacking in PPAR ligand binding domain, which is exclusively encoding the 1st to 147th amino acid sequence in Gal4 protein was also prepared.

(2) Luciferase Assay Using Human PPAR α or γ

CV-1 cells used as host cells were cultured by a conventional technique. That is to say, Dulbecco's modified Eagle medium (DMEM) supplemented 10% bovine fetal serum (GIBCO BRL Inc., catalogue No. 26140-061) and 50 U/ml of penicillin G and 50 μg/ml of streptomycin sulfate were used to culture CV-1 cells under the atmosphere of 5% carbon dioxide gas at 37° C.

$2\times10^6$ cells were seeded in a 10 cm dish, and once washed with the medium without serum, followed by addition of the medium (10 ml) thereto. Reporter gene (10 μg), Gal4-PPAR expression vector (0.5 μg) and 50 μl of LipofectAMINE (GIBRO BRL Inc., catalogue No.18324-012) were well mixed and added to the culture to introduce these DNAs into the host cells. They were cultured at 37° C. for 5~6 hours, and thereto was added 10 ml of medium containing 20% of dialyzed bovine fetal serum (GIBRO BRL Inc., catalogue No. 26300-061), and then cultured at 37° C. overnight. The cells were dispersed by trypsin, and they were again seeded in 96-well plates in a density of 8000 cells/100 ml of DMEM-10% dialyzed serum/well. Several hours after the cultivation, when cells were attached to the plastic ware, then 100 μl of DMEM-10% dialyzed serum containing the compounds of the present invention, whose concentration is twice as high as the final concentration of them, was added thereto. The culture was settled at 37° C. for 42 hours and the cells were dissolved to measure luciferase activity according to manufacturer's instruction.

As to PPAR α agonistic activity, the relative activity of the compounds of the present invention (10 μM) was shown in Table 1, under the condition that luciferase activity was defined as 1.0 in case of carbacyclin (10 μM) as a positive control compound, which could activate transcription of luciferase gene significantly to PPAR α (See Eur. J. Biochem., 233, 242 (1996); Genes & Development., 10, 974 (1996)).

As to PPAR γ agonistic activity, the relative activity of the compounds of the present invention (10 μM) was shown in Table 2, under the condition that luciferase activity was defined as 1.0 in case of troglitazone (10 μM) as a positive control compound, which could activate transcription of luciferase gene significantly to PPAR γ (See Cell., 83, 863 (1995); Endocrinology., 137, 4189 (1996) and J. Med. Chem., 39, 665 (1996)) and has been already launched as hypoglycemic agent.

Furthermore, assay of each compound was carried out three times to examine its reproducibility and to confirm the dose dependent activity.

Also, the following compound described in Example 3(35) in the specification of WO9911255 was used as a comparative compound.

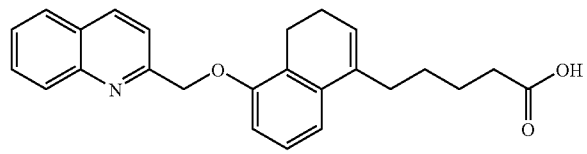

Compound Described in Example 3(35) in the Specification of WO9911255

TABLE 14

| Compound No. | Relative Activity to a positive control compound (carbacyclin = 1) |
|---|---|
| Example 2 | 0.45 |
| comprative compound | 0.01 |

TABLE 15

| Compound No. | Relative Activity to a positive control compound (troglitazone = 1) |
| --- | --- |
| Example 2 | 2.6 |
| comprative compound | 0.004 |

For example, Hypoglycemic and hypolipidemic effects of the compounds of the present invention can be measured by the following methods.

Hypoglycemic and Hypolipidemic Effects (1):

Male, 8-weeks old KKAy/Ta Jcl mice (five mice per group) are pre-breaded individually in single cages for approximately one week and provided pellet diet and tap water from bottle of feed water ad libitum. Mice are acclimatized to switch over to milled diet for three days. On the first day of the experiment (Day 0), the body weight of mice are measured. Blood samples are collected from coccygeal vein using a microcapillary to measure plasma glucose concentration. Based on plasma glucose concentration, mice are divided into some groups (five mice per group) using a stratified randomization method. The body weight of mice are measured on the morning of the next day, and from the next day for six days they are given compounds by food mixture containing 0.03% (w/w), 0.01% (w/w) or 0.003% (w/w) of the compound of the present invention or by milled diet only. On the morning of the fourth and the seventh day, body weights and food intakes of them are determined to calculate the mean administered dose. On the morning of the sixth day, blood samples were collected from coccygeal vein to measure glucose and triglyceride (TG) levels. On the seventh day after measuring body weight, blood samples are collected from abdominal vena cava under anesthetized condition by ether to determine plasma insulin, non-esterified fatty acid (NEFA), GOT and GPT levels using commercially available kits. And, the liver is removed and weighed. The total RNAs are prepared from left lobe of the liver and measured a gene expression level of bifunctional protein (hydrase-dehydrogenase, HD) by Northern blot method. Actually, there is no significant difference in the food intake between control group (milled diet only) and compounds-treated group (milled diet containing 0.03%, 0.01% or 0.003% of compounds). The calculated dose is approximately 40 mg/kg/day in the group given diet containing 0.03% of the compound.

It is suggested the possibility as an agent for preventing and/or treating of diabetes mellitus, hyperlipidemia, atherosclerosis etc., from ameliorating effects of plasma glucose, plasma insulin, NEFA or TG levels in well-fed KKAy/Ta mice. This effect is likely to be mediated through PPAR γ activation in vivo. Additionally, it is likely that an increase in liver weight and in an expression of HD mRNA depends on PPAR α activation in vivo.

Hypoglycemic and Hypolipidemic Effects (2):

Male, 8-weeks old Zucker fa/fa rats (Strain: Crj-[ZUC]-fa/fa) and healthy Zucker lean rats (Strain: Crj-[ZUC]-lean) to be contrasted are pre-breaded individually in single cages for approximately two weeks and provided pellet diet and tap water from automatic water supplying equipment ad libitum. For five days before the treatment, rats are acclimatized to oral gavage administration. During this period, a general condition of them is observed, and healthy rats with 10-weeks of age are used for experiment. The body weight of each rats are measured on the morning of the first day of experiment (Day 0) and blood samples are collected from coccygeal vein using a microcapillary to measure plasma glucose, TG, NEFA concentrations and HbA1c. Based on the HbA1c and body weight, rats are assigned to groups comprised of five animals each using a stratified randomization method. Additionally, rats are interchanged optionally to prevent the deflection of other parameters' averages between groups. The body weight of each animal was measured every morning from the day after grouping. Volumes to be administered are calculated on the basis of body weight measured on the day of administration, and oral gavage administration of compound of the present invention or vehicle only (0.5% methylcellulose) is conducted once a day for 13 days. The healthy animals (lean rats)are given vehicle only.

Food consumption is measured on the morning of Day 1, 4, 7, 10 and 13 to calculate mean food intakes. On the seventh day, blood samples are corrected from coccygeal vein using microcapillary to measure plasma glucose, TG, NEFA concentrations and HbA1c. And on the 14th day, oral glucose tolerance test (OGTT) is performed to evaluate improving effect on glucose intolerance. Rats are fasted on the previous day (Day 13) to perform OGTT. After blood samples are collected on the next day (Day 14), 40% glucose solution is loaded at a volume of 2 g/5 ml/kg per oral administration. 60 and 120 minutes after loading, blood samples are collected from coccygeal vein using microcapillary to determine plasma glucose levels.

Animals are given food after the OGTT and administered compound of the present invention on Day 15. On the morning of the 16th day after measuring body weight, blood samples are collected from abdominal vena cava under anesthetized condition by ether to determine plasma glucose, plasma insulin, TG, NEFA, GOT and GPT levels. And, the liver is removed and weighed.

It is suggested the possibility as an agent for preventing and/or treating of diabetes mellitus, hyperlipidemia, atherosclerosis etc., from ameliorating effects of plasma glucose, plasma insulin, TG, NEFA levels or HbA1c in well-fed Zucker fa/fa rats. Also, a decrease effect of fasting plasma glucose and improving effect of glucose intolerance during OGTT suggest the possibility as an agent for preventing and/or treating of diabetes mellitus. These effects are likely to be mediated through PPAR γ activation in vivo. Additionally, it is suggested that an increase in liver weight depends on PPAR α activation in vivo.

Hypoglycemic and Hypolipidemic Effects (3):

Male, 3- to 4-years old cynomolgus monkeys (Mean body weight: approximately 3 kg) to have a regal medical inspection are performed a medical inspection and acclimatized to be provided approximately 100 g of pellet diet once a day and tap water from automatic water supplying equipment ad libitum, individually in single monkey cages for more than one month. After then, animals become to take a diet within one hour.

Additionally, animals are pre-breaded for 14 days. 14 and 7 days before the treatment, the body weight are measured, and then blood samples are collected from hindlimb saphenous vein to measure hematological (red blood cells, hematocrit, hemoglobin, platelet and leukocytes) and biochemical (GOT, GPT, alkaline phosphatase, total protein, blood urea nitrogen, creatinine, creatinine kinase, total bilirubin, glucose, total cholesterol, HDL, LDL and TG) parameters. Additionally, a general condition of animals is observed during acclimatizing and pre-breeding, and healthy animals are used for experiment. Also, food consumption is measured everyday.

On the basis of body weight measured on the final day of acclimatizing period, animals are divided into some groups (three animals per group) using a stratified randomization method. On the morning of Day 1, 3, 7, 10 and 14, body weight is measured. Volumes to be administered are calculated based on the latest body weight, and oral gavage administration with compound of the present invention (3–100 mglkg/day) or vehicle alone (diluted solution) is conducted once a day for 14 days. 1, 7 and 14 days after the treatment, blood samples are collected to measure the above mentioned hematological and biochemical parameters before the administration of the compound of the present invention. It confirms that blood glucose is not changed with the compound of the present invention. Three weeks before, and 14 days after the start of treatment, blood samples are collected from hindlimb saphenous vein or antebrachial vein at 1, 2 and 4 hours after oral gavage, and also at 1, 2 and 3 hours after providing a diet, to measure plasma glucose and TG.

It is suggested the possibility as an agent for preventing and/or treating of hyperlipidemia and atherosclerosis etc., from ameliorating effects of plasma TG levels in fasted monkeys. These effects are likely to be mediated through PPAR α activation in vivo. It is also observed in suppressing effect on post-prandial TG increase. Additionally, it can be estimated whether compound have a toxicity risk from other biochemical parameters.

[Toxicity]

The toxicity of the compound represented by formula (I) of the present invention is very low so that it is considered that the compound is sufficiently safe for using as a pharmaceutical.

INDUSTRIAL APPLICABILITY

[Application to Pharmaceutical]

Since the compound represented by formula (I) of the present invention and nontoxic salt thereof have a PPAR modulating activity, it is expected to be applied as hypoglycemic agents, hypolipidemic agents, agents for preventing and/or treating of diseases associated with metabolic disorders such as diabetes, obesity, syndrome X, hypercholesterolemia and hyperlipoproteinemia etc., hyperlipidemia, atherosclerosis, hypertension, circulatory diseases, overeating, coronary heart diseases etc., HDL cholesterol-elevating agents, LDL cholesterol and/or VLDL cholesterol-lowering agents and agents for relieving risk factors of diabetes or syndrome X.

Also, since the compound represented by formula (I) of the present invention, and non-toxic salts thereof, have a PPARα agonist and/or PPAR γ agonist effect, it is expected to be applied as hypoglycemic agents, hypolipidemic agents, agents for preventing and/or treating of diseases associated with metabolic disorders such as diabetes, obesity, syndrome X, hypercholesterolemia, hyperlipoproteinemia etc., hyperlipidemia, atherosclerosis, hypertension, circulatory diseases and overeating etc., HDL cholesterol-elevating effect, LDL cholesterol and/or VLDL cholesterol-lowering effect, inhibition of progress of atherosclerosis and its treatment, and inhibitory effect against obesity. They are also expected to be useful for the treatment and/or prevention of diabetes as hypoglycemic agents, for the amelioration of hypertension, for the relief from risk factors of syndrome X, and as agents for preventing against occurrence of coronary heart diseases.

For the purpose above described, the compounds of the present invention of the formula (I) and non-toxic salts thereof may be normally administered systemically or locally, usually by oral or parenteral administration.

The compound represented by formula (I) of the present invention, and a nontoxic salt thereof is generally administered systemically or topically and orally or parenterally when it is used for the above objects.

The dosages are determined depending on age, body weight, symptom, therapeutic effect, administration route, duration of the treatment and the like. Generally, 1 mg to 1000 mg per adult is orally administered once to several times per day, or 1 mg to 100 mg per adult is parenterally administered (preferably by intravenous administration) once to several times per day, or continuously administered from vein for 1 to 24 hours per day.

Since the dose changes depending on various conditions as described above, there are cases in which doses lower than or greater than the above ranges may be used.

The compound represented by formula (I) of the present invention may be administered in the form of solid compositions, liquid compositions and other compositions for oral administration, and injections, liniments, suppositories and the like for parenteral administration.

Solid compositions for oral administration include tablets, pills, capsules, dispersible powders, granules and the like.

Capsules include hard capsules and soft capsules.

In such solid compositions, one or more active compound(s) are mixed with at least one inert diluent such as lactose, mannitol, glucose, hydroxypropyl cellulose, microcrystalline cellulose, starch, polyvinyl pyrrolidone or magnesium metasilicate aluminate. The composition may also contain additional substances other than the inert diluent, e.g., lubricants such as magnesium stearate, disintegrating agents such as cellulose calcium glycolate, stabilizing agents such as lactose, and assisting agents for dissolving such as glutamic acid and asparatic acid according to usual methods. If necessary, the tablets or pills may be coated with film of gastric- or enteric-coating agents such as sugar, gelatin, hydroxypropyl cellulose and hydroxypropyl cellulose phthalate, or be coated with two or more films. Furthermore, capsules of absorbable materials such as gelatin are included.

Liquid compositions for oral administration include pharmaceutically acceptable emulsions, solutions, syrups, elixirs and the like. In such liquid compositions, one or more active compound(s) are contained in an inert diluent commonly used (e.g., purified water, ethanol). Furthermore, such compositions may also contain auxiliary material such as wetting agents or suspending agents, sweetening agents, flavoring agents, flavoring agents, and preserving agents.

Other compositions for oral administration include sprays containing one or more active compound(s) which are prepared by known methods. Such compositions may contain stabilizing agents such as sodium hydrogen sulfate, buffering agents to give isotonicity, isotonic solutions such as sodium chloride, sodium citrate or citric acid, in addition to inert diluents. The process for preparing sprays are described in U.S. Pat. Nos. 2,868,691 and 3,095,355.

Injections for parenteral administration in the present invention include sterile aqueous or non-aqueous solutions, suspensions and emulsions. Aqueous solutions and suspensions include distilled water for injection and physiological saline. Non-aqueous solutions and suspensions include propylene glycol, polyethylene glycol, plant oil such as olive oil, alcohols such as ethanol, POLYSORBATE80 (registered trade mark), and the like. Sterile aqueous and non-aqueous solutions, suspensions and emulsions may be used as a mixture. Such compositions may further contain preserving agents, wetting agents, emulsifying agents, dispersing agents, stabilizing agents (e.g., lactose), auxiliary agents such as solubilizing auxiliary agents (e.g., glutamic acid, aspartic acid). They may be sterilized by filtration through a bacteria-retaining filter, incorporation of a sterilizing agent or irradiation. For example, they may also be manufactured in the form of sterile solid compositions which can be dissolved in sterile water or other sterile diluent for injection before use of the freeze-dried product.

Other compositions for parenteral administration include liquids for external use, endemic liniments, ointments, suppositories for intrarectal administration, pessaries for intravaginal administration and the like containing one or more active compound(s) which can be prepared by known methods.

BEST MODE FOR CARRYING OUT THE INVENTION

The present invention is explained below in detail based on Reference Examples and Examples, however, the present invention is not limited thereto.

The solvents in the parentheses show the developing or eluting solvents and the ratios of the solvents used are by volume in chromatographic separations or TLC. The solvents in the parentheses in NMR show the solvents for measurement.

REFERENCE EXAMPLE 1

3-(5-hydroxy-3,4-dihydronaphthalen-1-yl)propanoic acid

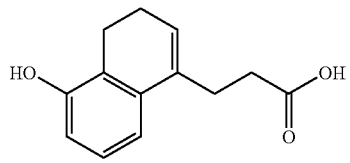

To pyridine hydrochloride (200 g), 3-(5-methoxy-3,4-dihydronaphthalen-1-yl)propanoic acid (25.1 g; known compound (see J. Chem. Soc. Perkin Trans. I., 1739–1742 (1987)) was added, followed by stirring at 180° C. for 3 hours. The reaction mixture was cooled to room temperature, and diluted with water. The aqueous layer was acidified with a concentrated hydrochloric acid. The aqueous layer was extracted with an ethyl acetate. The extract was extracted with a saturated aqueous sodium hydrogen carbonate solution. The combined aqueous layer was acidified with a concentrated hydrochloric acid, followed by extracting with an ethyl acetate. The combined organic layer was washed with a saturated saline, dried with anhydrous sodium sulfate, and concentrated under reduced pressure to thereby obtain the title compound (11.8 g) having the following physical data.

TLC: Rf 0.42 (chloroform:methanol=6:1); NMR(CDCl$_3$): δ 9.21(s, 1H), 6.98(dd, J=7.8, 7.6 Hz, 1H), 6.71(d, J=7.6 Hz, 1H), 6.70(d, J=7.8 Hz, 1H), 5.82(t, J=4.4 Hz, 1H), 2.68–2.50 (m, 4H), 2.36(m, 2H), 2.12(m, 2H).

REFERENCE EXAMPLE 2

3-(5-hydroxy-3,4-dihydronaphthalen-1-yl)propanoic acid methyl ester

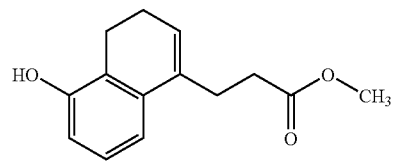

An anhydrous methanol (40 ml) was cooled to −10° C., and thionyl chloride (5.92 ml) was added dropwise thereto under argon atmosphere, followed by stirring at −10° C. for 20 minutes. To this solution, the compound (11.8 g) prepared in Reference Example 1 was added, followed by stirring at room temperature for 1 hour. The reaction mixture was concentrated under reduced pressure, followed by subjecting to azeotropy with toluene (twice). The residue was purified by silica gel column chromatography (chloroform to chloroform:methanol=50:1) to thereby obtain the title compound (10.6 g) having the following physical data.

TLC: Rf 0.72 (chloroform:methanol=10:1); NMR (CDCl$_3$): δ 7.06(dd, J=7.8, 7.6 Hz, 1H), 6.88(d, J=7.6 Hz, 1H), 6.70(d, J=7.8 Hz, 1H), 5.88(t, J=4.4 Hz, 1H), 4.93(s, 1H), 3.68(s, 3H), 2.82–2.62(m, 4H), 2.58–2.49(m, 2H), 2.26(m, 2H).

REFERENCE EXAMPLE 3

5-pivaloyloxy-1,2,3,4-tetrahydronaphthalen-1-one

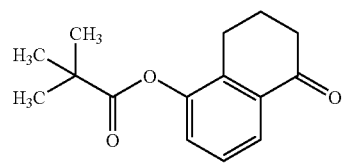

To a pyridine (180 ml) solution of 5-hydroxy-1-tetralone (30.0 g), 4-dimethylaminopyridine (1.13 g) was added, and pivaloyl chloride (25.0 ml) was added thereto under ice-cooling, followed by stirring at room temperature overnight. The reaction mixture was ice-cooled, and a concentrated hydrochloric acid was added thereto, followed by extracting with ethyl acetate. The extract was washed with water and saturated saline in this order, dried with anhydrous magnesium sulfate, and concentrated. The residue was purified by silica gel column chromatography (hexane:ethyl acetate=9:1 to 5:1) to thereby obtain the title compound (45.4 g) having the following physical data.

TLC: Rf 0.42 (hexane :ethyl acetate=5:1); NMR(CDCl$_3$): δ 7.95(dd,J=7.8, 1.4 Hz, 1H), 7.33(t, J=7.8 Hz, 1H), 7.19(dd, J=7.8, 1.4 Hz, 1H), 2.79(t, J=6.0 Hz, 2H), 2.65(dd, J=7.6, 6.0 Hz, 2H), 2.19–2.05(m, 2H), 1.40(s, 9H).

REFERENCE EXAMPLE 4

2-(1-hydroxy-5-pivaloyloxy-1,2,3,4-tetrahydronaphthalen-1-yl)acetic acid ethyl ester

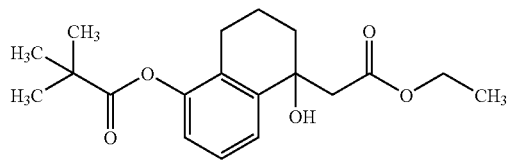

To an anhydrous benzene (60 ml) suspension of zinc (16.9 g), iodine (catalytic amount) was added, followed by refluxing under heating, and an anhydrous benzene (120 ml) solution of the compound (45.4 g) prepared in Reference Example 3 and bromoacetic acid ethyl ester (25.0 ml) was added dropwise thereto, followed by refluxing under heating overnight. The reaction mixture was cooled to room temperature. The reaction mixture was added to iced water, and a concentrated hydrochloric acid was added thereto, followed by extracting with ethyl acetate. The extract was washed with water and saturated saline in this order, dried with anhydrous magnesium sulfate, and concentrated. The residue was purified by silica gel column chromatography (hexane:ethyl acetate=8:1 to 5:1) to thereby obtain the title compound (33.5 g) having the following physical data.

TLC: Rf 0.52 (hexane:ethyl acetate=85:15); NMR (CDCl$_3$): δ 7.42(dd, J=8.0, 2.0 Hz, 1H), 7.17(t, J=8.0 Hz, 1H), 6.85(dd, J=8.0, 2.0 Hz, 1H), 4.16(q, J=7.0 Hz, 2H), 4.10–3.90(br, 1H), 2.80(d, J=14.0 Hz, 1H), 2.76(d, J=14.0 Hz, 1H), 2.68–2.40(m, 2H), 2.12–1.44(m, 4H), 1.35(s, 9H), 1.24(t, J=7.0 Hz, 3H).

REFERENCE EXAMPLE 5

2-(5-pivaloyloxy-3,4-dihydronaphthalen-1-yl)acetic acid ethyl ester

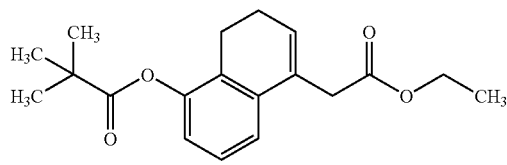

To a toluene (80 ml) solution of the compound (33.5 g) prepared in Reference Example 4, p-toluenesulfonic acid monohydrate (1.52 g) was added, followed by refluxing under heating overnight. The reaction mixture was cooled to room temperature, diluted with ethyl acetate, washed with water, a saturated aqueous sodium hydrogen carbonate solution, water and a saturated saline in this order, dried with anhydrous magnesium sulfate, and concentrated. The residue was purified by silica gel column chromatography (hexane:ethyl acetate=20:1 to 10:1) to thereby obtain the title compound (13.2 g) having the following physical data.

TLC: Rf 0.56 (hexane:ethyl acetate=3:1); NMR(CDCl$_3$): δ 7.18(t, J=8.0 Hz, 1H), 7.08(dd, J=8.0, 1.0 Hz, 1H), 6.86(dd, J=8.0, 1.0 Hz, 1H), 6.01(t, J=4.5 Hz, 1H), 4.14(q, J=7.0 Hz, 2H), 3.44–3.40(m, 2H), 2.63(t, J=8.0 Hz, 2H), 2.36–2.23(m, 2H), 1.38(s, 9H), 1.22(t, J=7.0 Hz, 3H).

REFERENCE EXAMPLE 6

2-(5-hydroxy-3,4-dihydronaphthalen-1-yl)acetic acid ethyl ester

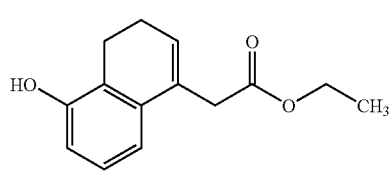

Under ice-cooling, to an ethanol (50 ml) solution of the compound (13.2 g) prepared in Reference Example 5, an ethanol solution of sodium ethylate (20 ml, 2.6 M) was added dropwise, followed by stirring at room temperature for 3 hours. The reaction mixture was added to a mixture of 2N hydrochloric acid and ice, followed by extracting with ethyl acetate. The extract was washed with a saturated saline, dried with anhydrous magnesium sulfate, and concentrated. The residue was purified by silica gel column chromatography (hexane:ethyl acetate=4:1 to 2:1). The obtained oil was subjected to crystallization by a mixture solvent of hexane and ethyl acetate. Furthermore, the obtained crystal was subjected to recrystallization by a mixture solvent of hexane and ethyl acetate to thereby obtain the title compound (7.73 g) having the following physical data.

TLC: Rf 0.34 (hexane:ethyl acetate=3:1); NMR(CDCl$_3$): δ 7.00(t, J=8.0 Hz, 1H), 6.78(d, J=8.0, 1.0 Hz, 1H), 6.63(dd, J=8.0, 1.0 Hz, 1H), 5.98(t, J=4.5 Hz, 1H), 5.25(brs, 1H), 4.15(q, J=7.0 Hz, 2H), 3.44–3.41(m, 2H), 2.74(t, J=8.0 Hz, 2H), 2.36–2.23(m, 2H), 1.23(t, J=7.0 Hz, 3H).

REFERENCE EXAMPLE 7

5-(5-methoxy-3,4-dihydronaphthalen-1(2H)ylidene)pentanoic acid

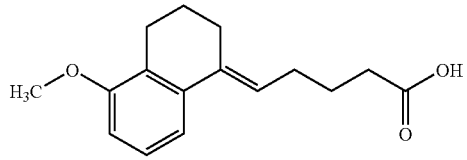

To an anhydrous tetrahydrofuran (200 ml) solution of (4-carboxybutyl)triphenylphosphonium bromide (25.0 g), potassium t-butoxide (12.7 g) was added, followed by stirring at 30° C. for 1 hour. To the reaction mixture, a tetrahydrofuran (20 ml) solution of 5-methoxy-1-tetralone (5.0 g) was added, followed by stirring at room temperature overnight. The reaction mixture was added to a mixture of saturated aqueous ammonium chloride solution and ice, followed by extracting with ethyl acetate. The extract was concentrated to thereby obtain the crude title compound having the following physical data. The obtained compound was used without purification in the subsequent reaction.

TLC: Rf 0.34 (hexane:ethyl acetate=2:1).

REFERENCE EXAMPLE 8

5-(5-methoxy-3,4-dihydronaphthalen-1(2H)ylidene)pentanoic acid methyl ester

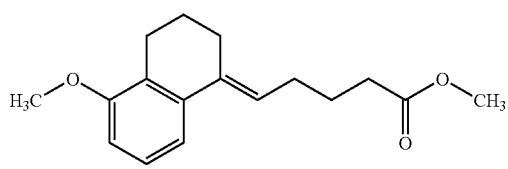

To an anhydrous dimethylformamide (40 ml) solution of the compound prepared in Reference Example 7, methyl iodide (5.3 ml) and potassium carbonate (17.6 g) were added, followed by stirring at room temperature overnight. The reaction mixture was added to iced water, followed by extracting with ethyl acetate. The extract was washed with a saturated saline, dried with anhydrous magnesium sulfate, and concentrated. The residue was purified by silica gel column chromatography (hexane:ethyl acetate=5:1) to thereby obtain the title compound (6.80 g) having the following physical data.

TLC: Rf 0.72 (hexane:ethyl acetate=2:1); NMR(CDCl$_3$): δ 7.18(dd, J=7.6, 1.2 Hz, 1H), 7.10(t, J=7.6 Hz, 1H), 6.70(dd, J=7.6, 1.2 Hz, 1H), 5.96(brt, J=7.2 Hz, 1H), 3.81(s, 3H), 3.66(s, 3H), 2.71(t, J=6.4 Hz, 2H), 2.48–2.18(m, 6H), 1.89–1.71(m, 4H).

REFERENCE EXAMPLE 9

5-(5-hydroxy-3,4-dihydronaphthalen-1-yl)pentanoic acid

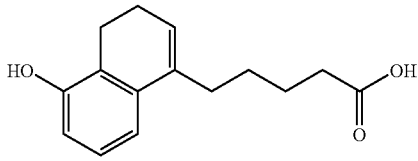

The mixture of the compound (6.83 g) prepared in Reference Example 8 and pyridine hydrochloric acid (39 g) was stirred at 180° C. for 2 hours. The reaction mixture was cooled to room temperature, and water was added thereto, followed by extracting with ethyl acetate. The extract was washed with 2N hydrochloric acid and saturated saline in this order, dried with anhydrous magnesium sulfate, and concentrated to thereby obtain the crude title compound having the following physical data. The obtained compound was used without purification in the subsequent reaction TLC: Rf 0.12 (hexane:ethyl acetate=2:1).

REFERENCE EXAMPLE 10

5-(5-hydroxy-3,4-dihydronaphthalen-1-yl)pentanoic acid methyl ester

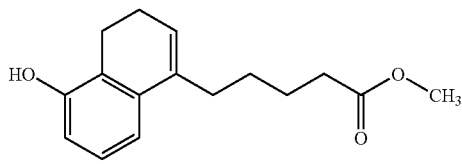

Thionyl chloride (1.9 ml) was added to methanol (25 ml) at −30° C., followed by stirring at −20° C. for 15 minutes. To the reaction solution, the methanol (10 ml) solution of the compound prepared in Reference Example 9 was added, followed by stirring at room temperature for 30 minutes. The reaction mixture was concentrated. The residue was diluted with ethyl acetate. The diluted solution was washed with a saturated aqueous sodium hydrogen carbonate solution, water and saturated saline in this order, dried with anhydrous magnesium sulfate, and concentrated. The residue was purified by silica gel column chromatography (hexane:ethyl acetate=4:1) to thereby obtain the title compound (4.91 g) having the following physical data TLC: Rf 0.48 (hexane:ethyl acetate=2:1); NMR(CDCl$_3$): δ 7.08(t, J=7.8 Hz, 1H), 6.86(brd, J=7.8 Hz, 1H), 6.68(dd, J=7.8, 1.0 Hz, 1H), 5.85(t, J=4.4 Hz, 1H), 4.96(brs, 1H), 3.66(s, 3H), 2.70(t, J=8.0 Hz, 2H), 2.49–2.17(m, 6H), 1.89–1.45(m, 4H).

REFERENCE EXAMPLE 11

N'-((1E)-5-hydroxy-3,4-dihydronaphthalen-1(2H)ylidene)-2,4,6-triisopropylbenzenesulfonohydrazide

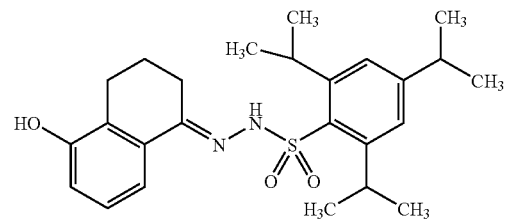

To a methanol (250 ml) solution of 2,4,6-triisopropylbenzenesulfonylhydrazide (36.8 g) and 5-hydroxy-1,2,3,4-tetrahydronaphthalen-1-one (20.0 g), a concentrated hydrochloric acid (4.3 ml) was added at room temperature, followed by stirring at 40° C. for 2 hours. Under ice-cooling, the reaction mixture was stirred for 1 hour. The deposited crystal was separated. The separation was washed with cold methanol, dried under reduced pressure to thereby obtain the title compound (49.2 g) having the following physical data.

TLC: Rf 0.28 (hexane:ethyl acetate=3:1); NMR(CDCl$_3$): δ 7.57(br, 1H), 7.56(d, J=8.1 Hz, 1H), 7.16(s, 2H), 6.99(t, J=8.1 Hz, 1H), 6.71(d, J=8.1 Hz, 1H), 4.37 –4.24(m, 2H), 2.88(m, 1H), 2.69(t, J=6.0 Hz, 2H), 2.43(t, J=6.6 Hz, 2H), 1.96–1.85(m, 2H), 1.30(d, J=6.9 Hz, 12H), 1.23(d, J=6.9 Hz, 6H).

REFERENCE EXAMPLE 12

5-hydroxy-3,4-dihydronaphthalen-1-ylmethanol

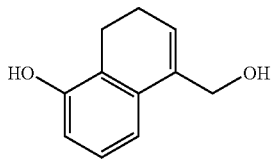

To an anhydrous tetrahydrofuran (510 ml) solution of the compound (49.2 g) prepared in Reference Example 11, n-butyl lithium (221 ml, 1.56 M in hexane) was added at −78° C., followed by stirring at −78° C. for 30 minutes. The reaction mixture was heated up to 0° C., followed by stirring at 0° C. for 30 minutes. Under ice-cooling, paraformaldehyde (11.7 g) was added to the reaction mixture, followed by heating up to room temperature, and the reaction mixture was stirred for 1 hour. Under ice-cooling, a saturated aqueous ammonium chloride solution was added to the reaction mixture for liquid separation. The aqueous layer was extracted with ethyl acetate. The combined organic layer was washed with a saturated saline, dried with anhydrous sodium sulfate, and concentrated. The residue was purified by silica gel column chromatography (hexane:ethyl acetate=3:1 to 1:1) to thereby obtain the title compound (15.7 g) having the following physical data.

TLC: Rf 0.28 (hexane:ethyl acetate=2:1); NMR(CDCl$_3$): δ 9.17(brs, 1H), 6.94(t, J=8.1 Hz, 1H), 6.74(d, J=8.1 Hz, 1H), 6.68(dd, J=8.1, 1.2 Hz, 1H), 6.01(t, J=4.8 Hz, 1H), 4.50(brs, 1H), 4.25(d, J=1.2 Hz, 2H), 2.60(t, J=7.8 Hz, 2H), 2.22–2.09(m, 2H).

REFERENCE EXAMPLE 13

5-methoxymethoxy-3,4-dihydronaphthalen-1-yl-methanol

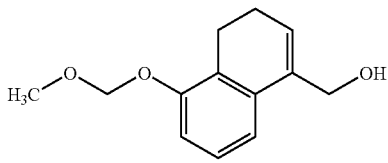

Under ice-cooling, to an anhydrous tetrahydrofuran (135 ml) solution of the compound (15.7 g) prepared in Reference Example 12, sodium hydride (3.75 g, 63.1%) was added, followed by stirring at room temperature for 30 minutes. To the reaction mixture, chloromethyl methyl ether (7.41 ml) was added dropwise under ice-cooling, followed by stirring at room temperature for 13 hours. To the reaction mixture, iced water and a saturated aqueous ammonium chloride solution were added, followed by extracting with ethyl acetate. The extract was washed with water and saturated saline in this order, dried with anhydrous sodium sulfate, and concentrated. The residue was purified by silica gel column chromatography (hexane:ethyl acetate=4:1 to 2:1) to thereby obtain the title compound (15.1 g) having the following physical data.

TLC: Rf 0.38 (hexane:ethyl acetate=2:1); NMR(CDCl$_3$): δ 7.16(t, J=7.8 Hz, 1H), 7.05(d, J=7.8 Hz, 1H), 7.00(d, J=7.8 Hz, 1H), 6.14(t, J=4.5 Hz, 1H), 5.20(s, 2H), 4.51(brs, 2H), 3.49(s, 3H), 2.82(t, j=8.1 Hz, 2H), 2.30(td, j=8.1, 4.5 Hz, 2H), 1.46(brs, 1H).

REFERENCE EXAMPLE 14

1-bromomethyl-5-methoxymethoxy-3,4-dihydronaphthalene

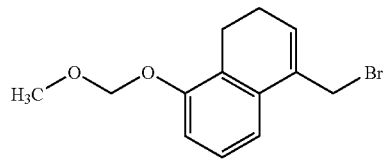

To a methylene chloride (110 ml) solution of the compound (7.53 g) prepared in Reference Example 13 and triphenylphosphine (9.59 g), tetrabromomethane (12.1 g) was added under ice-cooling, followed by stirring under ice-cooling for 40 minutes. The reaction mixture was concentrated. To the residue, a mixed solvent of diethyl ether and hexane (5:1) was added for excluding triphenylphosphine oxide. The obtained crude product was purified by silica gel column chromatography (hexane: ethyl acetate=20:1 to 10:1) to thereby obtain the title compound (6.32 g) having the following physical data.

TLC: Rf 0.76 (hexane:ethyl acetate=2:1); NMR(CDCl$_3$): δ 7.20(t, J=8.1 Hz, 1H), 7.12(d, J=8.1 Hz, 1H), 7.03(d, J=8.1 Hz, 1H), 6.30(t, J=4.8 Hz, 1H), 5.20(s, 2H), 4.36(s, 2H), 3.49(s, 3H), 2.83(t, J=8.7 Hz, 2H), 2.31(td, J=8.7, 4.8 Hz, 2H).

REFERENCE EXAMPLE 15

2,2-dimethyl-3-(5-methoxymethoxy-3,4-dihydronaphthalen-1-yl)propanoic acid methyl ester

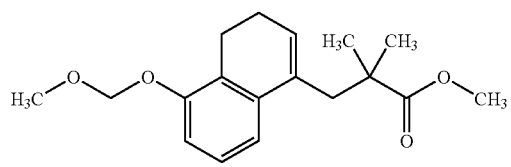

Under ice-cooling, to an anhydrous tetrahydrofuran (30 ml) solution of 2-methylpropanoic acid methyl ester (5.11 ml), lithium diisopropylamide (22.3 ml) was added dropwise, followed by stirring at 30° C. for 30 minutes. Under ice-cooling, to the reaction mixture, an anhydrous tetrahydrofuran (20 ml) solution of the compound (6.32 g) prepared in Reference Example 14 was added dropwise, followed by stirring at room temperature for 2 hours. To the reaction mixture, a saturated aqueous ammonium chloride solution was added, followed by extracting with ethyl acetate. The extract was washed with saturated saline, dried with anhydrous magnesium sulfate, and concentrated. The residue was purified by silica gel column chromatography (hexane:ethyl acetate=8:1 to 6:1) to thereby obtain the title compound (7.02 g) having the following physical data.

TLC: Rf 0.55 (hexane:ethyl acetate=5:1); NMR(CDCl$_3$): δ 7.10(t, J=8.1 Hz, 1H), 6.97(d, J=8.1 Hz, 1H), 6.94(d, J=8.1 Hz, 1H), 5.85(t, J=4.5 Hz, 1H), 3.49(s, 3H), 3.47(s, 3H), 2.74(t, J=7.8 Hz, 2H), 2.72(s, 2H), 2.17(td, J=7.8, 4.5 Hz, 2H), 1.15(s, 6H).

REFERENCE EXAMPLE 16

2,2-dimethyl-3-(5-hydroxy-3,4-dihydronaphthalen-1-yl)propanoic acid methyl ester

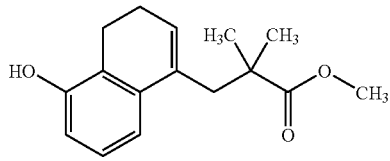

To a methanol (110 ml) solution of the compound (6.78 g) prepared in Reference Example 15, 4N hydrogen chloride-dioxane solution (8.4 ml) was added, followed by stirring at room temperature for 15 hours. The reaction mixture was concentrated. The residue was extracted with ethyl acetate. The extract was washed with a saturated aqueous sodium hydrogen carbonate solution and saturated saline in this order, dried with anhydrous sodium sulfate, and concentrated to thereby obtain the title compound (5.78 g) having the following physical data.

TLC: Rf 0.30 (hexane:ethyl acetate=5:1); NMR(CDCl$_3$): δ 7.03(t, J=8.1 Hz, 1H), 6.89(d, J=8.1 Hz, 1H), 6.65(dd, J=1.2, 8.1 Hz, 1H), 5.85(t, J=4.5 Hz, 1H), 4.71(s, 1H), 3.46(s, 3H), 2.71(d, J=1.2 Hz, 2H), 2.67(t, J=8.1 Hz, 2H), 2.20(td, J=8.1, 4.5 Hz, 2H), 1.56(s, 6H).

REFERENCE EXAMPLE 17

1-cyclopropylidene-5-methoxy-1,2,3,4-tetrahydronaphthalene

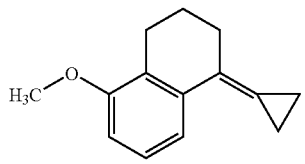

Under ice-cooling, to an anhydrous tetrahydrofuran (200 ml) solution of (3-bromopropyl)triphenylphosphinium bromide (19.8 g), potassium t-butoxide (9.58 g) was added, followed by stirring at room temperature for 1.5 hours. To the reaction mixture, 5-methoxy-1-tetralone (5.0 g) was added, followed by stirring at room temperature for 5 hours. The reaction mixture was poured into a saturated aqueous ammonium chloride solution. The aqueous layer was extracted with ethyl acetate. The combined organic layer was washed with saturated saline, dried with anhydrous magnesium sulfate, and concentrated. The residue was purified by silica gel column chromatography (hexane:ethyl acetate=10:1) to thereby obtain the title compound (5.66 g) having the following physical data.

TLC: Rf 0.86 (hexane:ethyl acetate=10:1); NMR (CDCl$_3$): δ 7.56(d, J=7.8 Hz, 1H), 7.13(t, J=7.8 Hz, 1H), 6.70(d, J=7.8 Hz, 1H), 3.83(s, 3H), 2.76(t, J=6.4 Hz, 2H), 2.66–2.56(m, 2H), 1.94–1.80(m, 2H), 1.51–1.40(m, 2H), 1.12–1.02(m, 2H).

REFERENCE EXAMPLE 18

1-(3-bromopropyl)-5-methoxy-3,4-dihydronaphthalene

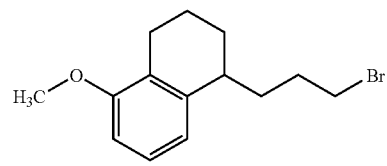

To a acetic acid (60 ml) solution of the compound (5.00 g) prepared in Reference Example 17, 47% hydrogen bromide aqueous solution (20 ml) was added, followed by stirring at room temperature for 2 hours. To the reaction mixture, iced water was added, followed by extracting with ethyl acetate. The extract was washed with saturated saline, dried with anhydrous magnesium sulfate, and concentrated. The residue was purified by silica gel column chromatography (hexane:ethyl acetate=10:1) to thereby obtain the title compound (7.05 g) having the following physical data.

TLC: Rf 0.69 (hexane:ethyl acetate=10:1); NMR (CDCl$_3$): δ 7.16(t, J=7.8 Hz, 1H), 6.90(d, J=7.8 Hz, 1H), 6.79(d, J=7.8 Hz, 1H), 5.92(t, J=4.6 Hz, 1H), 3.83(s, 3H), 3.44(t, J=6.6 Hz, 2H), 2.74(t, J=7.6 Hz, 2H), 2.65–2.55(m, 2H), 2.28–2.15(m, 2H), 2.13–1.98(m, 2H).

REFERENCE EXAMPLE 19

2,2-dimethyl-5-(5-methoxy-3,4-dihydronaphthalen-1-yl)pentanoic acid methyl ester

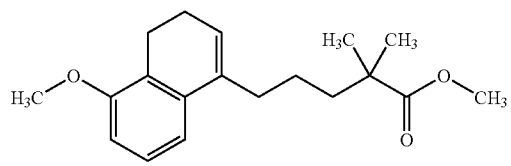

Under ice-cooling, to an anhydrous tetrahydrofuran (15 ml) solution of 2-methylpropanoic acid methyl ester (3.30 g), lithium diisopropylamide (16.5 ml, 2.0 M) was added, followed by stirring at 30° C. for 30 minutes. The reaction mixture was cooled to room temperature, and an anhydrous tetrahydrofuran (5 ml) solution of the compound (3.00 g) prepared in Reference Example 18 was added thereto, followed by stirring at room temperature for 3 hours. The reaction mixture was poured into a saturated aqueous ammonium chloride solution, followed by extracting with ethyl acetate. The extract was washed with saturated saline, dried with anhydrous magnesium sulfate, and concentrated. The residue was purified by silica gel column chromatography (hexane:ethyl acetate=100:1 to 20:1) to thereby obtain the crude title compound (3.68 g) having the following physical data. The obtained compound was used without purification in the subsequent reaction.

TLC: Rf 0.84 (hexane:ethyl acetate=2:1).

REFERENCE EXAMPLE 20

2,2-dimethyl-5-(5-hydroxy-3,4-dihydronaphthalen-1-yl)pentanoic acid

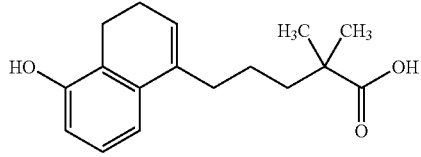

The mixture of the compound (3.68 g) prepared in Reference Example 19 and pyridine hydrochloric acid (17 g) was stirred at 180° C. overnight. The reaction mixture was cooled to room temperature, and water was added thereto, followed by extracting with ethyl acetate. The extract was washed with saturated saline, dried with anhydrous magnesium sulfate, and concentrated to thereby obtain the crude title compound having the following physical data. The obtained compound was used without purification in the subsequent reaction.

TLC: Rf 0.30 (hexane:ethyl acetate=2:1).

REFERENCE EXAMPLE 21

2,2-dimethyl-5-(5-hydroxy-3,4-dihydronaphthalen-1-yl)pentanoic acid methyl ester

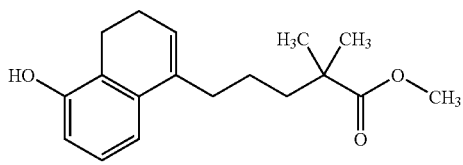

Thionyl chloride (0.86 ml) was added to cold methanol (11 ml), followed by stirring at −20° C. for 15 minutes. To the reaction solution, a methanol (5 ml) solution of the compound prepared in Reference Example 20 was added, followed by stirring at room temperature for 1 hour. The reaction mixture was concentrated. The residue was diluted with ethyl acetate. The diluted solution was washed with a saturated aqueous sodium hydrogen carbonate solution and saturated saline in this order, dried with anhydrous magnesium sulfate, and concentrated. The residue was purified by silica gel column chromatography (hexane:ethyl acetate=8:1) to thereby obtain the title compound (2.02 g) having the following physical data.

TLC: Rf 0.66 (hexane:ethyl acetate=2:1); NMR(CDCl$_3$): δ 7.05(t, J=8.0 Hz, 1H), 6.84(d, J=8.0 Hz, 1H), 6.68(dd, J=8.0, 1.0 Hz, 1H), 5.84(t, J=4.8 Hz, 1H), 5.01(brs, 1H), 3.60(s, 3H), 2.70(t, J=8.0 Hz, 2H), 2.44–2.32(m, 2H), 2.30–2.17(m, 2H), 1.75–1.34(m, 4H), 1.15(s, 6H).

REFERENCE EXAMPLE 22

2-benzyloxy-3-(5-methoxymethoxy-3,4-dihydronaphthalen-1-yl)propanoic acid

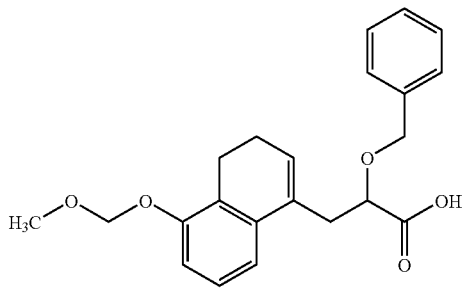

To a tetrahydrofuran (7 ml) solution of 2-benzyloxyacetic acid (0.30 ml), lithium diisopropylamide (2.4 ml) was added dropwise at −78° C. under argon atmosphere, followed by stirring at 0° C. for 10 minutes. The above obtained solution was added to a tetrahydrofuran (3 ml) solution of the compound (600 mg) prepared in Reference Example 14 at −78° C., followed by stirring at room temperature for 12 hours. The reaction mixture was poured into a saturated aqueous ammonium chloride solution for liquid separation. The aqueous layer was extracted with ethyl acetate. The combined organic layer was washed with saturated saline, dried with anhydrous magnesium sulfate, and concentrated. The residue was purified by silica gel column chromatography (chloroform:methanol=50:1) to thereby obtain the title compound (99 mg) having the following physical data.

TLC: Rf 0.33 (hexane:ethyl acetate=4:1).

REFERENCE EXAMPLE 23

2-benzyloxy-3-(5-hydroxy-3,4-dihydronaphthalen-1-yl)propanoic acid methyl ester

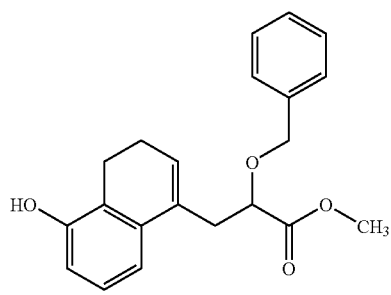

To a methanol (4 ml) solution of the compound (99 mg) prepared in Reference Example 22, 4N hydrogen chloride-dioxane solution (0.1 ml) was added, followed by stirring at room temperature for 15 hours. The reaction mixture was concentrated to thereby obtain the crude title compound having the following physical data. The obtained compound was used without purification in the subsequent reaction.

TLC: Rf 0.48 (hexane:ethyl acetate=2:1).

REFERENCE EXAMPLE 24

3-methoxycarbonyl-2-(4-methylbenzoylamino)propanoic acid

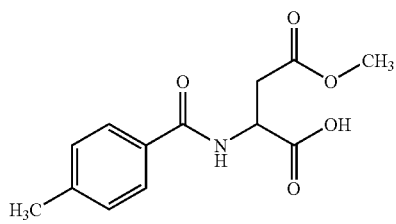

Aspartic acid β-methyl ester hydrochloride (184 g) was dissolved in water (1.3 L), and sodium hydrogen carbonate (277 g) was added thereto, and tetrahydrofuran (450 ml) and a tetrahydrofuran (50 ml) solution of 4-methylbenzoyl chloride (146 ml) was added dropwise thereto, followed by stirring at room temperature for 15 hours. The reaction mixture was washed with ethyl acetate. The aqueous layer was neutralized with 2N hydrochloric acid to pH 2 to 3, and extracted with ethyl acetate. The extract was washed with saturated saline, dried with anhydrous magnesium sulfate, and concentrated to thereby obtain the crude title compound (255 g) having the following physical data. The obtained compound was used without purification in the subsequent reaction.

TLC: Rf 0.28 (chloroform:methanol=5:1); NMR(CDCl$_3$): δ 7.71(d, J=8.1 Hz, 2H), 7.34(d, J=7.8 Hz, 1H), 7.24(d, J=8.1 Hz, 2H), 5.08(ddd, J=7.5, 4.5, 4.5 Hz, 1H), 3.73(s, 3H), 3.18(dd, J=17.1, 4.5 Hz, 1H), 3.00(dd, J=17.1, 4.5 Hz, 1H), 2.40(s, 3H).

REFERENCE EXAMPLE 25

3-acetyl-3-(4-methylbenzoylamino)propanoic acid methyl ester

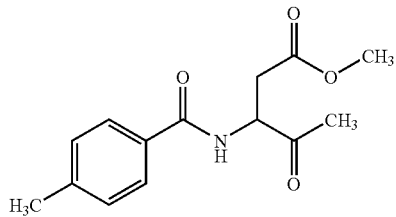

To a pyridine (480 ml) solution of the compound (255 g) prepared in Reference Example 24, acetic anhydride (453 ml) and 4-dimethylaminopyridine (3.52 g) were added, followed by stirring at 90° C. for 1 hour. The reaction mixture was cooled to room temperature, and concentrated. The residue was poured into iced water, followed by extracting with ethyl acetate. The extract was washed with water, 2N hydrochloric acid and saturated saline in this order, dried with anhydrous magnesium sulfate, and concentrated to thereby obtain the crude title compound having the following physical data.

TLC: Rf 0.23 (hexane:ethyl acetate=2:1).

REFERENCE EXAMPLE 26

2-(2-(4-methylphenyl)-5-methyloxazol-4-yl)acetic acid methyl ester

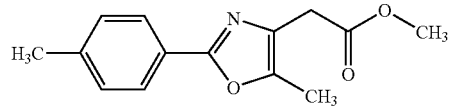

To a acetic anhydride (450 ml) solution of the compound prepared in Reference Example 25, concentrated sulfuric acid (86 ml) was added, followed by stirring at 90° C. for 1 hour. The reaction mixture was cooled to room temperature, and poured into ice. The aqueous layer was neutralized with 5N aqueous sodium hydroxide solution, and extracted with ethyl acetate. The extract was washed with 1N aqueous sodium hydroxide solution, water and saturated saline in this order, dried with anhydrous magnesium sulfate, and concentrated. The obtained oil was allowed to stand overnight. The obtained solid was washed with hexane, and filtered off by aspiration to thereby obtain the title compound (183 g) having the following physical data.

TLC: Rf 0.61 (hexane:ethyl acetate=2:1); NMR(CDCl$_3$): δ 7.87(d, J=8.1 Hz, 2H), 7.23(d, J=8.1 Hz, 2H), 3.73(s, 3H), 3.57(s, 2H), 2.38(s, 3H), 2.35(s, 3H).

REFERENCE EXAMPLE 27

2-(2-(4-methylphenyl)-5-methyloxazol-4-yl)ethanol

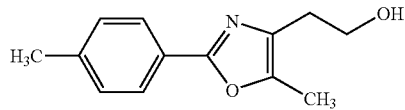

Under ice-cooling, lithium aluminum hydride (18.6 g) was suspended in anhydrous tetrahydrofuran (250 ml), and an anhydrous tetrahydrofuran (250 ml) of the compound (120 g) prepared in Reference Example 26 was added dropwise thereto, followed by stirring for 30 minutes under ice-cooling. To the reaction mixture, a saturated aqueous sodium sulfate solution was added dropwise for liquid separation. The organic layer was dried with anhydrous magnesium sulfate, and filtered with celite. The filtrate was concentrated. The residue was allowed to stand overnight. The obtained crystal was washed with a mixed solvent of hexane and ethyl acetate (10:1) to thereby obtain the title compound (80.0 g) having the following physical data.

TLC Rf 0.18 (hexane:ethyl acetate=2:1); NMR(CDCl₃): δ 7.86(m, 2H), 7.23(m, 2H), 3.92(br, 2H), 2.71(t, J=6.0 Hz, 2H), 2.39(s, 3H), 2.32(s, 3H).

EXAMPLE 1

3-(5-(2-(2-(4-methylphenyl)-5-methyloxazol-4-yl)ethoxy)-3,4-dihydronaphthalen-1-yl)propanoic acid methyl ester

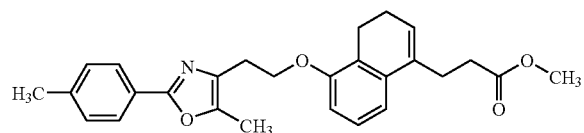

To a methylene chloride (15 ml) solution of the compound (600 mg) prepared in Reference Example 2, the compound (617 mg) prepared in Reference Example 27, triphenylphosphine (1.02 g) and 1,1'-(azodicarbonyl)dipiperidine (978 mg) were added, followed by stirring at room temperature for 3 hours. The reaction mixture was diluted with diethyl ether, and filtered with celite. The filtrate was concentrated under reduced pressure. The residue was purified by silica gel column chromatography (hexane:ethyl acetate=9:1 to 7:1 to 5:1 to 7:2) to thereby obtain the compound of the present invention (1.00 g) having the following physical data.

TLC: Rf 0.59 (hexane:ethyl acetate=2:1); NMR(CDCl₃): δ 7.86(d, J=8.1 Hz, 2H), 7.23(d, J=8.1 Hz, 2H), 7.13(dd, J=8.0, 8.0 Hz, 1H), 6.94–6.74(m, 2H), 5.87(dd, J=4.6, 4.6 Hz, 1H), 4.25(t, J=6.6 Hz, 2H), 3.67(s, 3H), 2.99(t, J=6.6 Hz, 2H), 2.85–2.63(m, 4H), 2.60–2.45(m, 2H), 2.39(s, 3H), 2.36(s, 3H), 2.30–2.10(m, 2H).

EXAMPLE 1(1) TO EXAMPLE 1(46)

The following compounds of the present invention were obtained in the same manner as in Example 2 using the compound prepared in Reference Example 2 or a corresponding phenol derivative instead thereof (Reference Example 6, Reference Example 10, Reference Example 16, Reference Example 21, Reference Example 23 and 2-(5-hydroxy-3,4-dihydronaphthalen-1-yl)acetic acid ethyl ester), and the compound prepared in Reference Example 27 or a corresponding ethanol derivative instead thereof.

EXAMPLE 1(1)

3-(5-(2-(2-phenyl-5-methyloxazol-4-yl)ethoxy)-3,4-dihydronaphthalen-1-yl)propanoic acid methyl ester

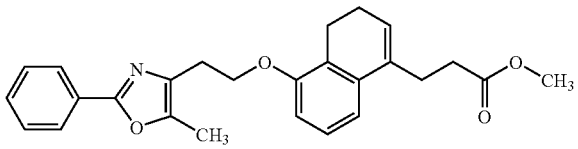

TLC: Rf 0.59 (hexane:ethyl acetate=2:1); NMR(CDCl₃): δ 8.02–7.94(m, 2H), 7.47–7.37(m, 3H), 7.13(t, J=8.0 Hz, 1H), 6.89(d, J=8.0 Hz, 1H), 6.80(d, J=8.0 Hz, 1H), 5.87(brt, J=4.5 Hz, 1H), 4.25(t, J=6.6 Hz, 2H), 3.67(s, 3H), 2.99(t, J=6.6 Hz, 2H), 2.82–2.65(m, 4H), 2.58–2.47(m, 2H), 2.37(s, 3H), 2.27–2.11(m, 2H).

EXAMPLE 1(2)

3-(5-(2-(2-(6-dimethylaminopyridin-3-yl)-5-methyloxazol-4-yl)ethoxy)-3,4-dihydronaphthalen-1-yl)propanoic acid methyl ester

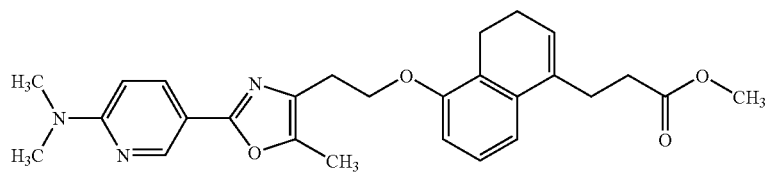

TLC: Rf 0.16 (hexane:ethyl acetate=2:1); NMR(CDCl₃): δ 8.74(dd, J=2.4, 0.8 Hz, 1H), 7.99(dd, J=9.0, 2.4 Hz, 1H), 7.13(d, J=8.0 Hz, 1H), 6.88(d, J=8.0 Hz, 1H), 6.81(d, J=8.0 Hz, 1H), 6.52(dd, J=9.0, 0.8 Hz, 1H), 5.87(brt, J=4.6 Hz, 1H), 4.24(t, J=6.8 Hz, 2H), 3.67(s, 3H), 3.14(s, 6H), 2.96(t, J=6.8 Hz, 2H), 2.82–2.65(m, 4H), 2.57–2.47(m, 2H), 2.34(s, 3H), 2.27–2.11(m, 2H).

EXAMPLE 1(3)

3-(5-(2-(2-(1,3-dioxaindan-5-yl)-5-methyloxazol-4-yl)ethoxy)-3,4-dihydronaphthalen-1-yl)propanoic acid methyl ester

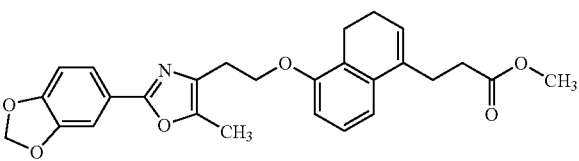

TLC: Rf 0.49 (hexane:ethyl acetate=2:1); NMR(CDCl₃): δ 7.51(dd, J=8.2, 1.6 Hz, 1H), 7.43(d, J=1.6 Hz, 1H), 7.13(dd, J=8.0, 8.0 Hz, 1H), 6.94–6.76(m, 3H), 6.01(s, 2H), 5.87(dd, J=4.5, 4.5 Hz, 1H), 4.24(t, J=6.6 Hz, 2H), 3.67(s, 3H), 2.96(t, J=6.6 Hz, 2H), 2.84–2.62(m, 4H), 2.60–2.45(m, 2H), 2.34(s, 3H), 2.26–2.10(m, 2H).

EXAMPLE 1(4)

3-(5-(2-(2-(4-t-butylphenyl)-5-methyloxazol-4-yl)ethoxy)-3,4-dihydronaphthalen-1-yl)propanoic acid methyl ester

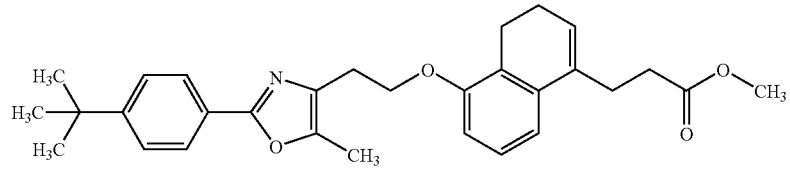

TLC: Rf 0.61 (hexane:ethyl acetate=2:1); NMR(CDCl$_3$): δ 7.89(d, J=8.6 Hz, 2H), 7.44(d, J=8.6 Hz, 2H), 7.12(dd, J=8.2, 8.0 Hz, 1H), 6.88(d, J=8.0 Hz, 1H), 6.80(d, J=8.0 Hz, 1H), 5.87(t, J=6.6 Hz, 1H), 4.24(t, J=6.6 Hz, 2H), 3.67(s, 3H), 2.98(t, J=6.6 Hz, 2H), 2.82–2.63(m, 4H), 2.58–2.47(m, 2H), 2.37(s, 3H), 2.26–2.10(m, 2H), 1.34(s, 9H).

EXAMPLE 1(5)

3-(5-(2-(2-(6-(morpholin-4-yl)pyridin-3-yl)-5-methyloxazol-4-yl)ethoxy)-3,4-dihydronaphthalen-1-yl)propanoic acid methyl ester

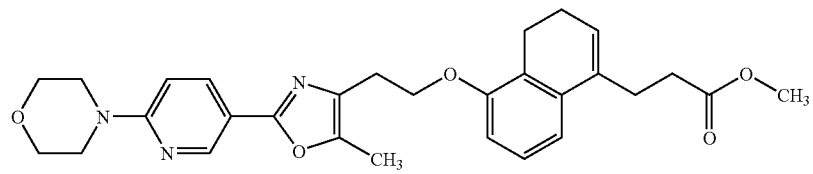

TLC: Rf 0.75 (chloroform:methanol=10:1); NMR (CDCl$_3$): δ 8.76(d, J=1.8 Hz, 1H), 8.04(dd, J=8.8, 1.8 Hz, 1H), 7.13(dd, J=8.0, 7.8 Hz, 1H), 6.89(d, J=7.8 Hz, 1H), 6.80(d, J=8.0 Hz, 1H), 6.64(d, J=8.8 Hz, 1H), 5.87(m, 1H), 4.23(t, J=6.4 Hz, 2H), 3.82(m, 4H), 3.59(m, 4H), 2.96(t, J=6.4 Hz, 2H), 2.83–2.63(m, 4H), 2.57–2.48(m, 2H), 2.08 (m, 2H).

EXAMPLE 1(6)

3-(5-(2-(2-(4-dimethylaminophenyl)-5-methyloxazol-4-yl)ethoxy)-3,4-dihydronaphthalen-1-yl)propanoic acid methyl ester

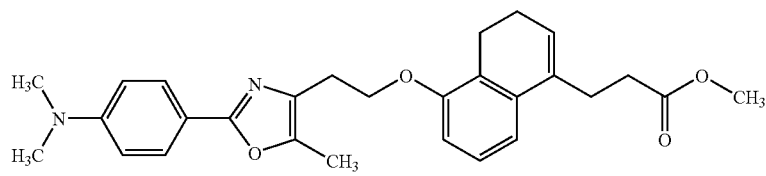

TLC: Rf 0.37 (hexane:ethyl acetate=2:1); NMR(CDCl$_3$): δ 7.80(d, J=9 Hz, 2H), 7.15(m, 1H), 6.90–6.70(m, 4H), 5.90(t, J=4 Hz, 1H), 4.25(t, J=7 Hz, 2H), 3.70(s, 3H), 3.00(s, 6H), 2.95(t, J=7 Hz, 2H), 2.80–2.50(m, 6H), 2.35(s, 3H), 2.20(m, 2H).

EXAMPLE 1(7)

3-(5-(2-(2-isopropyl-5-methyloxazol-4-yl)ethoxy)-3,4-dihydronaphthalen-1-yl)propanoic acid ethyl ester

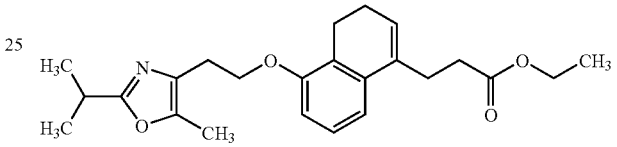

TLC: Rf 0.57 (hexane:ethyl acetate=2:1); NMR(CDCl$_3$): δ 7.15(dd, J=7.5, 7.5 Hz, 1H), 6.90(d, J=7.5 Hz, 1H), 6.80(d, J=7.5 Hz, 1H), 5.90(t, J=4 Hz, 1H), 4.20–4.10(m, 4H), 3.00(m, 1H), 2.90(t, J=6 Hz, 2H), 2.75(m, 2H), 2.65(t, J=8.5 Hz, 2H), 2.55(t, J=8.5 Hz, 2H), 2.20(s, 3H), 2.20(m, 2H), 1.35–1.20(m, 9H).

EXAMPLE 1(8)

3-(5-(2-(2-(4-trifluoromethylphenyl)-5-methyloxazol-4-yl)ethoxy)-3,4-dihydronaphthalen-1-yl)propanoic acid ethyl ester

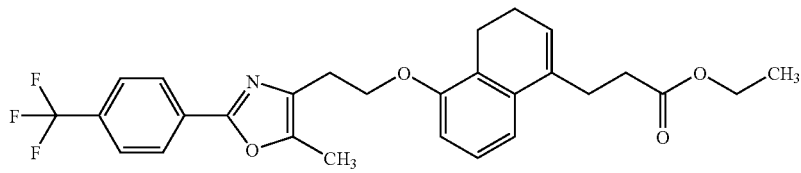

TLC: Rf 0.73 (hexane:ethyl acetate=2:1); NMR(CDCl₃): δ 8.10(d, J=8 Hz, 2H), 7.70(d, J=8 Hz, 2H), 7.15(dd, J=8, 8 Hz, 1H), 6.95–6.80(m, 2H), 5.85(m, 1H), 4.25(t, J=6 Hz, 2H), 4.15(q, J=7 Hz, 2H), 3.00(t, J=6 Hz, 2H), 2.80–2.65(m, 4H), 2.50(m, 2H), 2.40(s, 3H), 2.20(m,2H), 1.25(t, J=7 Hz, 3H).

EXAMPLE 1(9)

3-(5-(2-(2-(4-trifluoromethyloxyphenyl)-5-methyloxazol-4-yl)ethoxy)-3,4-dihydronaphthalen-1-yl)propanoic acid ethyl ester

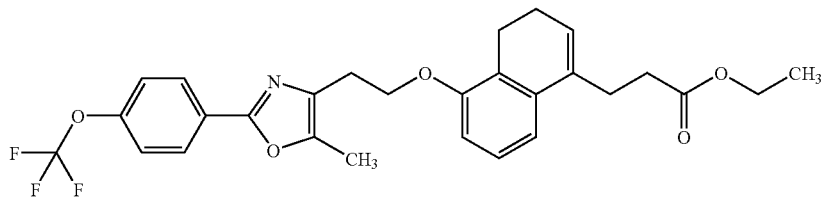

TLC: Rf 0.74 (hexane:ethyl acetate=2:1); NMR(CDCl₃): δ 8.00(d, J=9 Hz, 2H), 7.25(d, J=9 Hz, 2H), 7.15(dd, J=8, 8 Hz, 1H), 6.90(d, J=8 Hz, 1H), 6.80(d, J=8 Hz, 1H), 5.85(m, 1H), 4.25(t, J=6 Hz, 2H), 4.15(q, J=7 Hz, 2H), 3.00(t, J=6 Hz, 2H), 2.80–2.60(m, 4H), 2.50(m, 2H), 2.40(s, 3H), 2.20(m,2H), 1.25(t, J=7 Hz, 3H).

TLC: Rf 0.58 (hexane:ethyl acetate=2:1); NMR(CDCl₃): δ 7.85(d, J=8 Hz, 2H), 7.25(d, J=8 Hz, 2H), 7.15(dd, J=8, 8 Hz, 1H), 6.90(d, J=8 Hz, 1H), 6.80(d, J=8 Hz, 1H), 5.85(m, 1H), 4.25(t, J=7 Hz, 2H), 4.15(q, J=10 Hz, 2H), 3.00(t, J=7 Hz, 2H), 2.80–2.65(m, 4H), 2.50(m, 2H), 2.40(s, 3H), 2.20(m, 2H), 1.25(t, J=10 Hz, 3H).

EXAMPLE 1(10)

3-(5-(2-(2-(4-methylphenyl)-5-methyloxazol-4-yl)ethoxy)-3,4-dihydronaphthalen-1-yl)propanoic acid ethyl ester

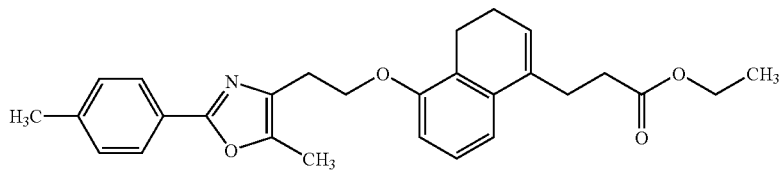

EXAMPLE 1 (11)

3-(5-(2-(2-(4-chlorophenyl)-5-methyloxazol-4-yl)ethoxy)-3,4-dihydronaphthalen-1-yl)propanoic acid ethyl ester

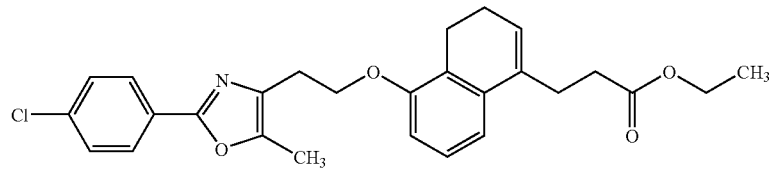

TLC: Rf 0.64 (hexane:ethyl acetate=2:1); NMR(CDCl$_3$): δ 7.95(d, J=8 Hz, 2H), 7.40(d, J=8 Hz, 2H), 7.15(dd, J=8, 8 Hz, 1H), 6.90(d, J=8 Hz, 1H), 6.80(d, J=8 Hz, 1H), 5.85(t, J=4 Hz, 1H), 4.20(t, J=6 Hz, 2H), 4.15(q, J=7 Hz, 2H), 3.00(t, J=6 Hz, 2H), 2.80–2.65(m, 4H), 2.50(m, 2H), 2.40(s, 3H), 2.20(m,2H), 1.25(t, J=7 Hz, 3H).

EXAMPLE 1(12)

3-(5-(2-(2-(4-methylthiophenyl)-5-methyloxazol-4-yl)ethoxy)-3,4-dihydronaphthalen-1-yl)propanoic acid ethyl ester

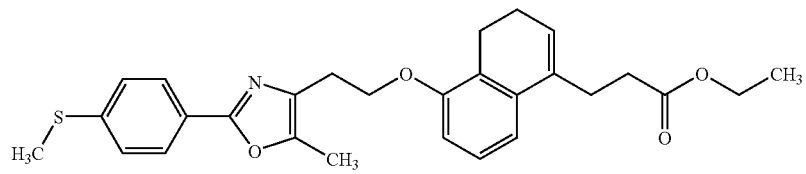

TLC: Rf 0.50 (hexane:ethyl acetate=2:1); NMR(CDCl$_3$): δ 7.85(d, J=8 Hz, 2H), 7.30(d, J=8 Hz, 2H), 7.15(dd, J=8, 8 Hz, 1H), 6.90(d, J=8 Hz, 1H), 6.80(d, J=8 Hz, 1H), 5.85(t, J=4 Hz, 1H), 4.25(t, J=7 Hz, 2H), 4.15(q, J=7 Hz, 2H), 3.00(t, J=7 Hz, 2H), 2.80–2.65(m, 4H), 2.50(s, 3H), 2.50(m, 2H), 2.35(s, 3H), 2.10(m,2H), 1.25(t, J=7 Hz, 3H).

EXAMPLE 1(13)

3-(5-(2-(2-(4-isopropylphenyl)-5-methyloxazol-4-yl)ethoxy)-3,4-dihydronaphthalen-1-yl)propanoic acid ethyl ester

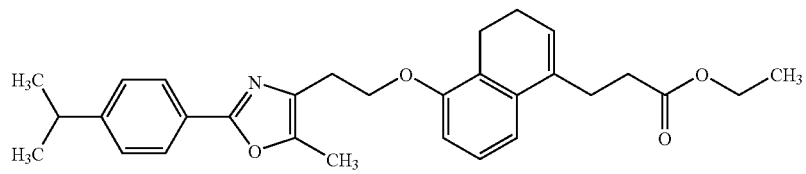

TLC: Rf 0.65 (hexane:ethyl acetate=2:1); NMR(CDCl$_3$): δ 7.90(d, J=8 Hz, 2H), 7.25(d, J=8 Hz, 2H), 7.15(dd, J=8, 8 Hz, 1H), 6.90(d, J=8 Hz, 1H), 6.80(d, J=8 Hz, 1H), 5.85(t, J=4 Hz, 1H), 4.25(t, J=6 Hz, 2H), 4.15(q, J=7 Hz, 2H), 3.00–2.90(m, 3H), 2.80–2.65(m, 4H), 2.50(m, 2H), 2.35(s, 3H), 2.20(m,2H), 1.20(d, J=8 Hz, 6H), 1.20(t, J=7 Hz, 3H).

EXAMPLE 1(14)

3-(5-(2-(2-(4-propylphenyl)-5-methyloxazol-4-yl)ethoxy)-3,4-dihydronaphthalen-1-yl)propanoic acid ethyl ester

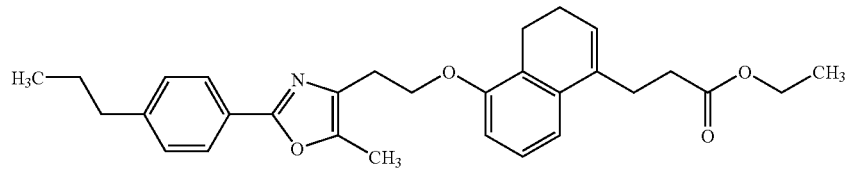

TLC: Rf 0.65 (hexane:ethyl acetate=2:1); NMR(CDCl$_3$):
δ 7.80(d, J=8 Hz, 2H), 7.25(d, J=8 Hz, 2H), 7.10(m, 1H), 6.90(m, 1H), 6.75(m, 1H), 5.85(m, 1H), 4.25(t, J=6 Hz, 2H), 4.15(q, J=7 Hz, 2H), 3.00(t, J=6 Hz, 2H), 2.80–2.60(m, 8H), 2.55(m, 2H), 2.35(s, 3H), 2.20(m, 2H), 1.25(t, J=7 Hz, 3H), 0.95(t, J=8 Hz, 3H).

EXAMPLE 1 (15)

3-(5-(2-(2-(2,2-difluoro-1,3-dioxaindan-5-yl)-5-methyloxazol-4-yl)ethoxy)-3,4-dihydronaphthalen-1-yl)propanoic acid ethyl ester

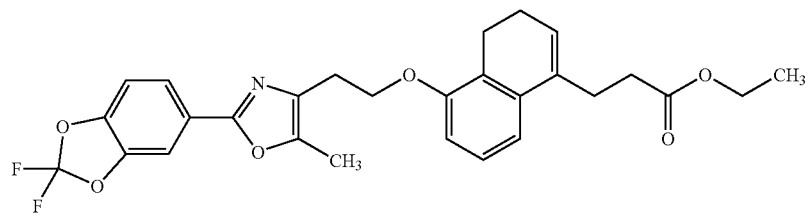

TLC: Rf 0.61 (hexane:ethyl acetate=2:1); NMR(CDCl$_3$):
δ 7.75(m, 1H), 7.70(m, 1H), 7.15–7.05(m, 2H), 6.90(d, J=8 Hz, 1H), 6.80(d, J=8 Hz, 1H), 5.85(t, J=4 Hz, 1H), 4.25(t, J=7 Hz, 2H), 4.15(q, J=7 Hz, 2H), 3.00(t, J=7 Hz, 2H), 2.80–2.65(m, 4H), 2.55(m, 2H), 2.35(s, 3H), 2.20(m, 2H), 1.25(t, J=7 Hz, 3H).

EXAMPLE 1(16)

3-(5-(2-(2-(6-diethylaminopyridin-3-yl)-5-methyloxazol-4-yl)ethoxy)-3,4-dihydronaphthalen-1-yl)propanoic acid ethyl ester

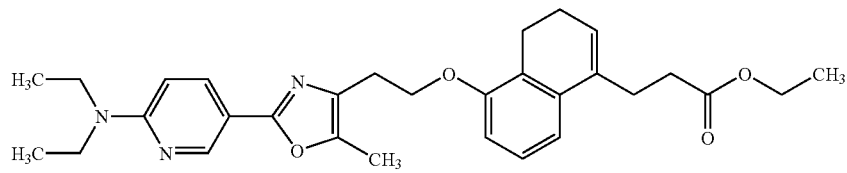

TLC: Rf 0.32 (hexane:ethyl acetate=2:1); NMR(CDCl₃): δ 8.71(d, J=2.4 Hz, 1H), 7.94(dd, J=9.0, 2.4 Hz, 1H), 7.13(dd, J=7.8, 7.8 Hz, 1H), 6.89(d, J=7.8 Hz, 1H), 6.80(d, J=7.8 Hz, 1H), 6.47(d, J=9.0 Hz, 1H), 5.87(t, J=4.5 Hz, 1H), 4.23(t, J=6.6 Hz, 2H), 4.13(q, J=7.2 Hz, 2H), 3.55(q, J=7.2 Hz, 4H), 2.96(t, J=6.6 Hz, 2H), 2.82–2.62(m, 4H), 2.58–2.44(m, 2H), 2.33(s, 3H), 2.26–2.10(m, 2H), 1.34–1.12(m, 9H).

EXAMPLE 1(17)

3-(5-(2-(2-(piperidin-1-yl)-5-methylthiazol-4-yl)ethoxy)-3,4-dihydronaphthalen-1-yl)propanoic acid ethyl ester

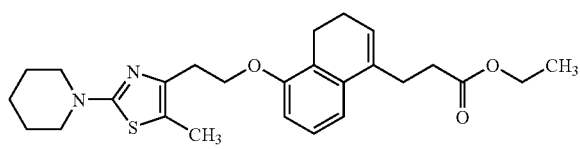

TLC: Rf 0.63 (hexane:ethyl acetate=2:1); NMR(CDCl₃): δ 7.12(t, J=7.8 Hz, 1H), 6.88(d, J=7.8 Hz, 1H), 6.79(d, J=7.8 Hz, 1H), 5.87(t, J=4.8 Hz, 1H), 4.21(t, J=6.9 Hz, 2H), 4.13(q, J=7.2 Hz, 2H), 3.36(t, J=4.8 Hz, 4H), 2.95(t, J=6.9 Hz, 2H), 2.76(t, J=7.2 Hz, 2H), 2.70(t, J=8.7 Hz, 2H), 2.51(t, J=8.7 Hz, 2H), 2.25(s, 3H), 2.23–2.14(m, 2H), 1.70–1.53(m, 6H), 1.25(t, J=7.2 Hz, 3H).

EXAMPLE 1(18)

3-(5-(2-(2-(4-methylpiperazin-1-yl)-5-methylthiazol-4-yl)ethoxy)-3,4-dihydronaphthalen-1-yl)propanoic acid ethyl ester

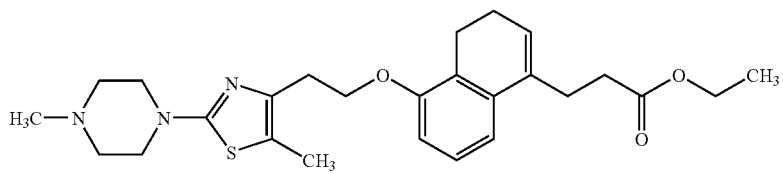

TLC: Rf 0.47 (chloroform:methanol=9:1); NMR(CDCl₃): δ 7.13(t, J=7.8 Hz, 1H), 6.88(d, J=7.8 Hz, 1H), 6.79(d, J=7.8 Hz, 1H), 5.87(t, J=4.5 Hz, 1H), 4.21(t, J=6.9 Hz, 2H), 4.13(q, J=7.2 Hz, 2H), 3.41(t, J=5.1 Hz, 4H), 2.96(t, J=6.9 Hz, 2H), 2.76(t, J=8.1 Hz, 2H), 2.69(t, J=8.4 Hz, 2H), 2.55–2.45(m, 6H), 2.33(s, 3H), 2.26(s, 3H), 2.23–2.13(m, 2H), 1.25(t, J=7.2 Hz, 3H).

EXAMPLE 1(19)

3-(5-(2-(2-(morpholin-4-yl)-5-methylthiazol-4-yl)ethoxy)-3,4-dihydronaphthalen-1-yl)propanoic acid ethyl ester

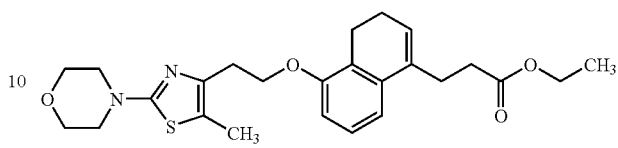

TLC: Rf 0.36 (hexane:ethyl acetate=2:1); NMR(CDCl₃): δ 7.13(t, J=8.1 Hz, 1H), 6.89(d, J=8.1 Hz, 1H), 6.79(d, J=8.1 Hz, 1H), 5.87(t, J=4.8 Hz, 1H), 4.21(t, J=6.6 Hz, 2H), 4.13(q, J=7.2 Hz, 2H), 3.79(t, J=4.8 Hz, 4H), 3.37(t, J=4.8 Hz, 4H), 2.96(t, J=6.6 Hz, 2H), 2.76(t, J=7.8 Hz, 2H), 2.69(t, J=7.8 Hz, 2H), 2.51(t, J=7.8 Hz, 2H), 2.27(s, 3H), 2.24–2.14(m, 2H), 1.25(t, J=7.2 Hz, 3H).

EXAMPLE 1(20)

3-(5-(2-(2-(thiomorpholin-4-yl)-5-methylthiazol-4-yl)ethoxy)-3,4-dihydronaphthalen-1-yl)propanoic acid ethyl ester

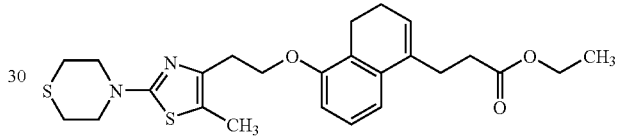

TLC: Rf 0.62 (hexane:ethyl acetate=2:1); NMR(CDCl₃): δ 7.13(t, J=7.8 Hz, 1H), 6.89(d, J=7.8 Hz, 1H), 6.79(d, J=7.8 Hz, 1H), 5.87(t, J=4.5 Hz, 1H), 4.20(t, J=6.6 Hz, 2H), 4.13(q, J=7.2 Hz, 2H), 3.77–3.70(m, 4H), 2.94(t, J=6.6 Hz, 2H), 2.80–2.64(m, 8H), 2.50(t, J=7.8 Hz, 2H), 2.25(s, 3H), 2.23–2.13(m, 2H), 1.25(t, J=7.2 Hz, 3H).

EXAMPLE 1(21)

3-(5-(2-(2-(6-methylpyridin-3-yl)-5-methyloxazol-4-yl)ethoxy)-3,4-dihydronaphthalen-1-yl)propanoic acid ethyl ester

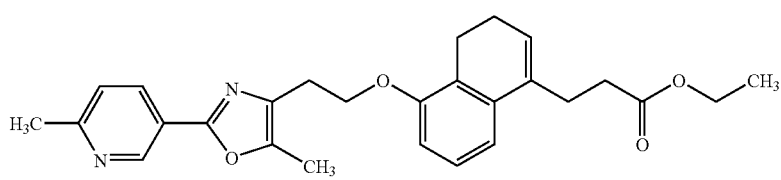

TLC: Rf 0.47 (chloroform:methanol=19:1); NMR (CDCl₃): δ 9.07(d, J=1.8 Hz, 1H), 8.12(dd, J=8.1, 1.8 Hz, 1H), 7.21(d, J=8.1 Hz, 1H), 7.14(t, J=7.8 Hz, 1H), 6.89(d, J=7.8 Hz, 1H), 6.80(d, J=7.8 Hz, 1H), 5.87(t, J=4.2 Hz, 1H), 4.25(t, J=6.6 Hz, 2H), 4.13(q, J=7.2 Hz, 2H), 2.99(t, J=6.6 Hz, 2H), 2.75(t, J=9.0 Hz, 2H), 2.69(t, J=8.4 Hz, 2H), 2.60(s, 3H), 2.50(t, J=8.4 Hz, 2H), 2.38(s, 3H), 2.24–2.14 (m, 2H), 1.24(t, J=7.2 Hz, 3H).

EXAMPLE 1(22)

3-(5-(2-(2-(1,5-dimethylpyrazol-3-yl)-5-methyloxazol-4-yl)ethoxy)-3,4-dihydronaphthalen-1-yl)propanoic acid ethyl ester

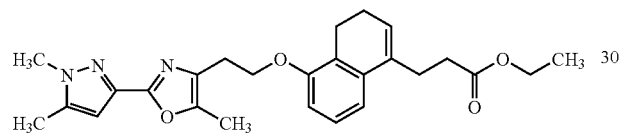

TLC: Rf 0.56 (chloroform:methanol=19:1); NMR (CDCl₃): δ 7.12(t, J=8.1 Hz, 1H), 6.88(d, J=8.1 Hz, 1H), 6.79(d, J=8.1 Hz, 1H), 6.51(s, 1H), 5.85(m, 1H), 4.24(t, J=6.6 Hz, 2H), 4.13(q, J=7.2 Hz, 2H), 3.85(s, 3H), 2.97(t, J=6.6 Hz, 2H), 2.75(t, J=7.5 Hz, 2H), 2.68(t, J=8.4 Hz, 2H), 2.50(t, J=8.4 Hz, 2H), 2.35(s, 3H), 2.31(s, 3H), 2.23–2.13 (m, 2H), 1.25(t, J=7.2 Hz, 3H).

EXAMPLE 1(23)

3-(5-(2-(2-(4-methylpiperidin-1-yl)-5-methylthiazol-4-yl)ethoxy)-3,4-dihydronaphthalen-1-yl)propanoic acid ethyl ester

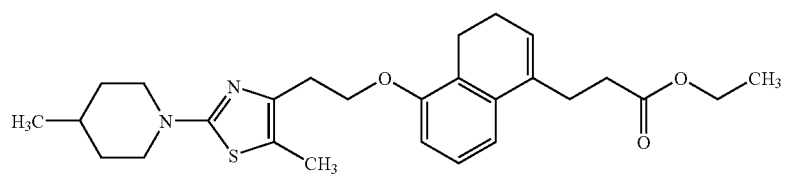

TLC: Rf 0.63 (hexane:ethyl acetate=2:1); NMR(CDCl₃): δ 7.12(t, J=7.8 Hz, 1H), 6.88(d, J=7.8 Hz, 1H), 6.79(d, J=7.8 Hz, 1H), 5.90–5.84(m, 1H), 4.21(t, J=6.9 Hz, 2H), 4.14(q, J=7.2 Hz, 2H), 3.90–3.72(m, 2H), 2.95(t, J=6.9 Hz, 2H), 2.94–2.81(m, 2H), 2.80–2.65(m, 4H), 2.54–2.47(m, 2H), 2.24(s, 3H), 2.24–2.14(m, 2H), 1.74–1.50(m, 3H), 1.34–1.20(m, 2H), 1.25(t, J=7.2 Hz, 3H), 0.96(d, J=6.6 Hz, 3H).

EXAMPLE 1(24)

3-(5-(2-(2-(5-methylpyrazin-2-yl)-5-methyloxazol-4-yl)ethoxy)-3,4-dihydronaphthalen-1-yl)propanoic acid ethyl ester

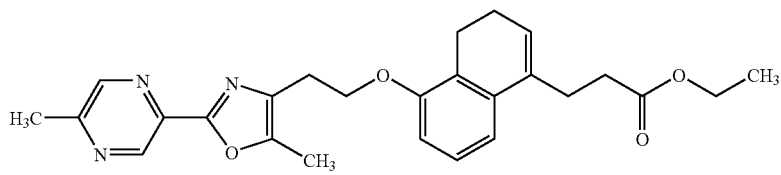

TLC: Rf 0.28 (hexane:ethyl acetate=1:1); NMR(CDCl₃): δ 9.16(m, 1H), 8.51(m, 1H), 7.13(dd, J=7.8, 7.8 Hz, 1H), 6.90(d, J=7.8 Hz, 1H), 6.79(d, J=7.8 Hz, 1H), 5.87(dd, J=4.5, 4.5 Hz, 1H), 4.28(t, J=6.3 Hz, 2H), 4.13(q, J=7.2 Hz, 2H), 3.03(t, J=6.3 Hz, 2H), 2.80–2.60(m, 7H), 2.53–2.46(m, 2H), 2.44(s, 3H), 2.22–2.13(m, 2H), 1.24(t, J=7.2 Hz, 3H).

EXAMPLE 1(25)

3-(5-(2-(2-(1,2,3,6-tetrahydropyridin-1-yl)-5-methylthiazol-4-yl)ethoxy)-3,4-dihydronaphthalen-1-yl) propanoic acid ethyl ester

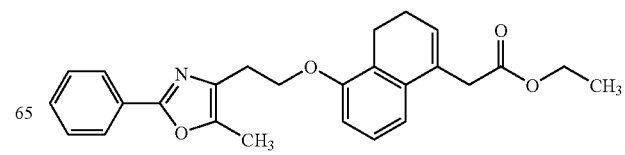

TLC: Rf 0.63 (hexane:ethyl acetate=1:1).

EXAMPLE 1(26)

2-(5-(2-(2-phenyl-5-methyloxazol-4-yl)ethoxy)-3,4-dihydronaphthalen-1-yl)acetic acid ethyl ester TLC: Rf 0.42 (hexane:ethyl acetate=3:1); NMR(CDCl₃): δ 8.01–7.94(m, 2H), 7.48–7.37(m, 3H), 7.11(t, J=8.0 Hz, 1H), 6.82(d, J=8.0 Hz, 1H), 6.80(d, J=8.0 Hz, 1H), 5.98(t, J=4.6 Hz, 1H), 4.25(t, J=6.6 Hz, 2H), 4.12(q, J=7.2 Hz, 2H), 3.42–3.39(m, 2H), 2.99(t, J=7.2 Hz, 2H), 2.76(t, J=8.2 Hz, 2H), 2.37(s, 3H), 2.33–2.19(m, 2H), 1.21(t, J=7.2 Hz, 3H).

EXAMPLE 1(27)

2-(5-(2-(2-(4-methylphenyl)-5-methyloxazol-4-yl)ethoxy)-3,4-dihydronaphthalen-1-yl)acetic acid ethyl ester

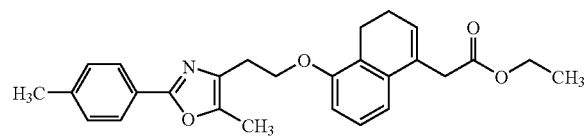

TLC: Rf 0.57 (hexane:ethyl acetate=2:1); NMR(CDCl₃): δ 7.86(d, J=8.1 Hz, 2H), 7.23(d, J=8.1 Hz, 2H), 7.10(dd, J=7.8, 7.8 Hz, 1H), 6.81(m, 2H), 5.97(t, J=4.5 Hz, 1H), 4.24(t, J=6.6 Hz, 2H), 4.13(q, J=7.2 Hz, 2H), 3.46(s, 2H), 2.98(t, J=6.6 Hz, 2H), 2.76(t, J=8.4 Hz, 2H), 2.38(s, 3H), 2.35(s, 3H), 2.27(m, 2H), 1.21(t, J=7.2 Hz, 3H).

EXAMPLE 1(28)

2-(5-(2-(2-isopropyl-5-methyloxazol-4-yl)ethoxy)-3,4-dihydronaphthalen-1-yl)acetic acid ethyl ester

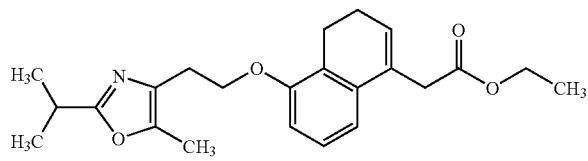

TLC: Rf 0.45 (hexane:ethyl acetate=2:1); NMR (CDCl₃): δ 7.10(dd, J=7.8, 7.8 Hz, 1H), 6.86–6.74(m, 2H), 5.98(dd, J=4.5, 4.5 Hz, 1H), 4.15(q, J=6.9 Hz, 2H), 4.15(t, J=8.4 Hz, 2H), 3.40(d, J=1.2 Hz, 2H), 2.99(sept., J=6.9 Hz, 1H), 2.88(t, J=6.6 Hz, 2H), 2.74(t, J=6.9 Hz, 2H), 2.32–2.20(m, 2H), 2.24(s, 3H), 1.31(d, J=6.9 Hz, 6H), 1.22(t, J=6.9 Hz, 3H).

EXAMPLE 1(29)

2-(5-(2-(2-(4-cyclohexylphenyl)-5-methyloxazol-4-yl)ethoxy)-3,4-dihydronaphthalen-1-yl)acetic acid ethyl ester

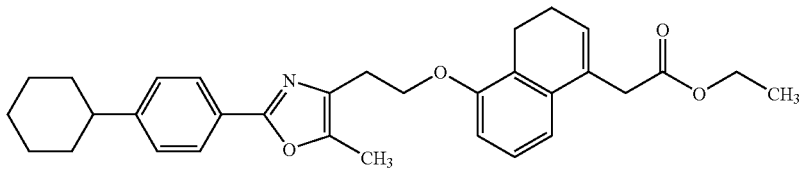

TLC: Rf 0.63 (hexane:ethyl acetate=2:1); NMR(CDCl₃): δ 7.94–7.84(m, 2H), 7.32–7.22(m, 2H), 7.10(dd, J=8.1, 8.1 Hz, 1H), 6.86–6.76(m, 2H), 5.98(t, J=4.5 Hz, 1H), 4.24(t, J=6.6 Hz, 2H), 4.12(q, J=7.2 Hz, 2H), 3.40(d, J=1.2 Hz, 2H), 2.98(t, J=6.6 Hz, 2H), 2.76(t, J=8.1 Hz, 2H), 2.53(m, 1H), 2.35(s, 3H), 2.32–2.20(m, 2H), 1.96–1.70(m, 5H), 1.54–1.26(m, 5H), 1.21(t, J=7.2 Hz, 3H).

EXAMPLE 1(30)

2-(5-(2-(2-(4-methylpiperazin-1-yl)-5-methylthiazol-4-yl)ethoxy)-3,4-dihydronaphthalen-1-yl)acetic acid ethyl ester

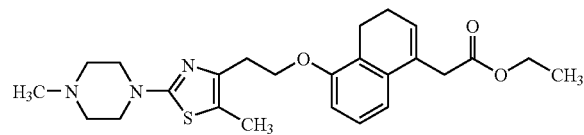

TLC: Rf 0.21 (methanol:ethyl acetate=1:10); NMR (CDCl₃): δ 7.10(dd, J=8.1, 8.1 Hz, 1H), 6.81(d, J=8.1 Hz, 1H), 6.79(d, J=8.1 Hz, 1H), 5.98(brt, 1H), 4.20(t, J=6.9 Hz, 2H), 4.13(q, J=6.9 Hz, 2H), 3.44–3.36(m, 6H), 2.96(t, J=6.9 Hz, 2H), 2.76(dd, J=8.4, 8.4 Hz, 2H), 2.50(m, 4H), 2.33(s, 3H), 2.26(s, 3H), 2.31–2.21(m, 2H), 1.22(t, J=6.9 Hz, 3H).

EXAMPLE 1(31)

2-(5-(2-(2-(piperidin-1-yl)-5-methylthiazol-4-yl)ethoxy)-3,4-dihydronaphthalen-1-yl)acetic acid ethyl ester

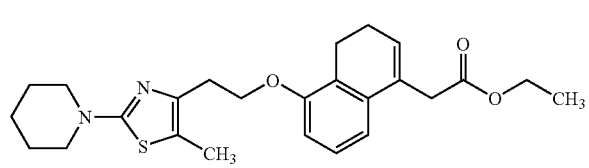

TLC: Rf 0.58 (hexane:ethyl acetate=2:1); NMR(CDCl₃): δ 7.10(dd, J=7.8, 7.8 Hz, 1H), 6.85–6.76(m, 2H), 5.98(dd, J=4.8, 4.8 Hz, 1H), 4.20(t, J=6.6 Hz, 2H), 4.13(q, J=7.2 Hz, 2H), 3.40(m, 2H), 3.36(m, 4H), 2.95(t, J=6.6 Hz, 2H), 2.76(dd, J=8.4, 8.4 Hz, 2H), 2.33–2.20(m, 2H), 2.24(s, 3H), 1.70–1.54(m, 6H), 1.20(t, J=7.2 Hz, 3H).

EXAMPLE 1(32)

5-(5-(2-(2-phenyl-5-methyloxazol-4-yl)ethoxy)-3,4-dihydronaphthalen-1-yl)pentanoic acid methyl ester

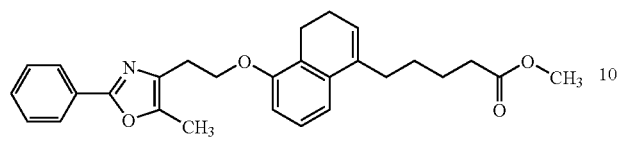

TLC: Rf 0.52 (hexane:ethyl acetate=2:1); NMR(CDCl$_3$): δ 8.02–7.94(m, 2H), 7.48–7.37(m, 3H), 7.12(t, J=8.0 Hz, 1H), 6.87(d, J=8.0 Hz, 1H), 6.79(d, J=8.0 Hz, 1H), 5.84(t, J=4.4 Hz, 1H), 4.25(t, J=6.6 Hz, 2H), 3.65(s, 3H), 2.99(t, J=6.6 Hz, 2H), 2.71(t, J=7.8 Hz, 2H), 2.43(t, J=7.6 Hz, 2H), 2.38(s, 3H), 2.32(t, J=7.8 Hz, 2H), 2.25–2.11(m, 2H), 1.86–1.44(m, 4H).

EXAMPLE 1(33)

5-(5-(2-(2-(4-methylphenyl)-5-methyloxazol-4-yl)ethoxy)-3,4-dihydronaphthalen-1-yl)pentanoic acid methyl ester

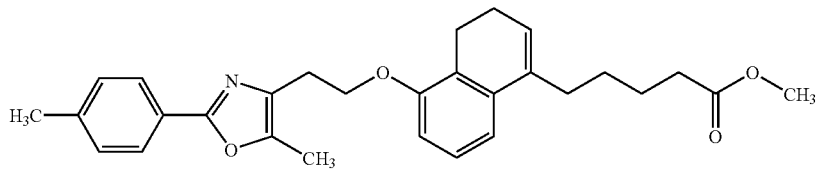

TLC: Rf 0.41 (hexane:ethyl acetate=3:1); NMR(CDCl$_3$): δ 7.85(d, J=8 Hz, 2H), 7.25(d, J=8 Hz, 2H), 7.10(m, 1H), 6.90–6.65(m, 2H), 5.85(t, J=7 Hz, 1H), 4.25(t, J=7 Hz, 2H), 3.65(s, 3H), 3.00(t, J=7 Hz, 2H), 2.70(t, J=8 Hz, 2H), 2.50–2.10(m, 12H), 1.80–1.50(m, 4H).

EXAMPLE 1(34)

5-(5-(2-(2-(1,3-dioxaindan-5-yl)-5-methyloxazol-4-yl)ethoxy)-3,4-dihydronaphthalen-1-yl)pentanoic acid methyl ester

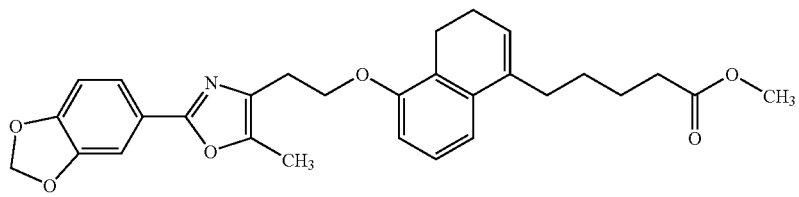

TLC: Rf 0.31 (hexane:ethyl acetate=3:1); NMR(CDCl$_3$): δ 7.55(dd, J=8, 1 Hz, 1H), 7.45(d, J=1Hz, 1H), 7.10(dd, J=7.5, 7.5 Hz, 1H), 6.90–6.85(m, 3H), 6.00(s, 2H), 5.85(t, J=7 Hz, 1H), 4.20(t, J=6.5 Hz, 2H), 3.65(s, 3H), 3.00(t, J=6.5 Hz, 2H), 2.70,(t, J=8 Hz, 2H), 2.50–2.10(m, 9H), 1.80–1.50(m, 4H).

EXAMPLE 1(35)

5-(5-(2-(2-(4-dimethylaminophenyl)-5-methyloxazol-4-yl)ethoxy)-3,4-dihydronaphthalen-1-yl)pentanoic acid methyl ester

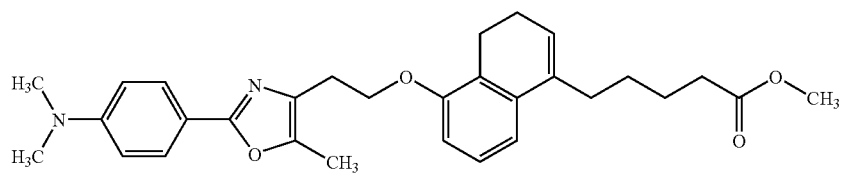

TLC: Rf 0.33 (hexane:ethyl acetate=2:1); NMR(CDCl₃): δ 7.80(d, J=8 Hz, 2H), 7.10(m, 1H), 6.90–6.70(m, 4H), 5.85(m, 1H), 4.20(t, J=6.5 Hz, 2H), 3.65(s, 3H), 3.00(s, 6H), 2.95(m, 2H), 2.70(m, 2H), 2.50–2.10(m, 6H), 1.80–1.50(m, 4H).

EXAMPLE 1(36)

2,2-dimethyl-3-(5-(2-(2-phenyl-5-methyloxazol-4-yl)ethoxy)-3,4-dihydronaphthalen-1-yl)propanoic acid methyl ester

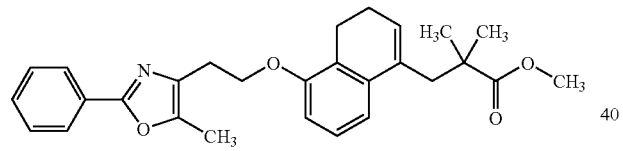

TLC: Rf 0.62 (hexane:ethyl acetate=2:1); NMR(CDCl₃): δ 8.02–7.94(m, 2H), 7.48–7.34(m, 3H), 7.08(t, J=8.1 Hz, ₁H), 6.90(d, J=8.1 Hz, 1H), 6.77(d, J=8.1 Hz, 1H), 5.83(t, J=4.8 Hz, 1H), 4.24(t, J=6.6 Hz, 2H), 3.46(s, 3H), 2.99(t, J=6.6 Hz, 2H), 2.71(s, 2H), 2.68(t, J=5.1 Hz, 2H), 2.37(s, 3H), 2.19–2.09(m, 2H), 1.13(s, 6H).

EXAMPLE 1(37)

2,2-dimethyl-3-(5-(2-(2-(6-dimethylaminopyridin-3-yl)-5-methyloxazol-4-yl)ethoxy)-3,4-dihydronaphthalen-1-yl)propanoic acid methyl ester

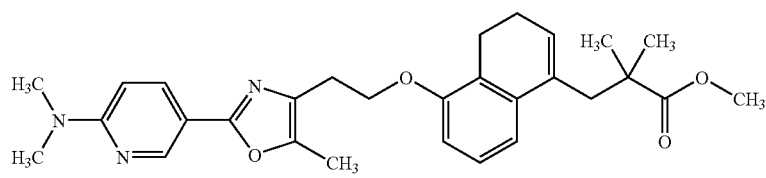

TLC: Rf 0.38 (hexane:ethyl acetate=1:1); NMR(CDCl₃): δ 8.73(d, J=2.4 Hz, 1H), 7.99(dd, J=9.0, 2.4 Hz, 1H), 7.08(dd, J=8.1, 8.1 Hz, 1H), 6.90(d, J=8.1 Hz, 1H), 6.77(d, J=8.1 Hz, 1H), 6.52(d, J=9.0 Hz, 1H), 5.83(t, J=4.5 Hz, 1H), 4.23(t, J=6.6 Hz, 2H), 3.46(s, 3H), 3.14(s, 6H), 2.96(t, J=6.6 Hz, 2H), 2.71(s, 2H), 2.68(t, J=8.1 Hz, 2H), 2.34(s, 3H), 2.17–2.10(m, 2H), 1.13(s, 6H).

EXAMPLE 1(38)

2,2-dimethyl-3-(5-(2-(2-isopropyl-5-methyloxazol-4-yl)ethoxy)-3,4-dihydronaphthalen-1-yl)propanoic acid methyl ester

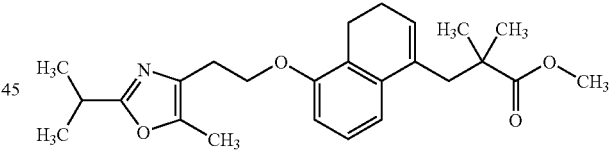

TLC: Rf 0.63 (hexane:ethyl acetate=1:1); NMR(CDCl₃): δ 7.08(dd, J=8.4, 7.8 Hz, 1H), 6.89(d, J=7.8 Hz, 1H), 6.74(d, J=8.4 Hz, 1H), 5.83(m, 1H), 4.16(t, J=6.6 Hz, 2H), 3.46(s, 3H), 2.99(quint., J=7.2 Hz, 1H), 2.89(t, J=6.6 Hz, 2H), 2.71(s, 2H), 2.66(t, J=8.1 Hz, 2H), 2.24(s, 3H), 2.80–2.40 (m, 2H), 1.31(d, J=7.2 Hz, 6H), 1.14(s, 6H).

EXAMPLE 1(39)

2,2-dimethyl-3-(5-(2-(2-(6-(pyridin-1-yl)pyridin-3-yl)-5-methyloxazol-4-yl)ethoxy)-3,4-dihydronaphthalen-1-yl)propanoic acid methyl ester

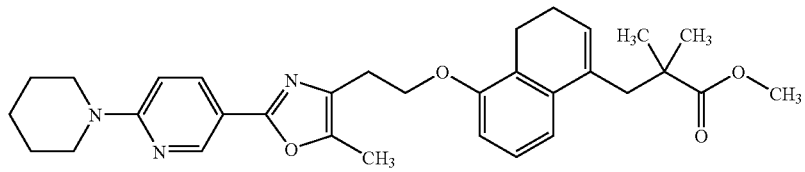

TLC: Rf 0.38 (hexane:ethyl acetate=2:1); NMR(CDCl$_3$): δ 8.73(dd, J=2.4, 0.6 Hz, 1H), 7.98(dd, J=9.0, 2.4 Hz, 1H), 7.08(dd, J=7.8, 7.8 Hz, 1H), 6.90(d, J=7.8 Hz, 1H), 6.77(d, J=7.8 Hz, 1H), 6.65(dd, J=9.0, 0.6 Hz, 1H), 5.83(t, J=4.5 Hz, 1H), 4.22(t, J=6.6 Hz, 2H), 3.68–3.54(m, 4H), 3.46(s, 3H), 2.96(t, J=6.6 Hz, 2H), 2.71(s, 2H), 2.74–2.62(m, 2H), 2.34(s, 3H), 2.20–2.06(m, 2H), 1.78–1.54(m, 6H), 1.13(s, 6H).

EXAMPLE 1(40)

2,2-dimethyl-3-(5-(2-(2-(6-(morpholin-4-yl)pyridin-3-yl)-5-methyloxazol-4-yl)ethoxy)-3,4-dihydronaphthalen-1-yl)propanoic acid methyl ester

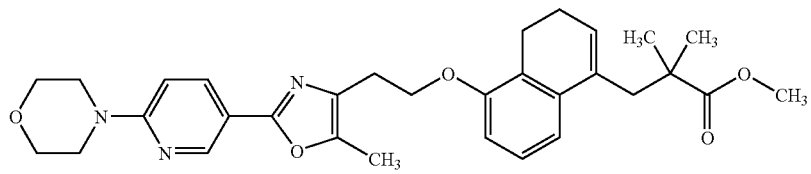

TLC: Rf 0.65 (chloroform:methanol=8:1); NMR(CDCl$_3$): δ 8.76(dd, J=2.4, 0.9 Hz, 1H), 8.04(dd, J=9.0, 2.4 Hz, 1H), 7.08(dd, J=7.8, 7.8 Hz, 1H), 6.90(d, J=7.8 Hz, 1H), 6.77(d, J=7.8 Hz, 1H), 6.65(dd, J=9.0, 0.9 Hz, 1H), 5.83(t, J=4.5 Hz, 1H), 4.23(t, J=6.6 Hz, 2H), 3.86–3.78(m, 4H), 3.64–3.54(m, 4H), 3.46(s, 3H), 2.97(t, J=6.6 Hz, 2H), 2.76–2.62(m, 4H), 2.35(s, 3H), 2.13(m, 2H), 1.78–1.54(m, 2H), 1.14(s, 6H).

EXAMPLE 1(41)

2,2-dimethyl-3-(5-(2-(2-(6-methylpyridin-3-yl)-5-methyloxazol-4-yl)ethoxy)-3,4-dihydronaphthalen-1-yl)propanoic acid methyl ester

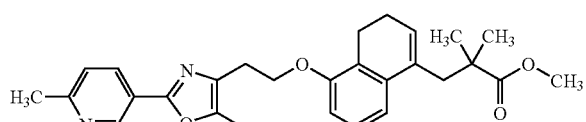

TLC: Rf 0.53 (hexane:ethyl acetate=1:1); NMR(CDCl$_3$): δ 9.08(d, J=1.8 Hz, 1H), 8.12(dd, J=8.1, 1.8 Hz, 1H), 7.22(d, J=8.1 Hz, 1H), 7.08(dd, J=8.1, 8.1 Hz, 1H), 6.90(d, J=8.1 Hz, 1H), 6.77(d, J=8.1 Hz, 1H), 5.83(t, J=4.5 Hz, 1H), 4.24(t, J=6.6 Hz, 2H), 2.99(t, J=6.6 Hz, 2H), 2.71(s, 2H), 2.67(t, J=8.1 Hz, 2H), 2.61(s, 3H), 2.38(s, 3H), 2.14(m, 2H), 1.13(s, 6H).

EXAMPLE 1(42)

2,2-dimethyl-3-(5-(2-(2-(morpholin-4-yl)-5-methylthiazol-4-yl)ethoxy)-3,4-dihydronaphthalen-1-yl)propanoic acid methyl ester

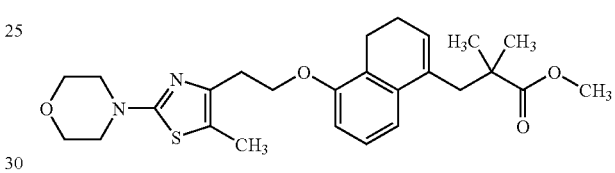

TLC: Rf 0.40 (hexane:ethyl acetate=5:1); NMR(CDCl$_3$): δ 7.08(dd, J=8.1, 7.8 Hz, 1H), 6.89(d, J=7.8 Hz, 1H), 6.76(d, J=8.1 Hz, 1H), 5.83(t, J=4.8 Hz, 1H), 4.20(t, J=6.9 Hz, 2H), 3.79(t, J=4.8 Hz, 4H), 3.37(t, J=4.8 Hz, 4H), 2.96(t, J=6.9 Hz, 2H), 2.71(s, 2H), 2.67(t, J=7.2 Hz, 2H), 2.27(s, 3H), 2.17–2.10(m, 2H), 1.14(s, 6H).

EXAMPLE 1(43)

2,2-dimethyl-3-(5-(2-(2-(piperidin-1-yl)-5-methylthiazol-4-yl)ethoxy)-3,4-dihydronaphthalen-1-yl)propanoic acid methyl ester

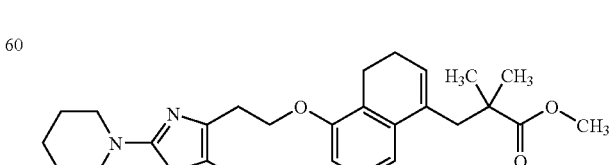

TLC: Rf 0.90 (hexane:ethyl acetate=1:1); NMR(CDCl$_3$): δ 7.07(dd, J=7.8, 7.8 Hz, 1H), 6.89(d, J=7.8 Hz, 1H), 6.76(d, J=8.1 Hz, 1H), 5.83(t, J=4.8 Hz, 1H), 4.20(t, J=6.6 Hz, 2H), 3.46(s, 3H), 3.36(m, 4H), 2.95(t, J=6.6 Hz, 2H), 2.71(s, 2H), 2.68(t, J=8.4 Hz, 2H), 2.25(s, 3H), 2.17–2.10(m, 2H), 1.61 (m, 6H), 1.14(s, 6H).

EXAMPLE 1(44)

2,2-dimethyl-3-(5-(2-(2-(thiomorpholin-4-yl)-5-methylthiazol-4-yl)ethoxy)-3,4-dihydronaphthalen-1-yl)propanoic acid methyl ester

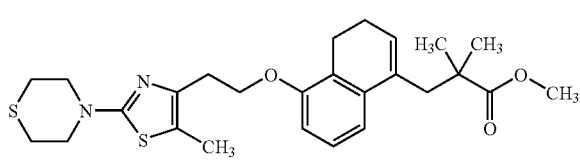

TLC: Rf 0.76 (hexane:ethyl acetate=1:1); NMR(CDCl$_3$): δ 7.08(dd, J=8.1, 7.8 Hz, 1H), 6.89(d, J=7.8 Hz, 1H), 6.75(d, J=8.1 Hz, 1H), 5.83(t, J=4.8 Hz, 1H), 4.19(t, J=6.6 Hz, 2H), 3.76–3.73(m, 4H), 3.47(s, 3H), 2.94(t, J=6.6 Hz, 2H), 2.71–2.67(m, 8H), 2.25(s, 3H), 2.17–2.10(m, 2H), 1.14(s, 6H).

EXAMPLE 1(45)

2,2-dimethyl-5-(5-(2-(2-phenyl-5-methyloxazol-4-yl)ethoxy)-3,4-dihydronaphthalen-1-yl)pentanoic acid methyl ester

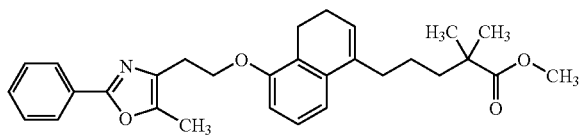

TLC: Rf 0.68 (hexane:ethyl acetate=2:1); NMR(CDCl$_3$): δ 8.02–7.94(m, 2H), 7.48–7.37(m, 3H), 7.11(t, J=7.8 Hz, 1H), 6.85(d, J=7.8 Hz, 1H), 6.78(d, J=7.8 Hz, 1H), 5.82(t, J=4.4 Hz, 1H), 4.25(t, J=6.6 Hz, 2H), 3.59(s, 3H), 2.99(t, J=6.6 Hz, 2H), 2.71(t, J=7.6 Hz, 2H), 2.44–2.32(m, 2H), 2.24–2.11(m, 2H), 1.65–1.33(m, 4H), 1.14(s, 6H).

EXAMPLE 1(46)

2-benzyloxy-3-(5-(2-(2-(4-methylphenyl)-5-methyloxazol-4-yl)ethoxy)-3,4-dihydronaphthalen-1-yl)propanoic acid methyl ester

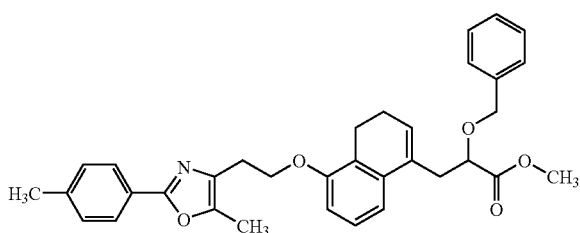

TLC: Rf 0.27 (hexane:ethyl acetate=4:1); NMR(CDCl$_3$): δ 7.87(m, 2H), 7.26–7.18(m, 7H), 7.08(dd, J=8.1, 8.1 Hz, 1H), 6.84(d, J=8.1 Hz, 1H), 6.79(d, J=8.1 Hz, 1H), 5.95(dd, J=4.5, 4.5 Hz, 1H), 4.63(d, J=11.7 Hz, 1H), 4.34(d, J=11.7 Hz, 1H), 4.26(t, J=6.6 Hz, 2H), 4.16(dd, J=9.0, 3.6 Hz, 1H), 3.70(s, 3H), 3.04–2.58(m, 6H), 2.38(s, 3H), 2.37(s, 3H), 2.24–2.14(m, 2H).

EXAMPLE 2

3-(5-(2-(2-(4-methylphenyl)-5-methyloxazol-4-yl)ethoxy)-3,4-dihydronaphthalen-1-yl)propanoic acid

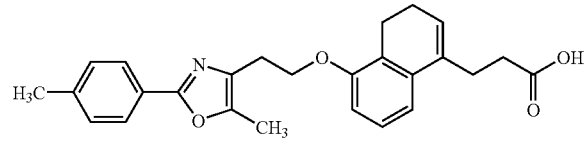

The compound (950 mg) prepared in Example 1 was dissolved in methanol (8.0 ml) and tetrahydrofuran (8.0 ml), and 2N aqueous sodium hydroxide solution (3.3 ml) was added thereto, followed by stirring at room temperature overnight. The reaction mixture was acidified with 1N hydrochloric acid, and extracted with a mixed solvent of ethyl acetate and tetrahydrofuran. The extract was washed with saturated saline, dried with anhydrous magnesium sulfate, and concentrated under reduced pressure. The residue was recrystallized with a mixed solvent of ethyl acetate and tetrahydrofuran to thereby obtain the compound of the present invention (745 mg) having the following physical data.

TLC: Rf 0.63 (chloroform:methanol=8:1); NMR(DMSO-d$_6$): δ 7.79(d, J=8.2 Hz, 2H), 7.29(d, J=8.2 Hz, 2H), 7.14(dd, J=8.0, 8.0 Hz, 1H), 6.97–6.78(m, 2H), 5.84(brt, 1H), 4.19(t, J=5.8 Hz, 2H), 2.91(t, J=5.8 Hz, 2H), 2.75–2.20(m, 6H), 2.33(s, 3H), 2.36(s, 3H), 2.20–1.94(m, 2H).

EXAMPLE 2(1) TO EXAMPLE 2(41)

The following compounds of the present invention were obtained in the same manner as in Example 2 using the compound prepared in Example 1 (1) to Example 1(9), Example 1 (11) to Example 1(27) and Example 1(32) to Example 1(46) instead of the compound prepared in Example 1, if necessary followed by converting to a corresponding salt by a known method.

EXAMPLE 2(1)

3-(5-(2-(2-phenyl-5-methyloxazol-4-yl)ethoxy)-3,4-dihydronaphthalen-1-yl)propanoic acid

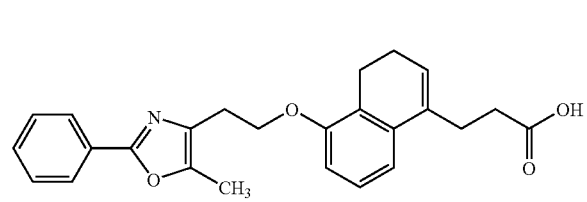

TLC: Rf 0.51 (chloroform:methanol=10:1); NMR (CDCl₃): δ 8.02–7.94(m, 2H), 7.46–7.37(m, 3H), 7.13(t, J=8.0 Hz, 1H), 6.88(d, J=8.0 Hz, 1H), 6.81(d, J=8.0 Hz, 1H), 5.89(brt, J=4.6 Hz, 1H), 4.25(t, J=6.6 Hz, 2H), 3.00(t, J=6.6 Hz, 2H), 2.83–2.52(m, 6H), 2.37(s, 3H), 2.27–2.12(m, 2H).

EXAMPLE 2(2)

3-(5-(2-(2-(6-dimethylaminopyridin-3-yl)-5-methyloxazol-4-yl)ethoxy)-3,4-dihydronaphthalen-1-yl)propanoic acid

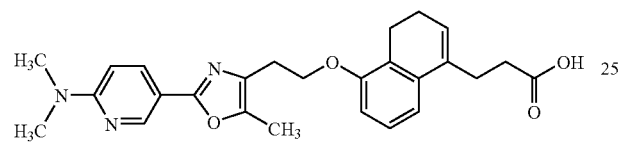

TLC: Rf 0.47 (chloroform:methanol=10:1); NMR (CDCl₃): δ 8.73(dd, J=2.4, 0.4 Hz, 1H), 8.00(dd, J=9.0, 2.4 Hz, 1H), 7.12(t, J=8.0 Hz, 1H), 6.89(d, J=8.0 Hz, 1H), 6.80(d, J=8.0 Hz, 1H), 6.53(dd, J=9.0, 0.4 Hz, 1H), 5.89(brt, J=4.4 Hz, 1H), 4.23(t, J=6.6 Hz, 2H), 3.14(s, 6H), 2.97(t, J=6.6 Hz, 2H), 2.83–2.52(m, 6H), 2.34(s, 3H), 2.26–2.12(m, 2H).

EXAMPLE 2(3)

3-(5-(2-(2-(1,3-dioxaindan-5-yl)-5-methyloxazol-4-yl)ethoxy)-3,4-dihydronaphthalen-1-yl)propanoic acid

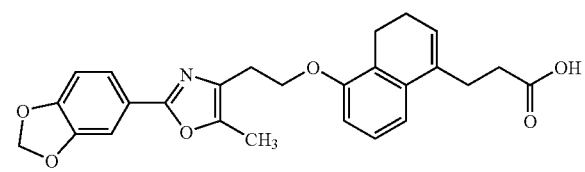

TLC: Rf 0.61 (chloroform:methanol=8:1); NMR(DMSO-d₆): δ 7.43(d, J=8.3 Hz, 1H), 7.35(s, 1H), 7.14(dd, J=8.0, 8.0 Hz, 1H), 7.01(d, J=8.3 Hz, 1H), 6.96–6.75(m, 2H), 6.09(s, 2H), 5.84(brt, 1H), 4.18(t, J=6.0 Hz, 2H), 2.90(t, J=6.0 Hz, 2H), 2.75–2.20(m, 6H), 2.31(s, 3H), 2.20–1.94(m, 2H).

EXAMPLE 2(4)

3-(5-(2-(2-(4-t-butylphenyl)-5-methyloxazol-4-yl)ethoxy)-3,4-dihydronaphthalen-1-yl)propanoic acid

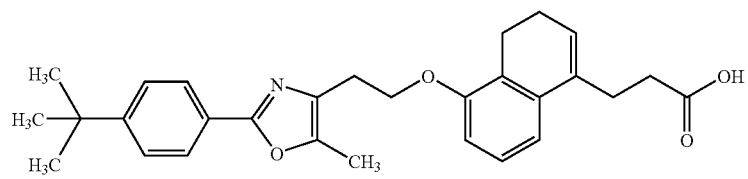

TLC: Rf 0.47 (chloroform:methanol=10:1); NMR (CDCl₃): δ 7.90(d, J=8.6 Hz, 2H), 7.44(d, J=8.6 Hz, 2H), 7.12(dd, J=7.8, 7.6 Hz, 1H), 6.88(d, J=7.6 Hz, 1H), 6.80(d, J=7.8 Hz, 1H), 5.88(t, J=6.6 Hz, 1H), 4.24(t, J=6.4 Hz, 2H), 2.99(t, J=6.4 Hz, 2H), 2.84–2.50(m, 6H), 2.35(s, 3H), 2.19(m, 2H), 1.33(s, 9H).

EXAMPLE 2(5)

3-(5-(2-(2-(6-(morpholin-4-yl)pyridin-3-yl)-5-methyloxazol-4-yl)ethoxy)-3,4-dihydronaphthalen-1-yl)propanoic acid

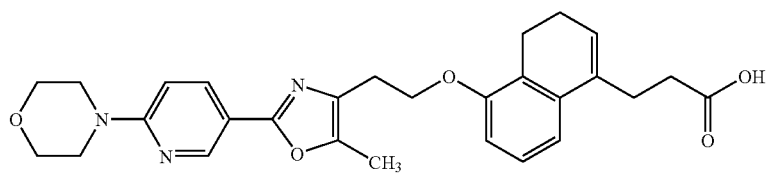

TLC: Rf 0.32 (chloroform:methanol=10:1); NMR (DMSO-d₆): δ 8.61(d, J=2.4 Hz, 1H), 7.97(dd, J=8.8, 2.4 Hz, 1H), 7.13(dd, J=8.4, 7.4 Hz, 1H), 6.96–6.82(m, 3H), 5.84(t, J=4.4 Hz, 1H), 4.17(t, J=6.4 Hz, 2H), 3.68(m, 4H), 3.53(m, 4H), 2.89(t, J=6.4 Hz, 2H), 2.69–2.45(m, 4H), 2.43–2.28(m, 2H), 2.31(s, 3H), 2.10(m, 2H).

EXAMPLE 2(6)

3-(5-(2-(2-(4-dimethylaminophenyl)-5-methyloxazol-4-yl)ethoxy)-3,4-dihydronaphthalen-1-yl)propanoic acid

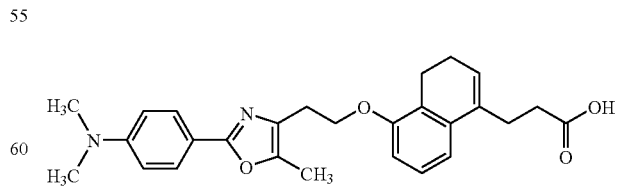

TLC: Rf 0.50 (chloroform:methanol=9:1); NMR(CDCl₃): δ 7.80(d, J=9 Hz, 2H), 7.15(m, 1H), 6.90–6.70(m, 4H), 5.90(t, J=4 Hz, 1H), 4.25(t, J=7 Hz, 2H), 3.00(s, 6H), 2.95(t, J=7 Hz, 2H), 2.80–2.50(m, 6H), 2.35(s, 3H), 2.20(m, 2H).

EXAMPLE 2(7)

3-(5-(2-(2-isopropyl-5-methyloxazol-4-yl)ethoxy)-3,4-dihydronaphthalen-1-yl)propanoic acid

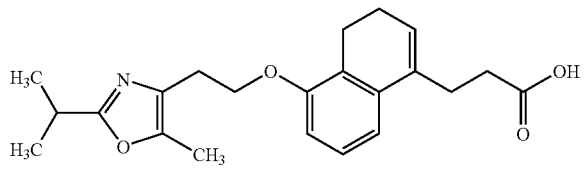

TLC: Rf 0.43 (chloroform:methanol=9:1); NMR(CDCl$_3$): δ 7.15(dd, J=7.5, 7.5 Hz, 1H), 6.85(d, J=7.5 Hz, 1H), 6.80(d, J=7.5 Hz, 1H), 5.90(t, J=4 Hz, 1H), 4.20(t, J=6 Hz, 2H), 3.00(m, 1H), 2.90(t, J=6 Hz, 2H), 2.75(m, 2H), 2.65(t, J=8.5 Hz, 2H), 2.55(t, J=8.5 Hz, 2H), 2.20(s, 3H), 2.20(m, 2H), 1.30(d, J=6 Hz, 6H).

EXAMPLE 2(8)

3-(5-(2-(2-(4-trifluoromethylphenyl)-5-methyloxazol-4-yl)ethoxy)-3,4-dihydronaphthalen-1-yl)propanoic acid

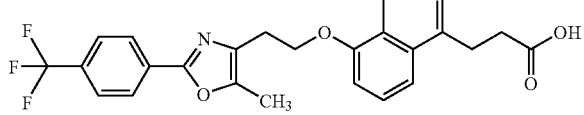

TLC: Rf 0.60 (chloroform:methanol=9:1); NMR(DMSO-d$_6$): δ 8.10(d, J=8 Hz, 2H), 7.85(d, J=8 Hz, 2H), 7.15(dd, J=8, 8 Hz, 1H), 6.95–6.85(m, 2H), 5.85(m, 1H), 4.20(t, J=6 Hz, 2H), 2.95(t, J=6 Hz, 2H), 2.70–2.50(m, 4H), 2.40(s, 3H), 2.40(m, 2H), 2.10(m, 2H).

EXAMPLE 2(9)

3-(5-(2-(2-(4-trifluoromethyloxyphenyl)-5-methyloxazol-4-yl)ethoxy)-3,4-dihydronaphthalen-1-yl)propanoic acid

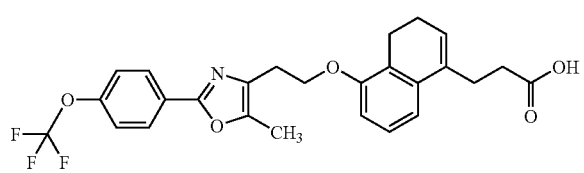

TLC: Rf 0.51 (chloroform:methanol=9:1); NMR(DMSO-d$_6$): δ 8.00(d, J=9 Hz, 2H), 7.50(d, J=9 Hz, 2H), 7.15(dd, J=8, 8 Hz, 1H), 6.95–6.85(m, 2H), 5.85(m, 1H), 4.20(t, J=6 Hz, 2H), 2.95(t, J=6 Hz, 2H), 2.70–2.50(m, 4H), 2.40(m, 2H), 2.40(s, 3H), 2.10(m, 2H).

EXAMPLE 2(10)

3-(5-(2-(2-(4-chlorophenyl)-5-methyloxazol-4-yl)ethoxy)-3,4-dihydronaphthalen-1-yl)propanoic acid

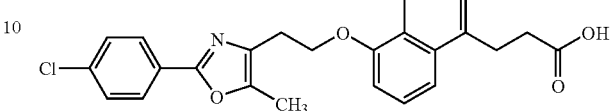

TLC: Rf 0.60 (chloroform:methanol=9:1); NMR(DMSO-d$_6$): δ 7.95(d, J=8 Hz, 2H), 7.60(d, J=8 Hz, 2H), 7.15(dd, J=8, 8 Hz, 1H), 6.95(d, J=8 Hz, 1H), 6.90(d, J=8 Hz, 1H), 5.85(t, J=4 Hz, 1H), 4.20(t, J=6 Hz, 2H), 2.95(t, J=6 Hz, 2H), 2.65–2.50(m, 6H), 2.40(s, 3H), 2.10(m, 2H).

EXAMPLE 2(11)

3-(5-(2-(2-(4-methylthiophenyl)-5-methyloxazol-4-yl)ethoxy)-3,4-dihydronaphthalen-1-yl)propanoic acid

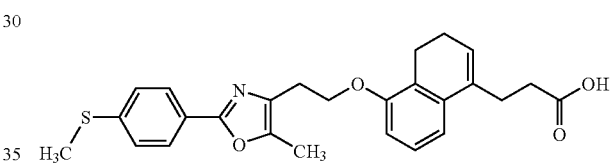

TLC: Rf 0.49 (chloroform:methanol=9:1); NMR(DMSO-d$_6$): δ 7.80(d, J=8 Hz, 2H), 7.35(d, J=8 Hz, 2H), 7.15(dd, J=8, 8 Hz, 1H), 6.95(d, J=8 Hz, 1H), 6.90(d, J=8 Hz, 1H), 5.85(t, J=4 Hz, 1H), 4.20(t, J=7 Hz, 2H), 2.95(t, J=7 Hz, 2H), 2.65–2.55(m, 4H), 2.50(s, 3H), 2.40(m, 2H), 2.35(s, 3H), 2.10(m, 2H).

EXAMPLE 2(12)

3-(5-(2-(2-(4-isopropylphenyl)-5-methyloxazol-4-yl)ethoxy)-3,4-dihydronaphthalen-1-yl)propanoic acid

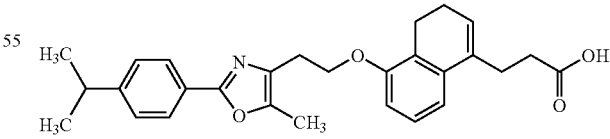

TLC: Rf 0.58 (chloroform:methanol=9:1); NMR(DMSO-d$_6$): δ 7.80(d, J=8 Hz, 2H), 7.35(d, J=8 Hz, 2H), 7.15(dd, J=8, 8 Hz, 1H), 6.90(d, J=8 Hz, 1H), 6.85(d, J=8 Hz, 1H), 5.85(t, J=4 Hz, 1H), 4.20(t, J=6 Hz, 2H), 3.00–2.90(m, 3H), 2.65–2.50(m, 4H), 2.40–2.35(m, 2H), 2.35(s, 3H), 2.10(m, 2H), 1.20(d, J=8 Hz, 6H).

EXAMPLE 2(13)

3-(5-(2-(2-(4-propylphenyl)-5-methyloxazol-4-yl)ethoxy)-3,4-dihydronaphthalen-1-yl)propanoic acid

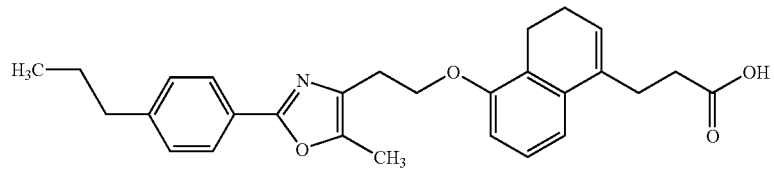

TLC: Rf 0.53 (chloroform:methanol=9:1); NMR(DMSO-d$_6$): δ 7.80(d, J=8 Hz, 2H), 7.30(d, J=8 Hz, 2H), 7.15(dd, J=8, 8 Hz, 1H), 6.90(d, J=8 Hz, 1H), 6.85(d, J=8 Hz, 1H), 5.85(t, J=4 Hz, 1H), 4.20(t, J=6 Hz, 2H), 2.95(t, J=6 Hz, 2H), 2.65–2.50(m, 8H), 2.40–2.35(m, 2H), 2.35(s, 3H), 2.10(m, 2H), 0.90(t, J=8 Hz, 3H).

EXAMPLE 2(14)

3-(5-(2-(2-(2,2-difluoro-1,3-dioxaindan-5-yl)-5-methyloxazol-4-yl)ethoxy)-3,4-dihydronaphthalen-1-yl)propanoic acid

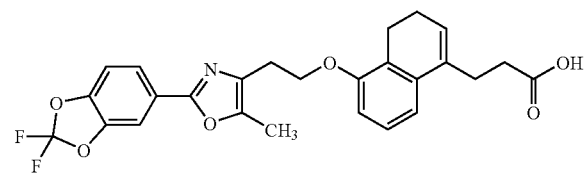

TLC: Rf 0.51 (chloroform:methanol=9:1); NMR(DMSO-d$_6$): δ 7.85(m, 1H), 7.80(m, 1H), 7.55(d, J=8 Hz, 1H), 7.15(dd, J=8, 8 Hz, 1H), 6.90(d, J=8 Hz, 1H), 6.85(d, J=8 Hz, 1H), 5.85(t, J=4 Hz, 1H), 4.20(t, J=7 Hz, 2H), 2.95(t, J=7 Hz, 2H), 2.65–2.50(m, 4H), 2.40–2.35(m, 2H), 2.35(s, 3H), 2.10(m, 2H).

EXAMPLE 2(15)

3-(5-(2-(2-(6-diethylaminopyridin-3-yl)-5-methyloxazol-4-yl)ethoxy)-3,4-dihydronaphthalen-1-yl)propanoic acid

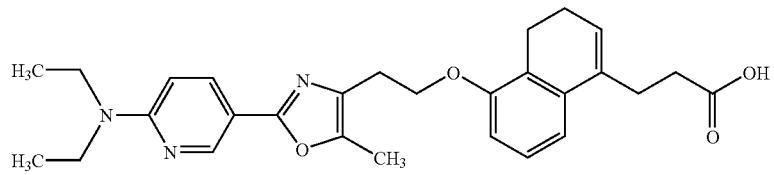

TLC: Rf 0.54 (chloroform:methanol=8:1); NMR(DMSO-d$_6$): δ 8.56(d, J=2.4 Hz, 1H), 7.88(dd, J=9.0, 2.4 Hz, 1H), 7.13(dd, J=7.8, 7.8 Hz, 1H), 6.89(d, J=7.8 Hz, 1H), 6.86(d, J=7.8 Hz, 1H), 6.65(d, J=9.0 Hz, 1H), 5.84(dd, J=4.2, 4.2 Hz, 1H), 4.17(t, J=6.3 Hz, 2H), 3.51(q, J=6.9 Hz, 4H), 3.32(brs, 1H), 2.88(t, J=6.9 Hz, 2H), 2.70–2.46(m, 4H), 2.36(t, J=7.2 Hz, 2H), 2.30(s, 3H), 2.18–2.00(m, 2H), 1.10(t, J=6.9 Hz, 6H).

EXAMPLE 2(16)

3-(5-(2-(2-(piperidin-1-yl)-5-methylthiazol-4-yl)ethoxy)-3,4-dihydronaphthalen-1-yl)propanoic acid hydrochloride

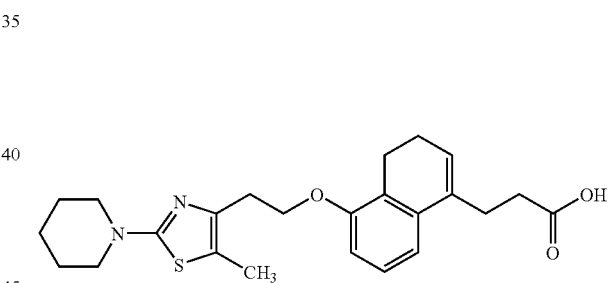

TLC: Rf 0.55 (chloroform:methanol=9:1); NMR(DMSO-d$_6$): δ 12.10(br, 1H), 7.13(t, J=8.1 Hz, 1H), 6.87(d, J=8.1 Hz, 1H), 6.85(d, J=8.1 Hz, 1H), 5.85(t, J=4.5 Hz, 1H), 4.13(t, J=6.6 Hz, 2H), 3.39–3.22(m, 4H), 2.83(t, J=6.6 Hz, 2H), 2.61(t, J=7.2 Hz, 2H), 2.55(t, J=7.8 Hz, 2H), 2.36(t, J=7.8 Hz, 2H), 2.18(s, 3H), 2.14–2.04(m, 2H), 1.58–1.48(m, 6H).

EXAMPLE 2(17)

3-(5-(2-(2-(4-methylpiperazin-1-yl)-5-methylthiazol-4-yl)ethoxy)-3,4-dihydronaphthalen-1-yl)propanoic acid hydrochloride

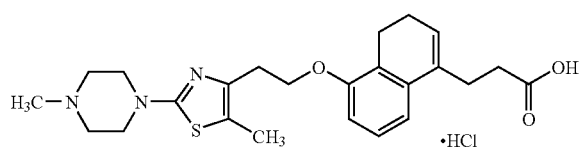

TLC: Rf 0.30 (chloroform:methanol=9:1); NMR(DMSO-d$_6$): δ 12.05(br, 1H), 7.13(t, J=8.1 Hz, 1H), 6.86(d, J=8.1 Hz, 1H), 6.85(d, J=8.1 Hz, 1H), 5.85(t, J=4.2 Hz, 1H), 4.13(t, J=6.6 Hz, 2H), 3.27(t, J=4.8 Hz, 4H), 2.84(t, J=6.6 Hz, 2H), 2.61(t, J=7.5 Hz, 2H), 2.55(t, J=8.1 Hz, 2H), 2.41–2.32(m, 6H), 2.19(s, 6H), 2.14–2.04(m, 2H).

EXAMPLE 2(18)

3-(5-(2-(2-(morpholin-4-yl)-5-methylthiazol-4-yl)ethoxy)-3,4-dihydronaphthalen-1-yl)propanoic acid hydrochloride

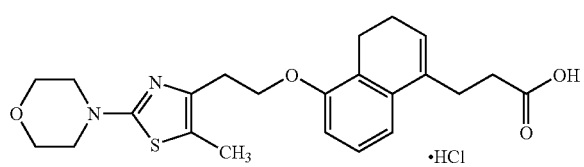

TLC: Rf 0.45 (chloroform:methanol=9:1); NMR(DMSO-d$_6$): δ 12.02(br, 1H), 7.13(t, J=7.8 Hz, 1H), 6.86(d, J=7.8 Hz, 1H), 6.85(d, J=7.8 Hz, 1H), 5.85(t, J=4.2 Hz, 1H), 4.14(t, J=6.3 Hz, 2H), 3.66(t, J=4.8 Hz, 4H), 3.25(t, J=4.8 Hz, 4H), 2.85(t, J=6.3 Hz, 2H), 2.61(t, J=7.5 Hz, 2H), 2.55(t, J=8.1 Hz, 2H), 2.36(t, J=8.1 Hz, 2H), 2.20(s, 3H), 2.14–2.04(m, 2H).

EXAMPLE 2(19)

3-(5-(2-(2-(thiomorpholin-4-yl)-5-methylthiazol-4-yl)ethoxy)-3,4-dihydronaphthalen-1-yl)propanoic acid hydrochloride

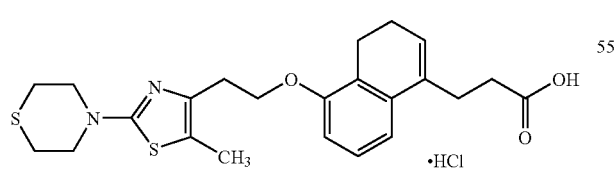

TLC: Rf 0.45 (chloroform:methanol=9:1); NMR(DMSO-d$_6$): δ 12.09(br, 1H), 7.13(t, J=7.8 Hz, 1H), 6.86(d, J=7.8 Hz, 1H), 6.85(d, J=7.8 Hz, 1H), 5.85(t, J=4.2 Hz, 1H), 4.14(t, J=6.6 Hz, 2H), 3.67–3.58(m, 4H), 2.84(t, J=6.6 Hz, 2H), 2.66–2.49(m, 8H), 2.36(t, J=8.1 Hz, 2H), 2.19(s, 3H), 2.15–2.05(m, 2H).

EXAMPLE 2(20)

3-(5-(2-(2-(6-methylpyridin-3-yl)-5-methyloxazol-4-yl)ethoxy)-3,4-dihydronaphthalen-1-yl)propanoic acid hydrochloride

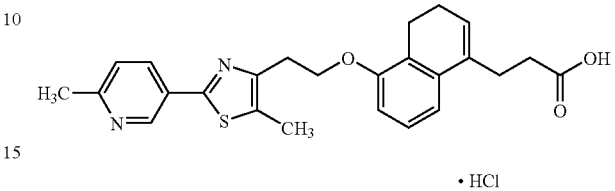

TLC: Rf 0.48 (chloroform:methanol=9:1); NMR(DMSO-d$_6$): δ 12.09(br, 1H), 8.94(d, J=2.1 Hz, 1H), 8.11(dd, J=8.1, 2.1 Hz, 1H), 7.37(d, J=8.1 Hz, 1H), 7.14(t, J=8.1 Hz, 1H), 6.90(d, J=8.1 Hz, 1H), 6.85(d, J=8.1 Hz, 1H), 5.84(t, J=4.2 Hz, 1H), 4.20(t, J=6.0 Hz, 2H), 2.93(t, J=6.0 Hz, 2H), 2.61(t, J=7.5 Hz, 2H), 2.56(t, J=8.4 Hz, 2H), 2.51(s, 3H), 2.40(t, J=7.5 Hz, 2H), 2.35(s, 3H), 2.14–2.04(m, 2H).

EXAMPLE 2(21)

3-(5-(2-(2-(1,5-dimethylpyrazol-3-yl)-5-methyloxazol-4-yl)ethoxy)-3,4-dihydronaphthalen-1-yl)propanoic acid hydrochloride

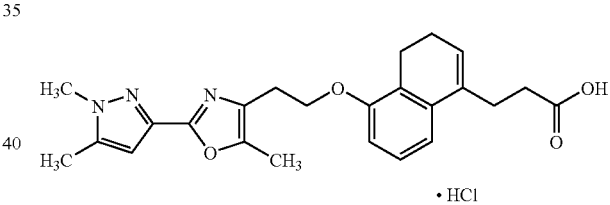

TLC: Rf 0.39 (chloroform:methanol=9:1); NMR(DMSO-d$_6$): δ 12.09(br, 1H), 7.14(t, J=8.1 Hz, 1H), 6.89(d, J=8.1 Hz, 1H), 6.86(d, J=8.1 Hz, 1H), 6.45(s, 1H), 5.84(t, J=4.2 Hz, 1H), 4.17(t, J=6.3 Hz, 2H), 3.76(s, 3H), 2.88(t, J=6.3 Hz, 2H), 2.61(t, J=7.5 Hz, 2H), 2.54(t, J=7.8 Hz, 2H), 2.36(t, J=7.5 Hz, 2H), 2.28(s, 3H), 2.27(s, 3H), 2.14–2.04(m, 2H).

EXAMPLE 2(22)

3-(5-(2-(2-(4-methylpiperidin-1-yl)-5-methylthiazol-4-yl)ethoxy)-3,4-dihydronaphthalen-1-yl)propanoic acid

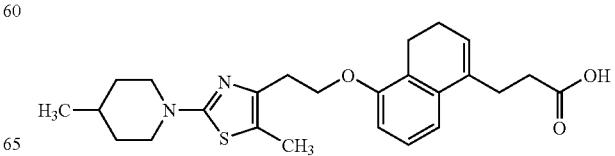

TLC: Rf 0.55 (ethyl acetate); NMR(DMSO-d$_6$): δ 7.04(t, J=7.8 Hz, 1H), 6.77(d, J=7.8 Hz, 1H), 6.76(d, J=7.8 Hz, 1H), 5.78–5.72(m, 1H), 4.04(t, J=6.6 Hz, 2H), 3.70–3.58(m, 2H), 2.84–2.74(m, 2H), 2.80(bs, 1H), 2.74(t, J=6.6 Hz, 2H), 2.55–2.40(m, 4H), 2.30–2.23(m, 2H), 2.08(s, 3H), 2.05–1.95(m, 2H), 1.60–1.35(m, 3H), 1.14–0.94(m, 2H), 0.80(d. J=6.6 Hz, 3H).

EXAMPLE 2(23)

3-(5-(2-(2-(5-methylpyrazin-2-yl)-5-methyloxazol-4-yl)ethoxy)-3,4-dihydronaphthalen-1-yl)propanoic acid

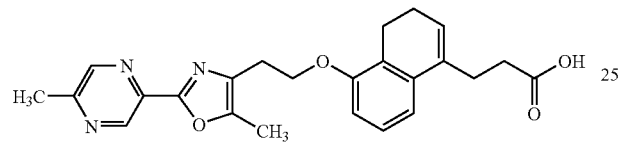

TLC: Rf 0.51 (chloroform:methanol=10:1); NMR (DMSO-d$_6$): δ 12.08(br, 1H), 9.06(m, 1H), 8.60(m, 1H), 7.14(dd, J=8.1, 8.1 Hz, 1H), 6.90(d, J=8.1 Hz, 1H), 6.86(d, J=8.1 Hz, 1H), 5.84(dd, J=4.5, 4.5 Hz, 1H), 4.22(t, J=6.3 Hz, 2H), 2.97(t, J=6.3 Hz, 2H), 2.65–2.52(m, 7H), 2.38(s, 3H), 2.40–2.32(m, 2H), 2.13–2.04(m, 2H).

EXAMPLE 2(24)

3-(5-(2-(2-(1,2,3,6-tetrahydropyridin-1-yl)-5-methylthiazol-4-yl)ethoxy)-3,4-dihydronaphthalen-1-yl)propanoic acid

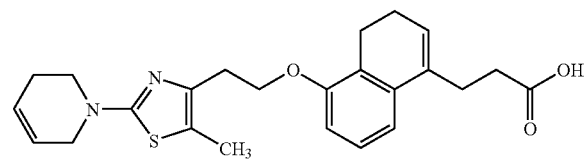

TLC: Rf 0.40 (chloroform:methanol=9:1); NMR(CDCl$_3$): δ 7.12(t, J=7.8 Hz, 1H), 6.87(d, J=7.8 Hz, 1H), 6.80(d, J=7.8 Hz, 1H), 5.92–5.84(m, 2H), 5.78–5.70(m, 1H), 4.21(t, J=6.9 Hz, 2H), 3.86(dt, J=5.4, 2.7 Hz, 2H), 3.54(t, J=5.7 Hz, 2H), 2.97(t, J=6.9 Hz, 2H), 2.80–1.60(br, 1H), 2.80–2.72(m, 2H), 2.70(t, J=8.1 Hz, 2H), 2.60–2.54(m, 2H), 2.30–2.18(m, 4H), 2.26(s, 3H).

EXAMPLE 2(25)

2-(5-(2-(2-phenyl-5-methyloxazol-4-yl)ethoxy)-3,4-dihydronaphthalen-1-yl)acetic acid

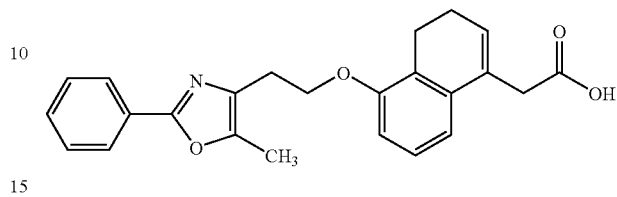

TLC: Rf 0.54 (chloroform:methanol=10:1); NMR (CDCl$_3$): δ 8.01–7.92(m, 2H), 7.48–7.36(m, 3H), 7.09(t, J=8.0 Hz, 1H), 6.83(d, J=8.0 Hz, 1H), 6.76(d, J=8.0 Hz, 1H), 6.00(t, J=4.8 Hz, 1H), 4.20(t, J=6.4 Hz, 2H), 3.43(brs, 2H), 2.98(t, J=6.4 Hz, 2H), 2.75(t, J=8.0 Hz, 2H), 2.35(s, 3H), 2.32–2.18(m, 2H).

EXAMPLE 2(26)

2-(5-(2-(2-(4-methylphenyl)-5-methyloxazol-4-yl)ethoxy)-3,4-dihydronaphthalen-1-yl)acetic acid

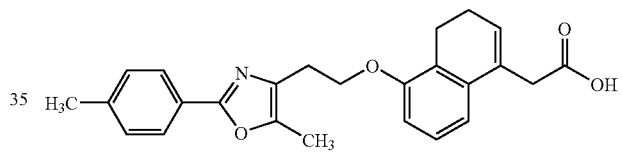

TLC: Rf 0.45 (chloroform:methanol=10:1); NMR (CDCl$_3$): δ 7.86(d, J=8.1 Hz, 2H), 7.22(d, J=8.1 Hz, 2H), 7.09(dd, J=7.8, 7.8 Hz, 1H), 6.83(d, J=7.8 Hz, 1H), 6.78(d, J=7.8 Hz, 1H), 6.00(t, J=4.5 Hz, 1H), 4.02(t, J=6.6 Hz, 2H), 3.44(s, 2H), 2.97(t, J=6.6 Hz, 2H), 2.75(t, J=6.6 Hz, 2H), 2.38(s, 3H), 2.34(s, 3H), 2.26(m, 2H).

EXAMPLE 2(27)

5-(5-(2-(2-phenyl-5-methyloxazol-4-yl)ethoxy)-3,4-dihydronaphthalen-1-yl)pentanoic acid

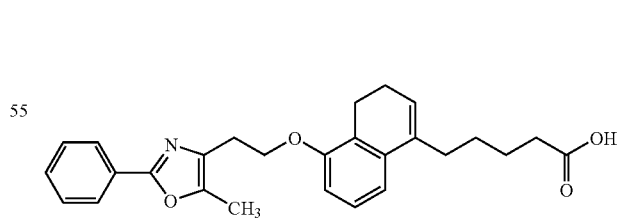

TLC: Rf 0.55 (chloroform:methanol=9:1); NMR(CDCl$_3$): δ 8.02–7.94(m, 2H), 7.48–7.37(m, 3H), 7.12(t, J=8.0 Hz, 1H), 6.87(t, J=8.0 Hz, 1H), 6.79(d, J=8.0 Hz, 1H), 5.84(t, J=4.6 Hz, 1H), 4.25(t, J=6.4 Hz, 2H), 3.00(t, J=6.4 Hz, 2H), 2.71(t, J=7.4 Hz, 2H), 2.50–2.30(m, 7H), 2.25–2.10(m, 2H), 1.78–1.45(m, 4H).

EXAMPLE 2(28)

5-(5-(2-(2-(4-methylphenyl)-5-methyloxazol-4-yl)ethoxy)-3,4-dihydronaphthalen-1-yl)pentanoic acid

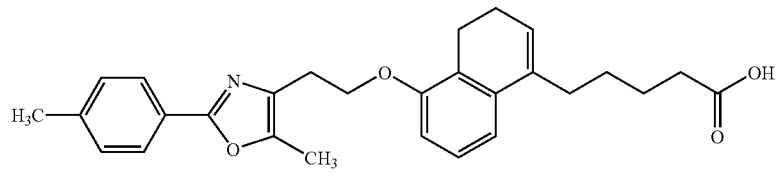

TLC: Rf 0.27 (chloroform:methanol=20:1); NMR (CDCl$_3$): δ 7.85(d, J=8 Hz, 2H), 7.20(d, J=8 Hz, 2H), 7.15(dd, J=8, 8 Hz, 1H), 6.85(d, J=8 Hz, 1H), 6.80(d, J=8 Hz, 1H), 5.85(t, J=7 Hz, 1H), 4.25(t, J=7 Hz, 2H), 3.00(t, J=7 Hz, 2H), 2.70(t, J=8 Hz, 2H), 2.50–2.30(m, 4H), 2.40(s, 3H), 2.30(s, 3H), 2.20(m, 2H), 1.80–1.50(m, 4H).

EXAMPLE 2(29)

5-(5-(2-(2-(1,3-dioxaindan-5-yl)-5-methyloxazol-4-yl)ethoxy)-3,4-dihydronaphthalen-1-yl)pentanoic acid

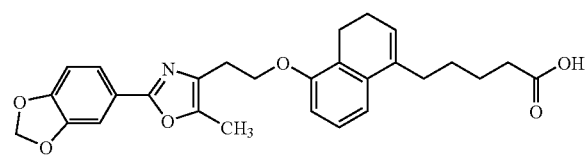

TLC: Rf 0.20 (chloroform:methanol=20:1); NMR (CDCl$_3$+CD$_3$OD): δ 7.55(dd, J=8 Hz, 1H), 7.45(d, J=1 Hz, 1H), 7.15(dd, J=7.5, 7.5 Hz, 1H), 6.90(d, J=7.5 Hz, 1H), 6.85(d, J=8 Hz, 1H), 6.80(d, J=7.5 Hz, 1H), 6.00(s, 2H), 5.85(t, J=4 Hz, 1H), 4.20(t, J=6.5 Hz, 2H), 2.95(t, J=6.5 Hz, 2H), 2.70(t, J=8 Hz, 2H), 2.50–2.20(m, 4H), 2.30(s, 3H), 2.20(m, 2H), 1.80–1.45(m, 4H).

EXAMPLE 2(30)

5-(5-(2-(2-(4-dimethylaminophenyl)-5-methyloxazol-4-yl)ethoxy)-3,4-dihydronaphthalen-1-yl)pentanoic acid

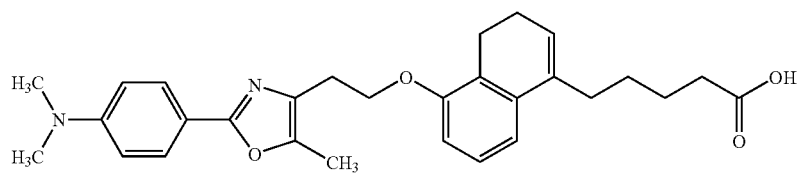

TLC: Rf 0.55 (chloroform:methanol=9:1); NMR(CDCl$_3$): δ 7.80(d, J=8 Hz, 2H), 7.10(m, 1H), 6.90–6.70(m, 4H), 5.85(m, 1H), 4.20(t, J=6.5 Hz, 2H), 3.00(s, 6H), 2.95(m, 2H), 2.70(m, 2H), 2.50–2.10(m, 6H), 1.80–1.50(m, 4H).

EXAMPLE 2(31)

2,2-dimethyl-3-(5-(2-(2-phenyl-5-methyloxazol-4-yl)ethoxy)-3,4-dihydronaphthalen-1-yl)propanoic acid

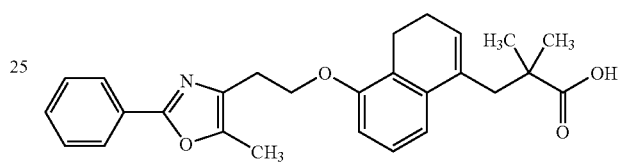

TLC: Rf 0.35 (hexane:ethyl acetate=2:1); NMR(DMSO-d$_6$): δ 12.07(br, 1H), 7.93–7.86(m, 2H), 7.53–7.42(m, 3H), 7.09(t, J=8.1 Hz, 1H), 6.95(d, J=8.1 Hz, 1H), 6.86(d, J=8.1 Hz, 1H), 5.84(t, J=4.2 Hz, 1H), 4.19(t, J=6.3 Hz, 2H), 2.93(t, J=6.3 Hz, 2H), 2.65(s, 2H), 2.55(t, J=7.8 Hz, 2H), 2.34(s, 3H), 2.08–1.98(m, 2H), 0.99(s, 6H).

EXAMPLE 2(32)

2,2-dimethyl-3-(5-(2-(2-(6-dimethylaminopyridin-3-yl)-5-methyloxazol-4-yl)ethoxy)-3,4-dihydronaphthalen-1-yl)propanoic acid

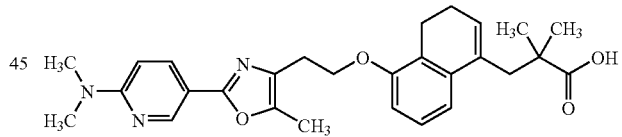

TLC: Rf 0.62 (hexane:ethyl acetate=1:19); NMR (CDCl$_3$): δ 8.73(d, J=2.7 Hz, 1H), 8.05(dd, J=8.7, 2.7 Hz, 1H), 7.08(dd, J=7.8, 7.8 Hz, 1H), 6.96(d, J=7.8 Hz, 1H), 6.76(d, J=7.8 Hz, 1H), 6.58(d, J=8.7 Hz, 1H), 5.91(t, J=4.5 Hz, 1H), 4.23(t, J=6.3 Hz, 2H), 3.20(s, 6H), 2.96(t, J=6.3 Hz, 2H), 2.76(s, 2H), 2.68(t, J=7.5 Hz, 2H), 2.34(s, 3H), 2.18–2.11(m, 2H), 1.15(s, 6H).

EXAMPLE 2(33)

2,2-dimethyl-3-(5-(2-(2-isopropyl-5-methyloxazol-4-yl)ethoxy)-3,4-dihydronaphthalen-1-yl)propanoic acid ½ calcium salt

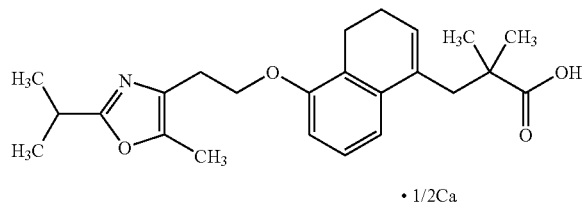

• 1/2Ca

TLC: Rf 0.86 (hexane:ethyl acetate=1:19); NMR(DMSO-d$_6$): δ 7.06(m, 1H), 7.58(d, J=7.5 Hz, 1H), 6.80(d, J=8.1 Hz, 1H), 5.88(m, 1H), 4.10(t, J=6.9 Hz, 2H), 2.94(quint, J=6.9 Hz, 1H), 2.79(t, J 6.6 Hz, 2H), 2.63(s, 2H), 2.50(m, 2H), 2.19(s, 3H), 2.05(m, 2H), 1.20(d, J=6.9 Hz, 6H), 0.89(s, 6H).

EXAMPLE 2(34)

2,2-dimethyl-3-(5-(2-(2-(6-(pyridin-1-yl)pyridin-3-yl)-5-methyloxazol-4-yl)ethoxy)-3,4-dihydronaphthalen-1-yl)propanoic acid sodium salt

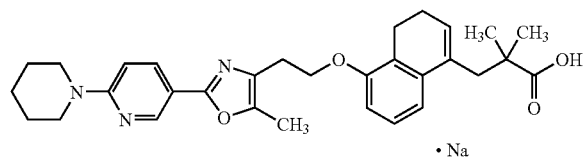

• Na

TLC: Rf 0.59 (chloroform:methanol=8:1); NMR(DMSO-d$_6$): δ 8.57(d, J=2.1 Hz, 1H), 7.90(dd, J=9.0, 2.1 Hz, 1H), 7.06(dd, J=8.1, 7.5 Hz, 1H), 6.97(d, J=7.5 Hz, 1H), 6.87(d, J=9.0 Hz, 1H), 6.81(d, J=8.1 Hz, 1H), 5.84(t, J=4.5 Hz, 1H), 4.15(t, J=6.3 Hz, 2H), 3.68–3.50(m, 4H), 2.88(t, J=6.3 Hz, 2H), 2.66–2.48(m, 4H), 2.29(s, 3H), 2.14–1.92(m, 2H), 1.70–1.38(m, 6H), 0.85(s, 6H).

EXAMPLE 2(35)

2,2-dimethyl-3-(5-(2-(2-(6-(morpholin-4-yl)pyridin-3-y)-5-methyloxazol-4-yl)ethoxy)-3,4-dihydronaphthalen-1-yl)propanoic acid sodium salt

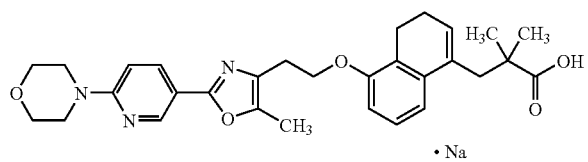

• Na

TLC: Rf 0.56 (chloroform:methanol=8:1); NMR(DMSO-d$_6$): δ 8.61(d, J=2.1 Hz, 1H), 7.97(dd, J=9.0, 2.1 Hz, 1H), 7.06(dd, J=8.1, 7.5 Hz, 1H), 6.97(d, J=8.1 Hz, 1H), 6.91(d, J=9.0 Hz, 1H), 6.81(d, J=7.5 Hz, 1H), 5.84(t, J=4.5 Hz, 1H), 4.16(t, J=6.0 Hz, 2H), 3.76–3.62(m, 4H), 3.60–3.44(m, 4H), 2.89(t, J=6.0 Hz, 2H), 2.64–2.48(m, 4H), 2.31(s, 3H), 2.14–1.92(m, 4H), 0.84(s, 6H).

EXAMPLE 2(36)

2,2-dimethyl-3-(5-(2-(2-(6-methylpyridin-3-yl)-5-methyloxazol-4-yl)ethoxy)-3,4-dihydronaphthalen-1-yl)propanoic acid

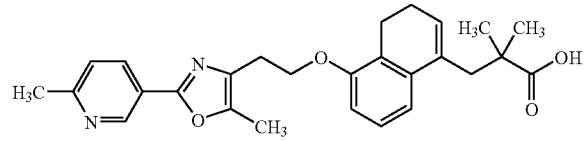

TLC: Rf 0.48 (hexane:ethyl acetate=1:19); NMR (CDCl$_3$): δ 9.05(d, J=1.8 Hz, 1H), 8.13(dd, J=8.4, 1.8 Hz, 1H), 7.22(d, J=8.1 Hz, 1H), 7.07(dd, J=8.1, 8.1, Hz, 1H), 6.96(d, J=8.1 Hz, 1H), 6.75(d, J=8.4 Hz, 1H), 5.91(m, 1H), 4.24(t, J=6.6 Hz, 2H), 2.98(t, J=6.6 Hz, 2H), 2.76(s, 2H), 2.68(t, J=7.8 Hz, 2H), 2.60(s, 3H), 2.38(s, 3H), 2.18–2.11(m, 2H), 1.15(s, 6H).

EXAMPLE 2(37)

2,2-dimethyl-3-(5-(2-(2-(morpholin-4-yl)-5-methylthiazol-4-yl)ethoxy)-3,4-dihydronaphthalen-1-yl)propanoic acid

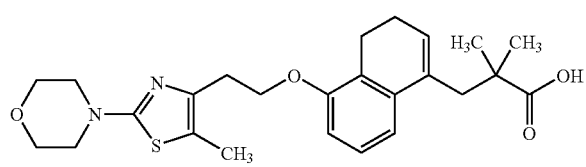

TLC: Rf 0.72 (hexane:ethyl acetate=1:19); NMR (CDCl$_3$): δ 7.08(dd, J=8.1, 7.5 Hz, 1H), 6.95(d, J=7.5 Hz, 1H), 6.76(d, J=8.1 Hz, 1H), 5.90(t, J=4.8 Hz, 1H), 4.21(t, J=6.6 Hz, 2H), 3.79(t, J=4.8 Hz, 4H), 3.39(m, 4H), 2.98(t, J=6.6 Hz, 2H), 2.76(s, 2H), 2.67(t, J=7.8 Hz, 2H), 2.27(s, 3H), 2.18–2.11(m, 2H), 1.14(s, 6H).

EXAMPLE 2(38)

2,2-dimethyl-3-(5-(2-(2-(piperidin-1-yl)-5-methylthiazol-4-yl)ethoxy)-3,4-dihydronaphthalen-1-yl)propanoic acid

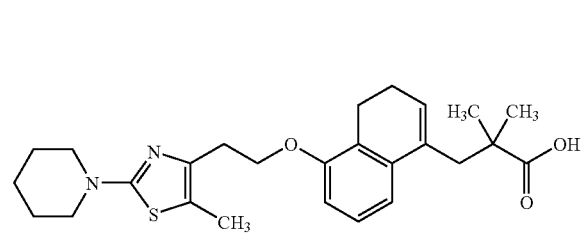

TLC: Rf 0.76 (chloroform:methanol=19:1); NMR (CDCl$_3$): δ 7.07(dd, J=7.8, 7.8 Hz, 1H), 6.94(d, J=7.8 Hz, 1H), 6.76(d, J=7.8 Hz, 1H), 5.90(t, J=4.8 Hz, 1H), 4.20(t, J=6.9 Hz, 2H), 3.36(m, 4H), 2.95(t, J=6.9 Hz, 2H), 2.76(s, 2H), 6.69(t, J=8.4 Hz, 2H), 2.24(s, 3H), 2.18–2.11(m, 2H), 1.62(m, 6H), 1.14(s, 6H).

EXAMPLE 2(39)

2,2-dimethyl-3-(5-(2-(2-(thiomorpholin-4-yl)-5-methylthiazol-4-yl)ethoxy)-3,4-dihydronaphthalen-1-yl)propanoic acid

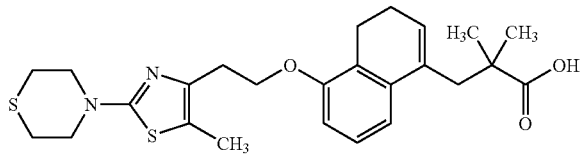

TLC: Rf 0.73 (chloroform:methanol=19:1); NMR (CDCl$_3$): δ 7.08(dd, J=8.7, 8.7 Hz, 1H), 6.95(d, J=8.7 Hz, 1H), 6.76(d, J=8.7 Hz, 1H), 5.91(m, 1H), 4.20(t, J=6.6 Hz, 2H), 3.75(m, 4H), 2.94(t, J=6.6 Hz, 2H), 2.77(s, 2H), 2.68(m, 6H), 2.25(s, 3H), 2.15(m, 2H), 1.15(s, 6H).

EXAMPLE 2(40)

2,2-dimethyl-5-(5-(2-(2-phenyl-5-methyloxazol-4-yl)ethoxy)-3,4-dihydronaphthalen-1-yl)pentanoic acid

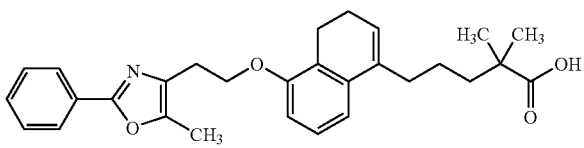

TLC: Rf 0.49 (chloroform:methanol=10:1); NMR (CDCl$_3$): δ 8.01–7.92(m, 2H), 7.48–7.36(m, 3H), 7.10(t, J=8.0 Hz, 1H), 6.86(d, J=8.0 Hz, 1H), 6.77(d, J=8.0 Hz, 1H), 5.83(t, J=4.6 Hz, 1H), 4.24(t, J=6.6 Hz, 2H), 2.99(t, J=6.6 Hz, 2H), 2.7 0(t, J=7.8 Hz, 2H), 2.46–2.32(m, 2H), 2.36(s, 3H), 2.24–2.11(m, 2H), 1.67–1.40(m, 4H),1.17(s, 6H).

EXAMPLE 2(41)

2-benzyloxy-3-(5-(2-(2-(4-methylphenyl)-5-methyloxazol-4-yl)ethoxy)-3,4-dihydronaphthalen-1-yl)propanoic acid

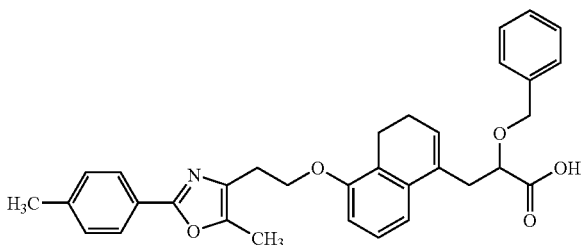

TLC: Rf 0.38 (chloroform:methanol=10:1); NMR (CDCl$_3$): δ 7.86(m, 2H), 7.34–7.12(m, 7H), 7.08(dd, J=8.1, 8.1 Hz, 1H), 6.89(d, J=8.1 Hz, 1H), 6.80(d, J=8.1 Hz, 1H), 5.99(dd, J=4.5, 4.5 Hz, 1H), 4.57(d, J=11.7 Hz, 1H), 4.41(d, J=11.7 Hz , 1H), 4.29–4.20(m, 2H), 4.16(dd, J=9.0, 3.6 Hz, 1H), 3.10(m, 1H), 3.00(t, J=6.6 Hz, 2H), 2.90–2.66(m, 2H), 2.60(m, 1H), 2.38(s, 3H), 2.36(s, 3H), 2.25–2.12(m, 2H).

EXAMPLE 3

2-(5-(2-(2-(4-cyclohexylphenyl)-5-methyloxazol-4-yl)ethoxy)-3,4-dihydronaphthalen-1-yl)ethanol

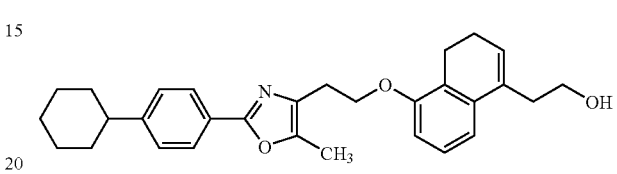

To a tetrahydrofuran (7.0 ml) suspension of lithium aluminum hydride (147 mg), a tetrahydrofuran (12 ml) solution of the compound (1.93 g) prepared in Example 1(29) was added dropwise at 0° C., followed by stirring at room temperature for 1.5 hours. The reaction mixture was cooled to 0° C., and a saturated aqueous sodium sulfate solution was added thereto. The reaction mixture was dried with anhydrous magnesium sulfate, and concentrated. The residue was recrystallized with a mixed solvent of hexane and ethyl acetate to thereby obtain the compound of the present invention (1.26 g) having the following physical data.

TLC: Rf 0.50 (hexane:ethyl acetate=1:1); NMR(CDCl$_3$): δ 7.92–7.84(m, 2H), 7.30–7.22(m, 2H), 7.13(dd, J=8.1, 8.1 Hz, 1H), 7.89(d, J=8.1 Hz, 1H), 6.81(d, J=8.1 Hz, 1H), 5.95(t, J=4.5 Hz, 1H), 4.25(t, J=6.6 Hz, 2H), 3.82–3.68(m, 2H), 2.98(t, J=6.6 Hz, 2H), 2.78–2.66(m, 4H), 2.53(m, 1H), 2.36(s, 3H), 2.30–2.16(m, 2H), 1.96–1.70(m, 5H), 1.54–1.14(m, 5H).

EXAMPLE 3(1) TO EXAMPLE 3(5)

The following compounds of the present invention were obtained in the same manner as in Example 3 using the compound prepared in Example 1(27), Example 1(28), Example 1(30), Example 1(31) and Example 2 instead of the compound prepared in Example 1(29).

EXAMPLE 3(1)

2-(5-(2-(2-(4-methylphenyl)-5-methyloxazol-4-yl)ethoxy)-3,4-dihydronaphthalen-1-yl)ethanol

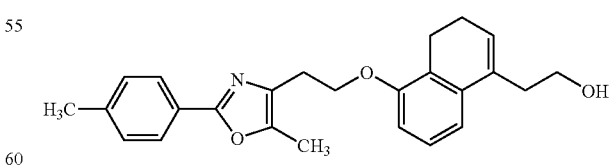

TLC: Rf 0.27 (hexane:ethyl acetate=2:1); NMR(CDCl$_3$): δ 7.86(d, J=8.4 Hz, 2H), 7.23(d, J=8.4 Hz, 2H), 7.12(dd, J=8.1, 8.1 Hz, 1H), 6.89(d, J=8.1 Hz, 1H), 6.81(d, J=8.1 Hz, 1H), 5.94(t, J=4.5 Hz, 1H), 4.25(t, J=6.6 Hz, 2H), 3.76(m, 2H), 2.98(t, J=6.6 Hz, 2H), 2.78–2.67(m, 4H), 2.38(s, 3H), 2.36(s, 3H), 2.22(m, 2H).

EXAMPLE 3(2)

2-(5-(2-(2-isopropyl-5-methyloxazol-4-yl)ethoxy)-3,4-dihydronaphthalen-1-yl)ethanol

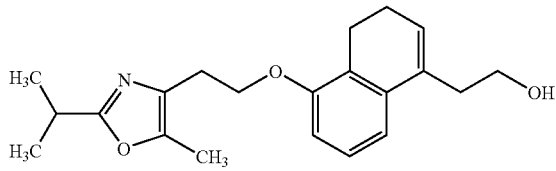

TLC: Rf 0.34 (hexane:ethyl acetate=1:1); NMR(CDCl$_3$): δ 7.12(dd, J=7.8, 7.8 Hz, 1H), 6.89(d, J=7.8 Hz, 1H), 6.79(dd, J=7.8, 0.9 Hz, 1H), 5.95(dd, J=4.5, 4.5 Hz, 1H), 4.17(t, J=6.6 Hz, 2H), 3.82–3.70(m, 2H), 2.99(sept., J=6.9 Hz, 1H), 2.89(t, J=6.6 Hz, 2H), 2.76–2.66(m, 4H), 2.28–2.16(m, 2H), 2.25(s, 3H), 1.31(d, J=6.9 Hz, 6H).

EXAMPLE 3(3)

2-(5-(2-(2-(4-methylpiperazin-1-yl)-5-methylthiazol-4-yl)ethoxy)-3,4-dihydronaphthalen-1-yl)ethanol

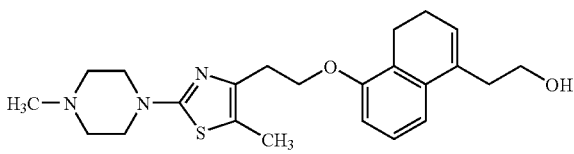

TLC: Rf 0.26(methanol:ethyl acetate=1:5); NMR (CDCl$_3$): δ 7.12(dd, J=8.1, 8.1 Hz, 1H), 6.88(d, J=8.1 Hz, 1H), 6.80(d, J=8.1 Hz, 1H), 5.95(brt, 1H), 4.22(t, J=6.6 Hz, 2H), 3.76(t, J=6.6 Hz, 2H), 3.40(brt, 4H), 2.96(t, J=6.6 Hz, 2H), 2.76–2.67(m, 4H), 2.50(brt, 4H), 2.33(s, 3H), 2.26(s, 3H), 2.26–2.17(m, 2H).

EXAMPLE 3(4)

2-(5-(2-(2-(piperidin-1-yl)-5-methylthiazol-4-yl)ethoxy)-3,4-dihydronaphthalen-1-yl)ethanol

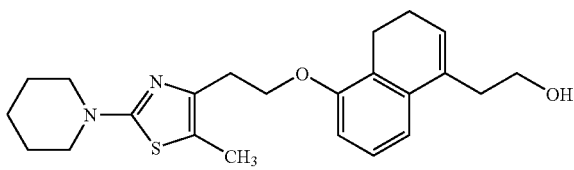

TLC: Rf 0.27 (hexane:ethyl acetate=2:1); NMR(CDCl$_3$): δ 7.12(dd, J=7.8, 7.8 Hz, 1H), 6.88(d, J=7.8 Hz, 1H), 6.81(d, J=7.8 Hz, 1H), 5.95(dd, J=4.5, 4.5 Hz, 1H), 4.21(t, J=6.9 Hz, 2H), 3.75(m, 2H), 3.36(m, 4H), 2.96(t, J=6.9 Hz, 2H), 2.77–2.68(m, 4H), 2.25(s, 3H), 2.27–2.18(m, 2H), 1.72–1.53(m, 6H).

EXAMPLE 3(5)

3-(5-(2-(2-(4-methylphenyl)-5-methyloxazol-4-yl)ethoxy)-3,4-dihydronaphthalen-1-yl)propanol

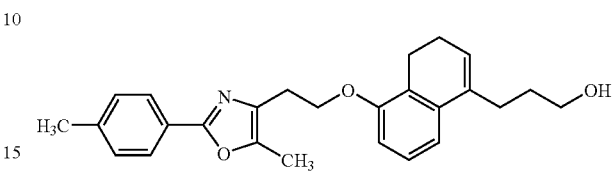

TLC: Rf 0.55 (ethyl acetate:hexane=2:1); NMR(CDCl$_3$): δ 7.86(d, J=8.1 Hz, 2H), 7.23(d, J=8.1 Hz, 2H), 7.12(t, J=7.8 Hz, 1H), 6.91 (d, J=7.8 Hz, 1H), 6.80(d, J=7.8 Hz, 1H), 5.90–5.84(m, 1H), 4.25(t, J=6.6 Hz, 2H), 3.68(t, J=6.6 Hz, 2H), 2.99(t, J=6.6 Hz, 2H), 2.71(t, J=7.8 Hz, 2H), 2.52(t, J=7.8 Hz, 2H), 2.39(s, 3H), 2.36(s, 3H), 2.24–2.14(m, 2H), 1.78(quint, J=7.8 Hz, 2H), 1.58(s, 1H).

EXAMPLE 4

2-(5-(2-(2-(4-cyclohexylphenyl)-5-methyloxazol-4-yl)ethoxy)-3,4-dihydronaphthalen-1-yl)acetaldehyde

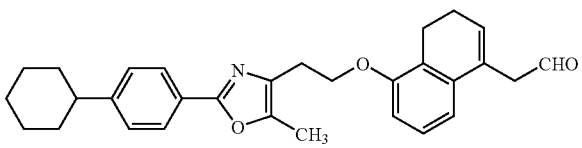

To a mixed solution of the compound (1.20 g) prepared in Example 3 in ethyl acetate (12 ml) and dimethylsulfoxide (5.0 ml), diisopropylethylamine (2.7 ml) was added, and a dimethylsulfoxide (6.5 ml) solution of sulfur trioxide-pyridine complex (1.25 g) was added dropwise thereto at −10° C., followed by stirring at −10° C. for 2 hours. The reaction mixture was poured into cold water, and extracted with ethyl acetate. The extract was washed with a saturated saline, dried with anhydrous magnesium sulfate, and concentrated to thereby obtain the crude title compound (1.57 g) having the following physical data. The obtained compound was used without purification in the subsequent reaction.

TLC: Rf 0.60 (hexane:ethyl acetate=2:1).

EXAMPLE 4(1) TO EXAMPLE 4(4)

The following compounds of the present invention were obtained in the same manner as in Example 4 using the compound prepared in Example 3(1) to Example 3(4) instead of the compound prepared in Example 3.

EXAMPLE 4(1)

2-(5-(2-(2-(4-methylphenyl)-5-methyloxazol-4-yl)ethoxy)-3,4-dihydronaphthalen-1-yl)acetaldehyde

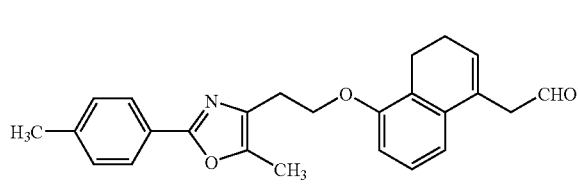

TLC: Rf 0.58 (hexane:ethyl acetate=2:1); NMR(CDCl$_3$): δ 9.63(t, J=1.5 Hz, 1H), 7.86(d, J=8.1 Hz, 2H), 7.24(d, J=8.1 Hz, 2H), 7.12(dd, J=7.8, 7.8 Hz, 1H), 6.83(d, J=7.8 Hz, 1H), 6.73(d, J=7.8 Hz, 1H), 6.02(t, J=4.5 Hz, 1H), 4.25(t, J=6.6 Hz, 2H), 3.43(m, 2H), 2.98(t, J=6.6 Hz, 2H), 2.78(t, J=8.4 Hz, 2H), 2.38(s, 3H), 2.36(s, 3H), 2.31(m, 2H).

EXAMPLE 4(2)

2-(5-(2-(2-isopropyl-5-methyloxazol-4-yl)ethoxy)-3,4-dihydronaphthalen-1-yl)acetaldehyde

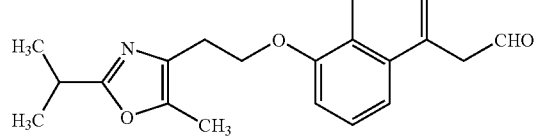

TLC: Rf 0.62 (hexane:ethyl acetate=1:1); NMR(CDCl$_3$): δ 9.64(t, J=2.4 Hz, 1H), 7.12(dd, J=7.8, 7.8 Hz, 1H), 6.81(d, J=7.8 Hz, 1H), 6.73(d, J=7.8 Hz, 1H), 6.03(dd, J=4.5, 4.5 Hz, 1H), 4.18(t, J=6.6 Hz, 2H), 3.48–3.40(m, 2H), 2.99 (sept., J=6.9 Hz, 1H), 2.89(t, J=6.6 Hz, 2H), 2.77(t, J=8.1 Hz, 2H), 2.36–2.16(m, 2H), 2.25(s, 3H), 1.31(d, J=6.9 Hz, 6H).

EXAMPLE 4(3)

2-(5-(2-(2-(4-methylpiperazin-1-yl)-5-methylthiazol-4-yl)ethoxy)-3,4-dihydronaphthalen-1-yl)acetaldehyde

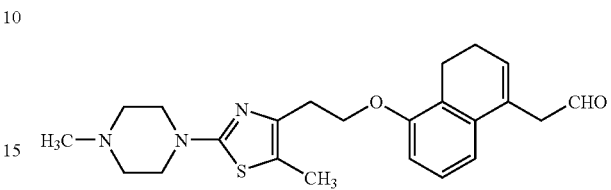

TLC: Rf 0.25(methanol:ethyl acetate=1:5); NMR (CDCl$_3$): δ 9.64(t, J=2.4 Hz, 1H), 7.12(dd, J=8.1, 8.1 Hz, 1H), 6.82(d, J=8.1 Hz, 1H), 6.73(d, J=8.1 Hz, 1H), 6.03(brt, 1H), 4.22(t, J=6.9 Hz, 2H), 3.46–3.37(m, 6H), 2.96(t, J=6.9 Hz, 2H), 2.78(dd, J=8.4, 8.4 Hz, 2H), 2.51(m, 4H), 2.34(s, 3H), 2.26(s, 3H), 2.34–2.23(m, 2H).

EXAMPLE 4(4)

2-(5-(2-(2-(piperidin-1-yl)-5-methylthiazol-4-yl)ethoxy)-3,4-dihydronaphthalen-1-yl)acetaldehyde

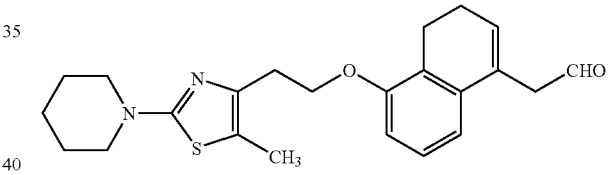

TLC: Rf 0.57 (hexane:ethyl acetate=2:1); NMR(CDCl$_3$): δ 9.64(t, J=2.7 Hz, 1H), 7.12(dd, J=8.1, 8.1 Hz, 1H), 6.82(d, J=8.1 Hz, 1H), 6.72(d, J=8.1 Hz, 1H), 6.02(dd, J=4.5, 4.5 Hz, 1H), 4.22(t, J=6.9 Hz, 2H), 3.44(m, 2H), 3.36(m, 4H), 2.96(t, J=6.9 Hz, 2H), 2.78(dd, J=8.1, 8.1 Hz, 2H), 2.36–2.26(m, 2H), 2.25(s, 3H), 1.72–1.54(m, 6H).

REFERENCE EXAMPLE 28

2-(4-cyclohexylphenyl)-4-(2-((5-(2,2-diethoxyethyl)-7,8-dihydronaphthalen-1-yl)oxy)ethyl)-5-methyloxazole

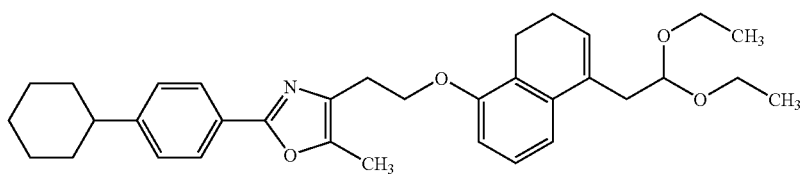

To an ethanol (7.8 ml) solution of the compound prepared in Example 4, p-toluenesulfonic acid hydrate (300 mg) was added, followed by stirring at 90° C. for 3 hours. The reaction mixture was cooled to room temperature, and poured into a cold saturated aqueous sodium hydrogen carbonate solution, followed by extracting with ethyl acetate. The extract was washed with saturated saline, dried with anhydrous magnesium sulfate, and concentrated. The residue was purified by silica gel column chromatography (hexane:ethyl acetate=15:1 to 9:1) to thereby obtain the title compound (1.04 g) having the following physical data.

TLC: Rf 0.38 (hexane:ethyl acetate=5:1); NMR(CDCl$_3$): δ 7.94–7.84(m, 2H), 7.30–7.22(m, 2H), 7.12(dd, J=7.8, 7.8 Hz, 1H), 6.93(d, J=7.8 Hz, 1H), 6.79(d, J=7.8 Hz, 1H), 5.97(t, J=4.5 Hz, 1H), 4.64(m, 1H), 4.25(t, J=6.6 Hz, 2H), 3.74–3.58(m, 2H), 3.52–3.38(m, 2H), 2.98(t, J=6.6 Hz, 2H), 2.80–2.64(m, 4H), 2.53(m, 1H), 2.35(s, 3H), 2.26–2.14(m, 2H), 1.96–1.70(m, 5H), 1.52–1.20(m, 5H), 1.16(t, J=6.9 Hz, 6H).

REFERENCE EXAMPLE 29

3-(5-(2-(2-(4-cyclohexylphenyl)-5-methyloxazol-4-yl)ethoxy)3,4-dihydronaphthalen-1-yl)-2-ethoxypropanenitrile

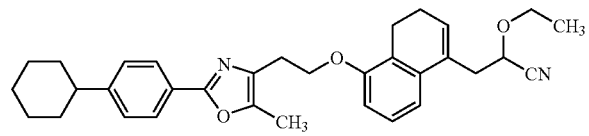

To a methylene chloride (9.5 ml) solution of the compound (1.00 g) prepared in Reference Example 28, trimethylsilyl cyanide (0.76 ml) and boron trifluoride ethyl ether complex (0.14 ml) was added, followed by stirring at room temperature for 1.5 hours. The reaction mixture was poured into a cold aqueous sodium hydrogen carbonate solution, and extracted with ethyl acetate. The extract was washed with saturated saline, dried with anhydrous magnesium sulfate, and concentrated. The residue was purified by silica gel column chromatography (hexane:ethyl acetate=10:1 to 7:1) to thereby obtain the crude title compound (837 mg) having the following physical data. The obtained compound was used without purification in the subsequent reaction.

TLC: Rf 0.27 (hexane:ethyl acetate=5:1); NMR(CDCl$_3$): δ 7.94–7.84(m, 2H), 7.32–7.22(m, 2H), 7.14(dd, J=8.4, 8.4 Hz, 1H), 6.88–6.76(m, 2H), 6.09(t, J=4.5 Hz, 1H), 4.32–4.18(m, 3H), 3.80(m, 1H), 3.48(m, 1H), 3.10–2.44(m, 7H), 2.36(s, 3H), 2.32–2.10(m, 2H), 1.96–1.70(m, 5H), 1.52–1.14(m, 8H).

EXAMPLE 5

2-ethoxy-3-(5-(2-(2-(4-cyclohexylphenyl)-5-methyloxazol-4-yl)ethoxy)-3,4-dihydronaphthalen-1-yl)propanoic acid

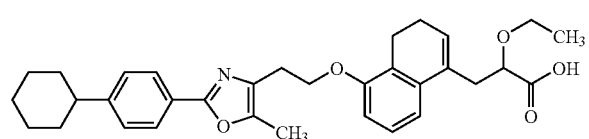

To an ethanol (11 ml) solution of the compound prepared in Reference Example 29, a 5N aqueous sodium hydroxide solution (3.8 ml) was added, followed by stirring at 90° C. for 4 hours. The reaction mixture was cooled to room temperature, poured into cold water, and washed with t-butyl methyl ether. The aqueous layer was neutralized with 2N hydrochloric acid, and extracted with ethyl acetate. The extract was washed with saturated saline, dried with anhydrous magnesium sulfate, and concentrated. The residue was purified by silica gel column chromatography (chloroform:methanol=12:1) to thereby obtain the compound of the present invention (676 mg) having the following physical data.

TLC: Rf 0.42 (chloroform:methanol=8:1); NMR(CDCl$_3$): δ 7.94–7.84(m, 2H), 7.32–7.22(m, 2H), 7.13(dd, J=7.8, 7.8 Hz, 1H), 6.96(d, J=7.8 Hz, 1H), 6.80(d, J=7.8 Hz, 1H), 5.98(t, J=4.5 Hz, 1H), 4.24(t, J=6.6 Hz, 2H), 4.04(dd, J=8.7, 4.2 Hz, 1H), 3.54(m, 1H), 3.43(m, 1H), 3.06(m, 1H), 2.99(t, J=6.6 Hz, 2H), 2.90–2.44(m, 4H), 2.35(s, 3H), 2.26–2.12(m, 2H), 1.96–1.68(m, 5H), 1.52–1.16(m, 5H), 1.12(t, J=6.9 Hz, 3H).

EXAMPLE 6(1) TO EXAMPLE 6(4)

The following compounds of the present invention were obtained in the same manner as in Reference Example 28→Reference Example 29→Example 5 using the compound prepared in Example 4(1) to Example 4(4) instead of the compound prepared in Example 4.

EXAMPLE 6(1)

2-ethoxy-3-(5-(2-(2-(4-methylphenyl)-5-methyloxazol-4-yl)ethoxy)-3,4-dihydronaphthalen-1-yl)propanoic acid

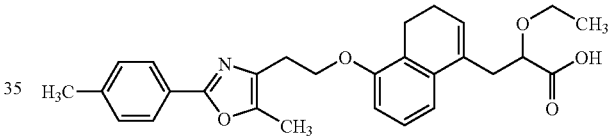

TLC: Rf 0.42 (chloroform:methanol=10:1); NMR (CDCl$_3$): δ 7.86(d, J=8.1 Hz, 2H), 7.23(d, J=8.1 Hz, 2H), 7.14(dd, J=7.8, 7.8 Hz, 1H), 6.96(d, J=7.8 Hz, 1H), 6.82(d, J=7.8 Hz, 1H), 5.98(t, J=4.5 Hz, 1H), 4.26 & 4.25(each t, J=6.6 Hz, total 2H), 4.04(dd, J=9.0, 3.9 Hz, 1H), 3.49(m, 2H), 3.08(m, 1H), 2.99(t, J=6.6 Hz, 2H), 2.86 & 2.81(each t, J=6.6 Hz, total 1H), 2.72–2.52(m, 2H), 2.38(s, 3H), 2.36(s, 3H), 2.21(m, 2H), 1.12(t, J=6.9 Hz, 3H).

EXAMPLE 6(2)

2-ethoxy-3-(5-(2-(2-isopropyl-5-methyloxazol-4-yl)ethoxy)-3,4-dihydronaphthalen-1-yl)propanoic acid ½ calcium salt

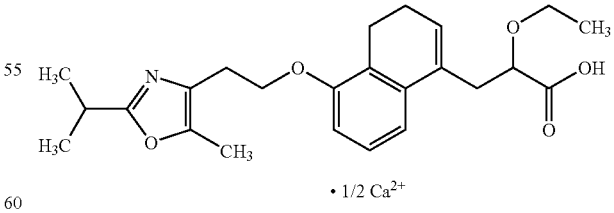

• 1/2 Ca$^{2+}$

TLC: Rf 0.42 (chloroform:methanol=8:1); NMR(DMSO-d$_6$): δ 7.07(dd, J=7.8, 7.8 Hz, 1H), 6.98(d, J=7.8 Hz, 1H), 6.81(d, J=7.8 Hz, 1H), 5.85(dd, J=4.2, 4.2 Hz, 1H), 4.09(t, J=6.3 Hz, 2H), 3.74–3.46(m, 2H), 3.13(m, 1H), 3.02–2.56 (m, 5H), 2. 54–2.30(m, 2H), 2.18(s, 3H), 2.16–1.94(m, 2H), 1.20(d, J=6.6 Hz, 6H), 0.92(t, J=6.9 Hz, 3H).

EXAMPLE 6(3)

2-ethoxy-3-(5-(2-(2-(4-methylpiperazin-1-yl)-5-methylthiazol-4-yl)ethoxy)-3,4-dihydronaphthalen-1-yl)propanoic acid

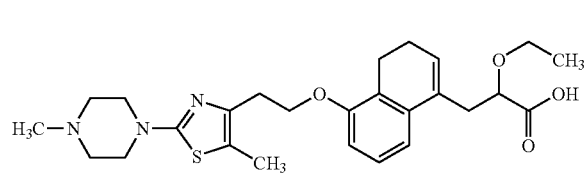

TLC: Rf 0.35 (chloroform:methanol=5:1); NMR(CDCl₃+CD₃OD): δ 7.11(dd, J=8.1, 8.1 Hz, 1H), 6.99(d, J=8.1 Hz, 1H), 6.77(d, J=8.1 Hz, 1H), 5.98(dd, J=4.2, 4.2 Hz, 1H), 4.22(m, 2H), 3.98(dd, J=9.0, 4.5 Hz, 1H), 3.66–3.46(m, 5H), 3.44–3.32(m, 1H), 3.02–2.45(m, 10H), 2.52(s, 3H), 2.27(s, 3H), 2.22–2.10(m, 2H), 1.10(t, J=6.9 Hz, 3H).

EXAMPLE 6(4)

2-ethoxy-3-(5-(2-(2-(piperidin-1-yl)-5-methylthiazol-4-yl)ethoxy)-3,4-dihydronaphthalen-1-yl)propanoic acid

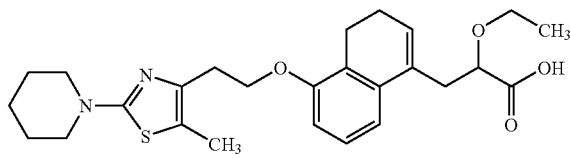

TLC: Rf 0.45 (chloroform:methanol=10:1); NMR (CDCl₃): δ 7.12(dd, J=8.1, 8.1 Hz, 1H), 6.94(d, J=8.1 Hz, 1H), 6.79(d, J=8.1 Hz, 1H), 5.98(dd, J=4.5, 4.5 Hz, 1H), 4.20(m, 2H), 4.03(dd, J=9.0, 3.9 Hz, 1H), 3.55(m, 1H), 3.41(m, 1H), 3.37(m, 4H), 3.06(m, 1H), 2.97(t, J=6.9 Hz, 2H), 2.82(ddd, J=15.9, 7.5, 7.5 Hz, 1H), 2.74–2.51(m, 2H), 2.24(s, 3H), 2.25–2.14(m, 2H), 1.72–1.55(m, 6H), 1.12(t, J=6.9 Hz, 3H).

EXAMPLE 7

2-ethoxy-3-(5-(2-(2-(4-methylphenyl)-5-methyloxazol-4-yl)ethoxy)-3,4-dihydronaphthalen-1-yl)propanamide

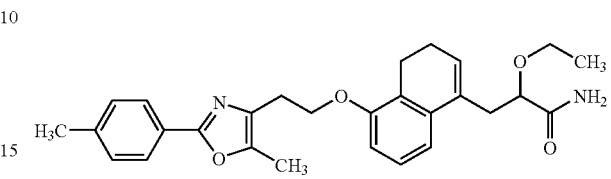

To a mixed solution of 3-(5-(2-(2-(4-methylphenyl)-5-methyloxazol-4-yl)ethoxy)-3,4-dihydronaphthalen-1-yl)-2-ethoxypropanenitrile (146 mg; this compound was prepared in the same manner as in Reference Example 28→Reference Example 29 using the compound prepared in Example 4(1) instead of the compound prepared in Example 4.) in ethanol (4 ml) and tetrahydrofuran (4 ml), a 5N aqueous sodium hydroxide solution (0.66 ml) was added, followed by refluxing for 5 hours. The reaction mixture was cooled to room temperature, and concentrated. The residue was diluted with water. The diluted solution was acidified with 1 N hydrochloric acid, and extracted with diethyl ether. The extract was washed with saturated saline, dried with anhydrous magnesium sulfate, and concentrated. The residue was purified by silica gel column chromatography (chloroform:methanol=50:1 to 30:1). The obtained solid was recrystallized with a mixed solvent of ethyl acetate and hexane to thereby obtain the compound of the present invention (75 mg) having the following physical data.

TLC: Rf 0.63 (chloroform:methanol=10:1); NMR (CDCl₃): δ 7.86(d, J=8.4 Hz, 2H), 7.23(d, J=8.4 Hz, 2H), 7.14(dd, J=7.8, 7.8 Hz, 1H), 7.04(d, J=7.8 Hz, 1H), 6.81(d, J=7.8 Hz, 1H), 6.55(br s, 1H), 5.97(t, J=4.5 Hz, 1H), 5.37(br s, 1H), 4.26 & 4.25(each t, J=6.6 Hz, total 2H), 3.88(dd, J=9.6, 3.0 Hz, 1H), 3.41(m, 2H), 2.98(t, J=6.6 Hz, 2H), 2.89 & 2.84(each t, J=6.6 Hz, total 1H), 2.62–2.48(m, 2H), 2.38(s, 3H), 2.36(s, 3H), 2.22(m, 2H), 1.07(t, J=6.9 Hz, 3H).

REFERENCE EXAMPLE 30

N-(1-methyl-1-methoxyethoxy)-3-(5-(2-(2-(4-methylphenyl)-5-methyloxazol-4-yl)ethoxy)-3,4-dihydronaphthalen-1-yl)propanamide

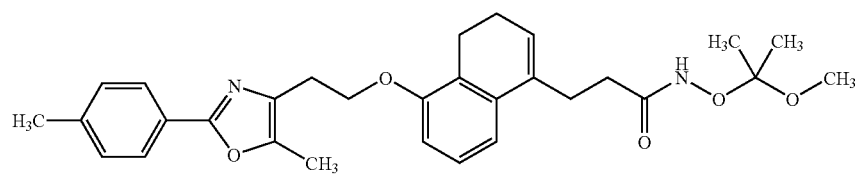

To a dimethylformamide (5 ml) solution of the compound (208 mg) prepared in Example 2 and 2-aminooxy-2-methoxypropane (57.7 mg), 1-ethyl-3-(3-dimethylaminopropyl)carbodiimide hydrochloride (115 mg), 1-hydroxybenzotriazole (81 mg) and triethylamine (83 μl) were added, followed by stirring at room temperature overnight. The reaction mixture was concentrated. The residue was diluted with methylene chloride. The diluted solution was washed with 1N hydrochloric acid, a saturated aqueous sodium hydrogen carbonate solution and saturated saline in this order, dried with anhydrous sodium sulfate, and concentrated. The residue was purified by silica gel column chromatography (chloroform:methanol=50:1) to thereby obtain the title compound (239 mg) having the following physical data.

TLC: Rf 0.44 (chloroform:methanol=10:1); NMR (CDCl$_3$): δ 7.86(d, J=7.8 Hz, 2H), 7.55(s, 1H), 7.23(d, J=7.8 Hz, 2H), 7.13(dd, J=8.4, 8.4 Hz, 1H), 6.88(m, 2H), 6.81(d, J=8.4 Hz, 1H), 5.92(m, 1H), 4.24(t, J=6.6 Hz, 2H), 3.24(s, 3H), 2.98(t, J=6.6 Hz, 2H), 2.95(s, 3H), 2.88(s, 3H), 2.80(m, 2H), 2.70(t, J=8.1 Hz, 2H), 2.38(s, 3H), 2.36(s, 3H), 2.17(m, 2H).

EXAMPLE 8

N-hydroxy-3-(5-(2-(2-(4-methylphenyl)-5-methyloxazol-4-yl)ethoxy)-3,4-dihydronaphthalen-1-yl)propanamide

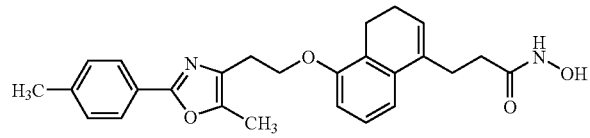

To a methanol (2 ml) solution of the compound (239 mg) prepared in Reference Example 30, 4N hydrogen chloride-dioxane solution (1.1 ml) was added, followed by stirring at room temperature for 1 hour. The reaction mixture was concentrated, and solidified by diethyl ether. The solid was crystallized with methanol to thereby obtain the compound of the present invention (40 mg) having the following physical data.

TLC: Rf 0.48 (chloroform:methanol=10:1); NMR (DMSO-d$_6$): δ 10.35(s, 1H), 7.79(d, J=8.4 Hz, 2H), 7.29(d, J=8.4 Hz, 2H), 7.13(dd, J=8.1, 8.1 Hz, 1H), 6.88(m, 2H), 5.82(m, 1H), 4.19(t, J=6.3 Hz, 2H), 2.91(t, J=6.3 Hz, 2H), 2.67–2.53(m, 4H), 2.34(s, 3H), 2.33(s, 3H), 2.15–2.03(m, 4H).

EXAMPLE 9

N-hydroxy-2-(5-(2-(2-(4-methylphenyl)-5-methyloxazol-4-yl)ethoxy)-3,4-dihydronaphthalen-1-yl)acetamide

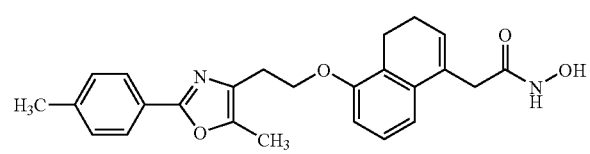

The compound of the present invention having the following physical data was obtained in the same manner as in Reference Example 30→Example 8 using the compound prepared in Example 2(26) instead of the compound prepared in Example 2.

TLC: Rf 0.36 (chloroform:methanol=10:1); NMR (DMSO-d$_6$): δ 10.47(s, 1H), 8.73(s, 1H), 7.79(d, J=8.1 Hz, 2H), 7.29(d, J=8.1 Hz, 2H), 7.09(dd, J=7.8, 7.8 Hz, 1H), 6.89(d, J=7.8 Hz, 1H), 6.88(d, J=7.8 Hz, 1H), 5.91(t, J=4.5 Hz, 1H), 4.18(t, J=6.3 Hz, 2H), 3.07(s, 2H), 2.91(t, J=6.3 Hz, 2H), 2.59(t, J=8.4 Hz, 2H), 2.34(s, 3H), 2.33(s, 3H), 2.13(m, 2H).

EXAMPLE 10

3-(5-(2-(2-(4-methylphenyl)-5-methyloxazol-4-yl)ethoxy)-3,4-dihydronaphthalen-1-yl)propanamide

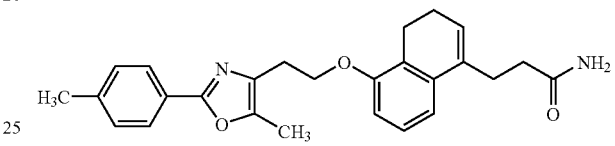

Under ice-cooling, to a methylene chloride (15 ml) suspension of the compound (625 mg) prepared in Example 2, oxalyl chloride (1.31 ml) and dimethylformamide (one drop) were added, followed by stirring at room temperature for 2 hours. The reaction mixture was concentrated. The residue was subjected to azeotropy with benzene. The obtained oil was dissolved in tetrahydrofuran (15 ml), and 28% aqueous ammonia was added thereto until a white precipitate appear, followed by stirring for 30 minutes. The reaction mixture was concentrated to thereby obtain the compound of the present invention (408 mg) having the following physical data. The obtained compound was used without purification in the subsequent reaction.

TLC: Rf 0.38 (chloroform:methanol=10:1); NMR (DMSO-d$_6$): δ 7.78(d, J=8.4 Hz, 2H), 7.29(d, J=8.4 Hz, 2H), 7.13(dd, J=8.7, 8.7 Hz, 1H), 6.92–6.85(m, 2H), 6.73(br, 1H), 5.82(t, J=4.5 Hz, 1H), 4.18(t, J=6.3 Hz, 2H), 2.91(t, J=6.3 Hz, 2H), 2.62–2.52(m, 4H), 2.19(m, 2H), 2.07(m, 2H).

REFERENCE EXAMPLE 31

3-(5-(2-(2-(4-methylphenyl)-5-methyloxazol-4-yl)ethoxy)-3,4-dihydronaphthalen-1-yl)propanenitrile

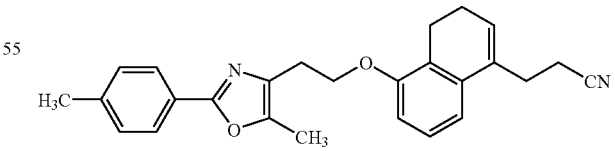

To a dioxane (15 ml) solution of the compound prepared in Example 10, pyridine (363 μl) and trifluoroacetic acid (423 μl) were added, followed by stirring at room temperature for 1 hour. The reaction mixture was concentrated, and the residue was diluted with ethyl acetate. The diluted solution was washed with 1 N hydrochloric acid, water and a saturated saline in this order, dried with anhydrous magnesium sulfate, and concentrated. The residue was purified by silica gel column chromatography (hexane:ethyl acetate=4:1) to thereby obtain the title compound (533 mg) having the following physical data.

TLC: Rf 0.48 (hexane:ethyl acetate=2:1); NMR(CDCl$_3$): δ 7.86(d, J=8.4 Hz, 2H), 7.26(d, J=8.4 Hz, 2H), 7.14(dd, J=7.8, 7.5 Hz, 1H), 6.83(d, J=7.5 Hz, $_1$H), 6.77(d, J=7.5 Hz, 1H), 5.98(t, J=4.5 Hz, 1H), 4.25(t, J=6.6 Hz, 2H), 2.98(t, J=6.6 Hz, 2H), 2.82–2.68(m, 4H), 2.53(t, J=7.8 Hz, 2H), 2.38(s, 3H), 2.36(s, 3H), 2.24(m, 2H).

EXAMPLE 11

5-(2-(5-(2-(5-methyl-2-(4-methylphenyl)oxazol-4-yl)ethoxy)-3,4-dihydronaphthalen-1-yl)ethyl)-1H-tetrazole

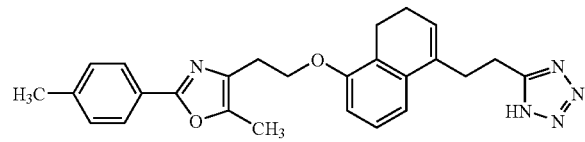

To a toluene (5 ml) solution of the compound (212 mg) prepared in Reference Example 31, azidotrimethyltin (163 mg) was added, followed by refluxing for 6 hours under argon atmosphere. After standing to cool, the reaction mixture was purified by silica gel column chromatography (chloroform:methanol=50:1) to thereby obtain the compound of the present invention (83 mg) having the following physical data.

TLC: Rf 0.43 (chloroform:methanol=10:1); NMR (DMSO-d$_6$): δ 7.79(d, J=8.1 Hz, 2H), 7.29(d, J=8.1 Hz, 2H), 7.15(dd, J=7.8, 7.8 Hz, 1H), 6.94(d, J=7.8 Hz, 1H), 6.92(d, J=7.8 Hz, 1H), 5.81(d, J=4.5 Hz, 1H), 4.19(t, J=6.6 Hz, 2H), 3.02(m, 2H), 2.91(t, J=6.6 Hz, 2H), 2.81(t, J=7.5 Hz, 2H), 2.54(t, J=8.4 Hz, 2H), 2.33(s, 6H), 2.04(m, 2H).

REFERENCE EXAMPLE 32

((5-methoxymethoxy-3,4-dihydronaphthalen-1-yl) methyl)malonic acid diethyl ester

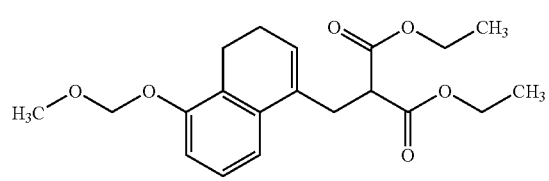

To an ethanol (1.5 ml) solution of the compound (400 mg) prepared in Reference Example 14, malonic acid diethyl ester (0.28 ml) and sodium ethoxide (0.55 ml, 2.6 in EtOH) were added, followed by stirring at 80° C. for 30 minutes. The reaction mixture was cooled to room temperature, and acetic acid and water were added thereto, followed by extracting with ethyl acetate. The extract was washed with a saturated saline, dried with anhydrous magnesium sulfate, and concentrated to thereby obtain the crude title compound having the following physical data. The obtained compound was used without purification in the subsequent reaction.

TLC: Rf 0.64 (hexane:ethyl acetate=2:1).

REFERENCE EXAMPLE 33

((5hydroxy-3,4-dihydronaphthalen-1-yl)methyl)malonic acid diethyl ester

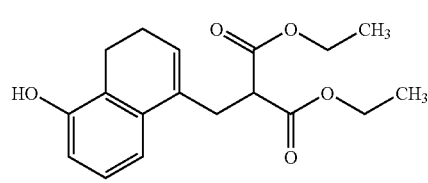

Under ice-cooling, to an ethanol (5 ml) solution of the compound prepared in Reference Example 32, 4N hydrogen chloride-ethyl acetate solution (0.7 ml) was added, followed by stirring at room temperature overnight. The reaction mixture was concentrated. The residue was purified by silica gel column chromatography (hexane:ethyl acetate=10:1 to 5:1) to thereby obtain the title compound (428 mg) having the following physical data.

TLC: Rf 0.43 (hexane:ethyl acetate=2:1); NMR(CDCl$_3$): δ 7.06(d, J=7.8 Hz, 1H), 6.86(d, J=7.8 Hz, 1H), 6.70(dd, J=7.8, 0.8 Hz, 1H), 5.93(brt, J=4.6 Hz, 1H), 5.27(brs, 1H), 4.19(q, J=7.2 Hz, 4H), 3.63(t, J=7.8 Hz, 1H), 3.06(dd, J=7.8, 1.0 Hz, 2H), 2.67(t, J=7.8 Hz, 2H), 2.28–2.15(m, 2H), 1.25(t, J=7.2 Hz, 6H).

REFERENCE EXAMPLE 34

((5-(2-(5-methyl-2-(4-methylphenyl)oxazol-4-yl) ethoxy)-3,4-dihydronaphthalen-1-yl)methyl)malonic acid diethyl ester

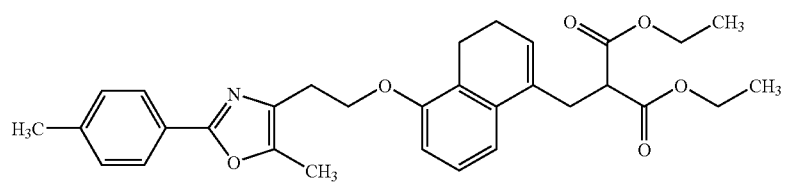

To a methylene chloride (10 ml) solution of the compound (456 mg) prepared in Reference Example 33 and the compound (373 mg) prepared in Reference Example 27, triphenylphosphine (561 mg) and 1,1'-(azodicarbonyl)dipiperidine (539 mg) were added, followed by stirring at room temperature overnight. The reaction mixture was concentrated. Diethyl ether was added to the residue, and an insoluble was removed by filtration. The filtrate was concentrated. The residue was purified by silica gel column chromatography (hexane:ethyl acetate=6:1). The obtained solid was recrystallized with diisopropyl ether to thereby obtain the title compound (422 mg) having the following physical data.

TLC: Rf 0.54 (hexane:ethyl acetate=2:1); NMR(CDCl$_3$): δ 7.86(d, J=8.1 Hz, 2H), 7.23(d, J=8.1 Hz, 2H), 7.13(dd, J=7.5, 7.5 Hz, 1H), 6.88(d, J=7.5 Hz, 1H), 6.81(d, J=7.5 Hz, 1H), 5.91(t, J=4.5 Hz, 1H), 4.29(t, J=6.6 Hz, 2H), 4.17(q, J=7.2 Hz, 2H), 4.16(q, J=7.2 Hz, 2H), 3.59(t, J=7.5 Hz, 1H), 3.05(t, J=7.8 Hz, 2H), 2.98(t, J=6.6 Hz, 2H), 2.38(s, 3H), 2.35(s, 3H), 2.16(m, 2H), 1.23(t, J=7.2 Hz, 6H).

EXAMPLE 12

4-((5-(2-(5-methyl-2-(4-methylphenyl)oxazol-4-yl)ethoxy)-3,4-dihydronaphthalen-1-yl)methyl)isooxazolidin-3,5-dione

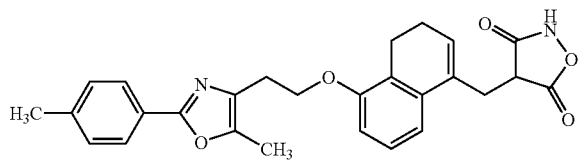

To an anhydrous methanol (10 ml) solution of hydroxyamine hydrochloride (87.5 mg), a methanol solution of sodium methylate (542 μl, 25 wt %) was added under argon atmosphere, followed by stirring at room temperature for 5 minutes. An insoluble was removed. To the filtrate, an anhydrous tetrahydrofuran (5 ml) of the compound (434 mg) prepared in Reference Example 34 was added under argon atmosphere, followed by stirring at 60° C. for 6 hours. The reaction mixture was concentrated. The residue was diluted with 1N hydrochloric acid. The diluted solution was extracted with a mixed solvent of diethyl ether and tetrahydrofuran. The extract was dried with anhydrous magnesium sulfate, and concentrated. The residue was recrystallized with methanol to thereby obtain the compound of the present invention (123 mg) having the following physical data.

TLC: Rf 0.36 (chloroform:methanol:acetic acid=20:2:1); NMR(DMSO-d$_6$): δ 7.79(d, J=8.4 Hz, 2H), 7.29(d, J=8.4 Hz, 2H), 7.12(dd, J=7.8, 7.8 Hz, 1H), 6.98(d, J=7.8 Hz, 1H), 6.89(d, J=7.8 Hz, 1H), 5.66(t, J=4.5 Hz, 1H), 4.18(t, J=6.3 Hz, 2H), 3.08(br s, 2H), 2.91(t, J=6.3 Hz, 2H), 2.56(t, J=8.1 Hz, 2H), 2.33(s, 3H), 2.32(s, 3H), 2.09(m, 2H).

FORMULATION EXAMPLE

Formulation Example 1

The following components were admixed in a conventional method and punched out to obtain 100 tablets each containing 50 mg of the active ingredient.

| | |
|---|---|
| 3-(5-(2-(2-(4-methylphenyl)-5-methyloxazol-4-yl)ethoxy)-3,4-dihydronaphthalen-1-yl)propanoic acid | 5.0 g |
| Carboxymethyl cellulose calcium (disintegrating agent) | 0.2 g |
| Magnesium stearate (lubricant) | 0.1 g |
| Microcrystalline cellulose | 4.7 g |

Formulation Example 2

The following components were admixed in a conventional method, and the solution was sterilized in a conventional method, placed at 5 ml into ampoules and freeze-dried in a conventional method to thereby obtain 100 ampoules each containing 20 mg of the active ingredient.

| | |
|---|---|
| 3-(5-(2-(2-(4-methylphenyl)-5-methyloxazol-4-yl)ethoxy)-3,4-dihydronaphthalen-1-yl)propanoic acid | 2.0 g |
| Mannitol | 20 g |
| Distilled water | 1000 ml |

What is claimed is:

1. A compound 3-(5-(2-(2-(4-methylphenyl)-5-methyloxazol-4-yl)ethoxy)-3,4-dihydronaphthalen-1-yl)propanoic acid or a nontoxic salt thereof.

2. A compound 3-(5-(2-(2-(4-methylphenyl)-5-methyloxazol-4-yl)ethoxy)-3,4-dihydronaphthalen-1-yl)propanoic acid.

* * * * *

SEQUENCE LISTING

<160> NUMBER OF SEQ ID NOS: 3

<210> SEQ ID NO 1
<211> LENGTH: 85
<212> TYPE: DNA
<213> ORGANISM: Artificial Sequence
<220> FEATURE:
<223> OTHER INFORMATION: Enhancer sequence including 4 times
      repeated Gal4 protein response sequence

<400> SEQUENCE: 1
tcgacggagt actgtcctcc gcgacggagt actgtcctcc gcgacggagt actgtcctcc    60
gcgacggagt actgtcctcc gagct                                          85

<210> SEQ ID NO 2

-continued

```
<211> LENGTH: 9
<212> TYPE: PRT
<213> ORGANISM: Artificial Sequence
<220> FEATURE:
<223> OTHER INFORMATION: Nuclear localization signal derived
                        from SV-40 T-antigen

<400> SEQUENCE: 2

Ala Pro Lys Lys Lys Arg Lys Val Gly
1               5

<210> SEQ ID NO 3
<211> LENGTH: 9
<212> TYPE: PRT
<213> ORGANISM: Influenza virus
<220> FEATURE:
<221> NAME/KEY: MISC_FEATURE
<223> OTHER INFORMATION: Hemagglutinin epitope

<400> SEQUENCE: 3

Tyr Pro Tyr Asp Val Pro Asp Tyr Ala
1               5
```